United States Patent
Aebi et al.

(10) Patent No.: US 6,951,879 B2
(45) Date of Patent: Oct. 4, 2005

(54) HETEROAROMATE OSC INHIBITORS

(75) Inventors: Johannes Aebi, Basel (CH); Jean Ackermann, Riehen (CH); Henrietta Dehmlow, Grenzach-Wyhlen (DE); Hans-Peter Maerki, Basel (CH); Olivier Morand, Hegenheim (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/999,424

(22) Filed: Oct. 31, 2001

(65) Prior Publication Data

US 2002/0086891 A1 Jul. 4, 2002

(30) Foreign Application Priority Data

Nov. 2, 2000 (EP) .............................. 00123826

(51) Int. Cl.$^7$ .................... A61K 31/428; C07D 275/04
(52) U.S. Cl. ...................... 514/373; 548/207
(58) Field of Search ........................ 548/207; 514/373

(56) References Cited

U.S. PATENT DOCUMENTS

| | | |
|---|---|---|
| 4,410,539 A | 10/1983 | Cross et al. |
| 5,994,371 A | 11/1999 | Black et al. |

FOREIGN PATENT DOCUMENTS

| | | |
|---|---|---|
| DE | 39 05 364 | 8/1990 |
| EP | 778 271 | 6/1997 |
| WO | WO 98/21188 | 5/1998 |

OTHER PUBLICATIONS

Gotto et al., Circulation 81, pp. 1721–1733 (1990).
Stein et al., Nutr. Metab. Cardiovasc. Dis. 2, pp. 113–156 (1992).
Illingworth, Med. Clin. North Am. 84, pp. 23–42 (2000).
Ross et al., Arch. Intern. Med. 159, pp. 1793–1802 (1999).
Ellen et al., J. Cardiol. 81, pp. 60B–65B (1998).
Shepherd, Eur. Heart J. 16, pp. 5–13 (1995).
Davignon et al., Can. J. Cardiol 8, pp. 843–864 (1992).
Pedersen et al., Drug Safety 14, pp. 11–24 (1996).
Morand et al., J. Lipid Research 38, pp., 373–390 (1997).
Mark et al., J. Lipid Research 37, pp. 148–158 (1996).
Peffley et al., Biochem. Pharmacol 56, pp. 439–449 (1998).
Nelson et al., J. Biol. Chem. 256, pp. 1067–1068 (1981).
Spencer et al., J. Biol. Chem. 260, pp. 13391–13394 (1985).
Panini et al., J. Lipid Research 27, pp. 1190–1204 (1986).
Ness et al., Arch. Biochem. Biophys. 308, pp. 420–425 (1994).
Janowski et al., Proc. Natl. Acad. Sci. USA 96, pp. 266–271 (1999).
Venkateswaran et al., J. Biol. Chem. 275, pp. 14700–14707 (2000).
Costet et al., J. Biol. Chem. 275, pp. 28240–28245 (2000).
Ordovas et al., Nutr. Rev. 58, pp. 76–79 (2000).
Schmitz et al., Front. Biosci 6, D505–D514 (2001).
Tobin et al., Mol. Endocrinol. 14, pp 741–752 (2000).
Marshall et al., J. Org. Chem. 61(17), pp. 5729–5735 (1996).
Baker et al., J. Chem. Soc. Perkin Trans. 1, pp. 1415–1421 (1990).
Belostotskii et al., Tetrahedron Letters 35(28), pp. 5075–5076 (1994).
Wolfe et al., J. Org. Chem., 65(4), pp. 1158–1174 (2000).
Palucki et al., J. Am. Chem. Soc., 119(14), pp. 3395–3396 (1997).
Denton et al., Synlett, No. 1, pp. 55–56 (1999).
Chaplinski et al., Angew. Chem. Int. Ed. Engl., 35, pp. 413–414 (1997).
Mattson et al., J. Org. Chem., 55, pp. 2552–2554 (1990).
Stara et al., Collect. Czech. Chem. Commun. 64(4), pp. 649–672 (1999).
P.E. Cross, et al, *Journal of Medicinal Chemistry*, 29(9), pp. 1637–1643 (1986).

*Primary Examiner*—Joseph K. McKane
*Assistant Examiner*—Rebecca Anderson
(74) *Attorney, Agent, or Firm*—George W. Johnston; Patricia S. Roca-Tramaloni

(57) ABSTRACT

The present invention relates to heteroaromate OSC inhibitors. The compounds are useful for the treatment and/or prophylaxis of diseases which are associated with 2,3-oxidosqualene-lanosterol cyclase such as hypercholesterolemia, hyperlipemia, arteriosclerosis, vascular diseases, mycoses, gallstones, tumors and/or hyperproliferative disorders, and treatment and/or prophylaxis of impaired glucose tolerance and diabetes.

22 Claims, No Drawings

HETEROAROMATE OSC INHIBITORS

FIELD OF THE INVENTION

The present invention is concerned with novel heteroaromates, their manufacture and their use as medicaments.

BACKGROUND OF THE INVENTION

The compounds of the present invention inhibit 2,3-oxidosqualene-lanosterol cyclase (EC 5.4.99.) which is required for the biosynthesis of cholesterol, ergosterol and other sterols. Causal risk factors that directly promote the development of coronary and peripheral atherosclerosis include elevated low-density lipoprotein cholesterol (LDL-C), low high-density lipoprotein cholesterol (HDL-C), hypertension, cigarette smoking and diabetes mellitus. Other synergistic risk factors include elevated concentrations of triglyceride (TG)-rich lipoproteins, small, dense low-density lipoprotein particles, lipoprotein (a) (Lp(a)), and homocysteine. Predisposing risk factors modify the causal or conditional risk factors and thus affect atherogenesis indirectly. The predisposing risk factors are obesity, physical inactivity, family history of premature CVD, and male sex. The strong connection between coronary heart disease (CHD) and high LDL-C levels in plasma, and the therapeutic advantage of lowering elevated LDL-C levels are now well established (Gotto et al., Circulation 81, 1990, 1721–1733; Stein et al., Nutr. Metab. Cardiovasc. Dis. 2, 1992, 113–156; Illingworth, Med. Clin. North. Am. 84, 2000, 23–42). Cholesterol-rich, sometimes unstable, atherosclerotic plaques lead to the occlusion of blood vessels resulting in an ischemia or an infarct. Studies with respect to primary prophylaxis have shown that a lowering of plasma LDL-C levels in plasma reduces the frequency of non-fatal incidences of CHD, while the overall morbidity remains unchanged. The lowering of plasma LDL-C levels in patients with pre-established CHD (secondary intervention) reduces CHD mortality and morbidity; meta-analysis of different studies shows that this decrease is proportional to the reduction of the LDL-C (Ross et al., Arch. Intern. Med. 159, 1999, 1793–1802).

The clinical advantage of cholesterol lowering is greater for patients with pre-established CHD than for asymptomatic persons with hypercholesterolemia. According to current guidelines, cholesterol lowering treatment is recommended for patients who had survived a myocardial infarct or patients suffering from angina pectoris or another atherosclerotic disease, with a target LDL-C level of 100 mg/dl.

Preparations such as bile acid sequestrants, fibrates, nicotinic acid, probucol as well as statins, i.e. HMG-Co-A reductase inhibitors such as simvastatin and atorvastatin, are used for usual standard therapies. The best statins reduce plasma LDL-C effectively by at least 40%, and also plasma triglycerides, a synergistic risk factor, but less effectively. In contrast, fibrates reduce plasma triglycerides effectively, but not LDL-C. Combination of a statin and a fibrate proved to be very efficacious in lowering LDL-C and triglycerides (Ellen and McPherson, J. Cardiol. 81, 1998, 60B–65B), but safety of such a combination remains an issue (Shepherd, Eur. Heart J. 16, 1995, 5–13). A single drug with a mixed profile combining effective lowering of both LDL-C and triglycerides would provide additional clinical benefit to asymptomatic and symptomatic patients.

In humans, statins are well tolerated at standard dosage, but reductions in non-sterol intermediates in the cholesterol synthesis pathway, such as isoprenoids and coenzyme Q, may be associated with adverse clinical events at high doses (Davignon et al., Can. J. Cardiol. 8, 1992, 843–864; Pederson and Tobert, Drug Safety 14, 1996, 11–24).

This has stimulated the search for, and development of compounds that inhibit cholesterol biosynthesis, yet act distal to the synthesis of these important, non-sterol intermediates. 2,3-oxidosqualene:lanosterol cyclase (OSC), a microsomal enzyme, represents a unique target for a cholesterol-lowering drug (Morand et al., J. Lipid Res., 38, 1997, 373–390; Mark et al., J. Lipid Res. 37, 1996, 148–158). OSC is downstream of farnesyl-pyrophosphate, beyond the synthesis of isoprenoids and coenzyme Q. In hamsters, pharmacologically active doses of an OSC inhibitor showed no adverse side-effects, in contrast to a statin which reduced food-intake and body weight, and increased plasma bilirubin, liver weight and liver triglyceride content (Morand et al., J. Lipid Res., 38, 1997, 373–390). The compounds described in European Patent Application No. 636 367, which inhibit OSC and which lower the total cholesterol in plasma, belong to these substances.

OSC inhibition does not trigger the overexpression of HMGR because of an indirect, negative feed-back regulatory mechanism involving the production of 24(S),25-epoxycholesterol (Peffley et al., Biochem. Pharmacol. 56, 1998, 439–449; Nelson et al., J. Biol. Chem. 256, 1981, 1067–1068; Spencer et al., J. Biol. Chem. 260, 1985, 13391–13394; Panini et al., J. Lipid Res. 27, 1986, 1190–1204; Ness et al., Arch. Biochem. Biophys. 308, 1994, 420–425). This negative feed-back regulatory mechanism is fundamental to the concept of OSC inhibition because (i) it potentiates synergistically the primary inhibitory effect with an indirect down-regulation of HMGR, and (ii) it prevents the massive accumulation of the precursor monooxidosqualene in the liver. In addition, 24(S),25-epoxycholesterol was found to be one of the most potent agonists of the nuclear receptor LXR (Janowski et al., Proc. Natl. Acad. Sci. USA, 96, 1999, 266–271). Considering that 24(S),25-epoxycholesterol is a by-product of inhibition of OSC it is hypothesized that the OSC inhibitors of the present invention could also indirectly activate LXR-dependent pathways such as (i) cholesterol-7alpha-hydroxylase to increase the consumption of cholesterol via the bile acid route, (ii) expression of ABC proteins with the potential to stimulate reverse cholesterol transport and increase plasma HDL-C levels (Venkateswaran et al., J. Biol. Chem. 275, 2000, 14700–14707; Costet et al., J. Biol. Chem. June 2000, in press; Ordovas, Nutr Rev 58, 2000, 76–79, Schmitz and Kaminsky, Front Biosci 6, 2001, D505–D514), and/or inhibit intestinal cholesterol absorption (Mangelsdorf, XIIth International Symposium on Atherosclerosis, Stockholm, June 2000). In addition, possible cross talks between fatty acid and cholesterol metabolism mediated by liver LXR have been hypothesized (Tobin et al., Mol. Endocrinol. 14, 2000, 741–752).

SUMMARY OF THE INVENTION

The present compounds of formula I inhibit OSC and therefore also inhibit the biosynthesis of cholesterol, ergosterol and other sterols, and reduce the plasma cholesterol levels. They can therefore be used in the therapy and prophylaxis of hypercholesterolemia, hyperlipemia, arteriosclerosis and vascular diseases in general. Furthermore, they can be used in the therapy and/or prevention of mycoses, parasite infections, gallstones, cholestatic liver disorders, tumors and hyperproliferative disorders, e.g. hyperproliferative skin and vascular disorders. In addition, it has unexpectedly been found that the compounds of the present invention can also be of therapeutic use to improve glucose tolerance in order to treat and/or prevent related diseases such as diabetes. The compounds of the present invention further exhibit improved pharmacological properties compared to known compounds.

In particular, the invention relates to compounds of the formula (I)

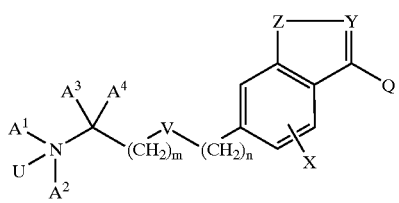

wherein

U is O or a lone pair,
Y N, or $CR^1$,
Z is S, or $S(O_2)$,
V is a) —CH=CH—, and m and n are 0, or
b) —$CH_2$—, and m+n≦2, or
c) O or $NR^2$, and m is 1 to 6, n is 1 to 6, m+n≦7, or m is 1 to 3, n is 0, or
d) S, and m is 1 to 7, n is 0 to 6, m+n≦7, or
e) —C≡C—, and m is 0 to 7, n is 0 to 7, m+n is ≦7,
Q is cycloalkyl, cycloalkyl-lower-alkyl, phenyl optionally substituted by 1 to 3 substituents independently selected from the group as defined for $R^3$, or an alkyl, alkenyl or alkadienyl group optionally substituted by OH,
$A^1$ is hydrogen, lower-alkenyl, or lower-alkyl optionally substituted with hydroxy, lower-alkoxy, or thio-lower-alkoxy,
$A^2$ is cycloalkyl, cycloalkyl-lower-alkyl, lower-alkenyl, lower-alkinyl, heteroaryl, or lower-alkyl optionally substituted with halogen, hydroxy, lower-alkoxy, or thio-lower-alkoxy, or
$A^1$ and $A^2$ are bonded to each other to form a ring and —$A^1$—$A^2$— is lower-alkylene, or lower-alkenylene, optionally substituted by $R^4$, in which one —$CH_2$— group of —$A^1$—$A^2$— can optionally be replaced by a $NR^5$, S, or O, or —$A^1$—$A^2$— is —CH=N=CH=CH— which can optionally be substituted by lower-alkyl,
$A^3$ and $A^4$ independently from each other are hydrogen or lower-alkyl, or
$A^3$ and $A^4$ are bonded to each other to form a ring together with the carbon atom to which they are attached and —$A^3$—$A^4$— is —$(CH_2)_{2-5}$— which can optionally be mono- or multiply-substituted by lower-alkyl,
X is hydrogen or one or more optional halogen and/or lower-alkyl substituents,
$R^1$ is hydrogen or lower-alkyl,
$R^2$ is hydrogen or lower-alkyl,
$R^3$ is halogen, $N(R^6, R^7)$, piperidyl, piperazinyl, piperazinylethanone, morpholinyl, $CONH_2$, CN, $NO_2$, $CF_3$, OH, lower-alkoxy, thio-lower-alkoxy, or is lower-alkyl, lower-alkenyl, or lower-alkinyl, optionally substituted with OH, SH or $N(R^8, R^9)$,
$R^4$ is hydroxy, lower-alkyl, lower-alkoxy, or thio-lower-alkoxy,
$R^5$ is hydrogen, lower-alkyl, or lower-alkyl-carbonyl,
$R^6$ and $R^7$ independently from each other are selected from the group consisting of hydrogen, lower-alkyl, phenyl and benzyl,
$R^8$ and $R^9$ independently from each other are selected from the group consisting of hydrogen and lower-alkyl, and pharmaceutically acceptable salts and/or pharmaceutically acceptable esters of compounds of formula I.

DETAILED DESCRIPTION OF THE INVENTION

Unless otherwise indicated the following definitions are set forth to illustrate and define the meaning and scope of the various terms used to describe the invention herein.

In this specification the term "lower" is used to mean a group consisting of one to seven, preferably of one to four carbon atom(s).

The term "lone pair" refers to an unbound electron pair, in particular to the unbound electron pair of a nitrogen atom in e.g. an amine.

The term "halogen" refers to fluorine, chlorine, bromine and iodine, with fluorine, chlorine and bromine being preferred.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. Lower-alkyl groups as defined below also are preferred alkyl groups. Alkyl groups can be substituted e.g. with halogen, particularly with flourine or chlorine, hydroxy, lower-alkoxy, and/or lower-alkoxy-carbonyl.

The term "lower-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like. A lower-alkyl group may have a substitution pattern as described earlier in connection with the term "alkyl".

The term "cycloalkyl" refers to a monovalent carbocyclic radical of 3 to 10 carbon atom(s), preferably 3 to 6 carbon atoms.

The term "alkoxy" refers to the group R'—O—, wherein R' is an alkyl. The term "lower-alkoxy" refers to the group R'—O—, wherein R' is a lower-alkyl. The term "thioalkoxy" refers to the group R'—S—, wherein R' is an alkyl. The term "thio-lower-alkoxy" refers to the group R'—S—, wherein R' is a lower-alkyl.

The term "alkenyl", alone or in combination with other groups, stands for a straight-chain or branched hydrocarbon residue comprising an olefinic bond and up to 20, preferably up to 16 carbon atoms, more preferrably up to 10 carbon atoms. Lower-alkenyl groups as described below also are preferred alkenyl groups. The term "lower-alkenyl" refers to a straight-chain or branched hydrocarbon residue comprising an olefinic bond and up to 7, preferably up to 4 carbon atoms, such as e.g. 2-propenyl. An alkenyl or lower-alkenyl group may have a substitution pattern as described earlier in connection with the term "alkyl".

The term "alkadienyl", alone or in combination with other groups, stands for a straight-chain or branched hydrocarbon residue comprising 2 olefinic bonds and up to 20, preferably up to 16 carbon atoms, more preferably up to 10 carbon atoms. Lower-alkadienyl groups as described below also are preferred alkadienyl groups. The term "lower-alkadienyl" refers to a straight-chain or branched hydrocarbon residue comprising 2 olefinic bonds and up to 7 carbon atoms. An alkadienyl or lower-alkadienyl group may have a substitution pattern as described earlier in connection with the term "alkyl".

The term "alkinyl", alone or in combination with other groups, stands for a straight-chain or branched hydrocarbon residue comprising a tripple bond and up to 20, preferably up to 16 carbon atoms. The term "lower-alkinyl" refers to a straight-chain or branched hydrocarbon residue comprising a tripple bond and up to 7, preferably up to 4 carbon atoms, such as e.g. 2-propinyl. An alkinyl or lower-alkinyl group may have a substitution pattern as described earlier in connection with the term "alkyl".

The term "alkylene" refers to a straight chain or branched divalent saturated aliphatic hydrocarbon group of 1 to 20 carbon atoms, preferably 1 to 16 carbon atoms. The term "lower-alkylene" refers to a straight chain or branched divalent saturated aliphatic hydrocarbon group of 1 to 7, preferably 3 to 6 carbon atoms. An alkylene or lower-alkylene group may have a substitution pattern as described earlier in connection with the term "alkyl".

The term "alkenylene" refers to a straight chain or branched divalent hydrocarbon group comprising an olefinic bond and up to 20 carbon atoms, preferably up to 16 carbon atoms. The term "lower-alkenylene" refers to a straight chain or branched divalent hydrocarbon group comprising an olefinic bond and up to 7, preferably up to 6 C-atoms. An alkenylene or lower-alkenylene group may have a substitution pattern as described earlier in connection with the term "alkyl".

The term "aryl" relates to the phenyl or naphthyl group which can optionally be mono- or multiply-substituted by lower-alkyl, dioxo-lower-alkylene (forming e.g. a benzodioxyl group), halogen, hydroxy, cyano, $CF_3$, $NH_2$, $N(lower-alkyl)_2$, aminocarbonyl, carboxy, nitro, lower-alkoxy, thio-lower-alkoxy, lower-alkylcarbonyl, lower-alkylcarbonyloxy, aryl, or aryloxy. Preferred substituents are lower-alkyl, lower-alkoxy, thio-lower-alkoxy, lower-alkylcarbonyl, lower-alkoxycarbonyl, fluorine, chlorine, bromine, CN, $CF_3$, and/or dioxo-lower-alkylene. More preferred substituents are fluorine, chlorine, bromine and $CF_3$.

The term "heteroaryl" refers to an aromatic 5- or 6-membered ring which can comprise 1, 2 or 3 atoms selected from nitrogen, oxygen and/or sulphur such as furyl, pyridyl, pyrimidinyl, pyrazinyl, pyridazinyl, thienyl, isoxazolyl, oxazolyl, imidazolyl, or pyrrolyl. A heteroaryl group may have a substitution pattern as described earlier in connection with the term "aryl".

The term "pharmaceutically acceptable salts" embraces salts of the compounds of formula (I) with inorganic or organic acids such as hydrochloric acid, hydrobromic acid, nitric acid, sulphuric acid, phosphoric acid, citric acid, formic acid, maleic acid, acetic acid) fumaric acid, succinic acid, tartaric acid, methanesulphonic acid, p-toluenesulphonic acid and the like, which are non toxic to living organisms. Preferred salts are formates, hydrochlorides and hydrobromides.

The term "pharmaceutically acceptable esters" embraces esters of the compounds of formula (I), in which hydroxy groups have been converted to the corresponding esters with inorganic or organic acids such as nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

In detail, the present invention relates to compounds of formula (I)

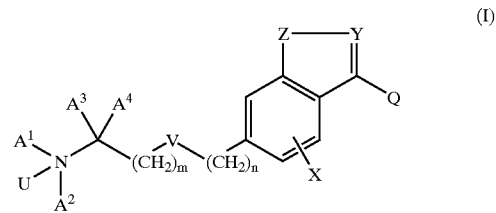

(I)

wherein

U is O or a lone pair,
Y N, or $CR^1$,
Z is S, or $S(O_2)$,
V is a) —CH=CH—, and m and n are 0, or
b) —$CH_2$—, and m+n≦2, or
c) O or $NR^2$, and m is 1 to 6, n is 1 to 6, m+n≦7, or m is 1 to 3, n is 0, or
d) S, and m is 1 to 7, n is 0 to 6, m+n≦7, or
e) —C≡C—, and m is 0 to 7, n is 0 to 7, m+n is ≦7,
Q is cycloalkyl, cycloalkyl-lower-alkyl, phenyl optionally substituted by 1 to 3 substituents independently selected from the group as defined for $R^3$, or an alkyl, alkenyl or alkadienyl group optionally substituted by OH,
$A^1$ is hydrogen, lower-alkenyl, or lower-alkyl optionally substituted with hydroxy, lower-alkoxy, or thio-lower-alkoxy,
$A^2$ is cycloalkyl, cycloalkyl-lower-alkyl, lower-alkenyl, lower-alkinyl, heteroaryl, or lower-alkyl optionally substituted with halogen, hydroxy, lower-alkoxy, or thio-lower-alkoxy, or
$A^1$ and $A^2$ are bonded to each other to form a ring and —$A^1$—$A^2$— is lower-alkylene, or lower-alkenylene, optionally substituted by $R^4$, in which one —$CH_2$— group of
—$A^1$—$A^2$— can optionally be replaced by a $NR^5$, S, or O, or —$A^1$—$A^2$— is —CH=N=CH=CH— which can optionally be substituted by lower-alkyl,
$A^3$ and $A^4$ independently from each other are hydrogen or lower-alkyl, or
$A^3$ and $A^4$ are bonded to each other to form a ring together with the carbon atom to which they are attached and —$A^3$—$A^4$— is —$(CH_2)_{2-5}$— which can optionally be mono- or multiply-substituted by lower-alkyl,
X is hydrogen or one or more optional halogen and/or lower-alkyl substituents, $R^1$ is hydrogen or lower-alkyl,
$R^2$ is hydrogen or lower-alkyl,
$R^3$ is halogen, $N(R^6,R^7)$, piperidyl, piperazinyl, piperazinyl-ethanone, morpholinyl, $CONH_2$, CN, $NO_2$, $CF_3$, OH, lower-alkoxy, thio-lower-alkoxy, or is lower-alkyl, lower-alkenyl, or lower-alkinyl, optionally substituted with OH, SH or $N(R^8,R^9)$,
$R^4$ is hydroxy, lower-alkyl, lower-alkoxy, or thio-lower-alkoxy,
$R^5$ is hydrogen, lower-alkyl, or lower-alkyl-carbonyl,
$R^6$ and $R^7$ independently from each other are selected from the group consisting of hydrogen, lower-alkyl, phenyl and benzyl,
$R^8$ and $R^9$ independently from each other are selected from the group consisting of hydrogen and lower-alkyl, and pharmaceutically acceptable salts and/or pharmaceutically acceptable esters thereof.

Preferred are compounds of formula (I) and/or pharmaceutically acceptable salts thereof. Other preferred embodiments relate to compounds of formula (I) wherein U is a lone pair or to compounds of formula (I) wherein U is O.

Each of the definitions of V given above, a), b), c), d) and e), individually or in combination constitutes a preferred embodiment of the present invention. Compounds as described above in which V is O, m is 1 to 6, n is 1 to 6, and m+n≤7 relate to a further preferred embodiment of the present invention. Another preferred embodiment of the present invention are compounds as described above, wherein V is O, m is 1 to 3, and n is 0. Other preferred compounds are those, wherein V is —C≡C—, m is 0 to 2, and n is 0. Further preferred compounds are those, wherein V is —CH$_2$— and m+n≤2.

Other preferred compounds of the present invention are those in which $A^1$ represents hydrogen, methyl, or ethyl optionally substituted with hydroxy or methoxy. Another group of preferred compounds of the present invention are those in which $A^2$ represents methyl, n-propyl, i-propyl, 2-propenyl, 2-propinyl, 1,1-dimethyl-2-propinyl, cyclopropyl-methylene, or ethyl optionally substituted with hydroxy or methoxy, with those compounds wherein $A^2$ represents methyl, ethyl, 2-hydroxy-ethyl, 2-methoxy-ethyl, n-propyl, 2-propenyl, or cyclopropyl-methylene being especially preferred. If $A^2$ is heteroaryl, pyridyl and pyrimidinyl, which can optionally be substituted with lower-alkyl, preferably with methyl, are preferred heteroaryl groups. Further preferred compounds as defined above are those wherein $A^2$ is 2-Methyl-pyrimidin-4-yl.

Compounds of formula (I), wherein $A^1$ and $A^2$ are bonded to each other to form a ring and —$A^1$—$A^2$— is lower-alkylene, optionally substituted by $R^4$, in which one —CH$_2$— group of —$A^1$—$A^2$— can optionally be replaced by $NR^5$ or O, wherein $R^4$ is hydroxy, and $R^5$ is lower-alkyl or lower-alkyl-carbonyl, or —$A^1$—$A^2$— is —CH=N=CH=CH—, are also preferred, with those compounds wherein said optional substituent $R^5$ is methyl being particularly preferred. If —$A^1$—$A^2$— is —CH=N=CH=CH— which can optionally be substituted by lower-alkyl, —CH=N=CH=CH— is preferably substituted by methyl. In compounds wherein —$A^1$—$A^2$— is —CH=N=CH=CH—, $A^1$ and $A^2$, together with the nitrogen atom to which they are bound, form an imidazol ring. In compounds wherein $A^1$ and $A^2$ are bonded to each other to form a ring, said ring is preferably a 4-, 5-, or 6-membered ring such as e.g. piperidinyl or pyrrolidinyl. Compounds, wherein —$A^1$—$A^2$— is —(CH$_2$)$_5$— are also preferred.

A further preferred embodiment of the present invention relates to compounds of formula (I), wherein $A^3$ and/or $A^4$ represent hydrogen. In addition, compounds of formula (I) as defined above, wherein $A^3$ and/or $A^4$ represent methyl, relate to a preferred embodiment of the present invention. Compounds of formula (I) as defined above, wherein $A^3$ and $A^4$ are bonded to each other to form a cyclopentyl-ring or a cyclohexyl-ring together with the carbon atom to which they are attached and —$A^3$—$A^4$— is —(CH$_2$)$_4$— or —(CH$_2$)$_5$— respectively represent another preferred embodiment of the present invention. The term —(CH$_2$)$_{2-5}$— denotes the groups —(CH$_2$)$_2$—, —(CH$_2$)$_3$—, —(CH$_2$)$_4$— and —(CH$_2$)$_5$—.

In addition, compounds as described before, wherein Y is $CR^1$ and $R^1$ is methyl, are preferred. Furthermore, compounds in which Y is N relate to a preferred embodiment of the present invention. Other preferred compounds are those, wherein Z is S. Compounds, wherein Z is SO$_2$ are also preferred.

Compounds of formula (I), wherein Q is phenyl optionally substituted by 1 to 3 substituents independently selected from the group as defined for $R^3$, or an alkyl or alkenyl group optionally substituted by OH, wherein $R^3$ is as defined above, represent a preferred embodiment of the present invention, with those compounds wherein Q is phenyl optionally substituted by 1 to 3 substituents independently selected from the group as defined for $R^3$, wherein $R^3$ is fluorine, chlorine, bromine, or $CF_3$ being more preferred, and with those compounds wherein Q is 4-chloro-phenyl, 4-bromo-phenyl, or 4-trifluoromethyl-phenyl being particularly preferred. Another preferred group relates to compounds wherein X is hydrogen.

Further preferred embodiments of the present invention are those compounds as defined above wherein V is not —CH$_2$— and/or not —CH=CH—.

Compounds of formula (I), in which $A^2$ is cycloalkyl, cycloalkyl-lower-alkyl, lower-alkenyl, lower-alkinyl, or lower-alkyl optionally substituted with hydroxy, lower-alkoxy, or thio-lower-alkoxy, are preferred. Further, compounds in which $A^1$ and $A^2$ are bonded to each other to form a ring and —$A^1$—$A^2$— is lower-alkylene, or lower-alkenylene, optionally substituted by $R^4$, in which one —CH$_2$— group of —$A^1$—$A^2$— can optionally be replaced by a $NR^5$, S, or O, are preferred. Further, compounds in which $A^3$ and $A^4$ are not bonded to each other, are preferred. Compounds, in which $R^3$ is halogen, NH$_2$, N(lower-alkyl)$_2$, CONH$_2$, CN, NO$_2$, CF$_3$, OH, lower-alkoxy, thio-lower-alkoxy, or is lower-alkyl, lower-alkenyl, or lower-alkinyl, optionally substituted with OH, SH or NH$_2$, are also preferred.

Another preferred embodiment of the present invention relates to compounds of formula (I)

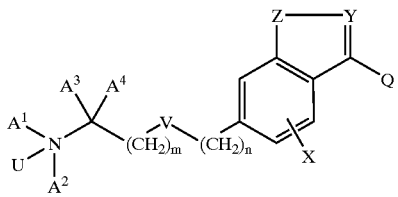

wherein

U is O or a lone pair,
Y N, or CR$^1$,
Z is S, or S(O$_2$),
V is a) —CH═CH—, and m and n are 0, or
b) —CH$_2$—, and m+n≦2, or
c) O or NR$^2$, and m is 1 to 6, n is 1 to 6, m+n≦7, or m is 1 to 3, n is 0, or
d) S, and m is 1 to 7, n is 0 to 6, m+n≦7, or
e) —C≡C—, and m is 0 to 7, n is 0 to 7, m+n is ≦7,
Q is cycloalkyl, cycloalkyl-lower-alkyl, phenyl optionally substituted by 1 to 3 substituents independently selected from the group as defined for R$^3$, or an alkyl, alkenyl or alkadienyl group optionally substituted by OH,
A$^1$ is hydrogen, lower-alkenyl, or lower-alkyl optionally substituted with hydroxy, lower-alkoxy, or thio-lower-alkoxy,
A$^2$ is cycloalkyl, cycloalkyl-lower-alkyl, lower-alkenyl, lower-alkinyl, or lower-alkyl optionally substituted with hydroxy, lower-alkoxy, or thio-lower-alkoxy, or
A$^1$ and A$^2$ are bonded to each other to form a ring and —A$^1$—A$^2$— is lower-alkylene, or lower-alkenylene, optionally substituted by R$^4$, in which one —CH$_2$— group of —A$^1$—A$^2$— can optionally be replaced by a NR$^5$, S, or O,
A$^3$ and A$^4$ independently from each other are hydrogen or lower-alkyl,
X is hydrogen or one or more optional halogen and/or lower-alkyl substituents,
R$^1$ is hydrogen or lower-alkyl,
R$^2$ is hydrogen or lower-alkyl,
R$^3$ is halogen, NH$_2$, N(lower-alkyl)$_2$, CONH$_2$, CN, NO$_2$, CF$_3$, OH, lower-alkoxy, thio-lower-alkoxy, or is lower-alkyl, lower-alkenyl, or lower-alkinyl, optionally substituted with OH, SH or NH$_2$,
R$^4$ is hydroxy, lower-alkyl, lower-alkoxy, or thio-lower-alkoxy,
R$^5$ is hydrogen, lower-alkyl, or lower-alkyl-carbonyl, and pharmaceutically acceptable salts and/or pharmaceutically acceptable esters thereof.

Preferred compounds of general formula (I) are those selected from the group consisting of Allyl-[2-[3-(4-bromo-phenyl)-benzo[d]isothiazol-6-yloxy]-ethyl]-methyl-amine,
[2-[3-(4-Bromo-phenyl)-benzo[d]isothiazol-6-yloxy]-ethyl]-dimethyl-amine,
Allyl-[3-[3-(4-bromo-phenyl)-benzo[d]isothiazol-6-yloxy]-propyl]-methyl-amine,
[3-[3-(4-Bromo-phenyl)-benzo[d]isothiazol-6-yloxy]-propyl]-dimethyl-amine,
Allyl-[4-[3-(4-bromo-phenyl)-benzo[d]isothiazol-6-yloxy]-butyl]-methyl-amine,
[4-[3-(4-Bromo-phenyl)-benzo[d]isothiazol-6-yloxy]-butyl]-dimethyl-amine,
2-[[4-[3-(4-Bromo-phenyl)-benzo[d]isothiazol-6-yloxy]-butyl]-methyl-amino]-ethanol,
2-[[3-[3-(4-Bromo-phenyl)-benzo[d]isothiazol-6-yloxy]-propyl]-methyl-amino]-ethanol,
2-[[2-[3-(4-Bromo-phenyl)-benzo[d]isothiazol-6-yloxy]-ethyl]-methyl-amino]-ethanol,
[4-[3-(4-Bromo-phenyl)-benzo[d]isothiazol-6-yloxy]-butyl]-(2-methoxy-ethyl)-methyl-amine,
[3-[3-(4-Bromo-phenyl)-benzo[d]isothiazol-6-yloxy]-propyl]-(2-methoxy-ethyl)-methyl-amine,
[2-[3-(4-Bromo-phenyl)-benzo[d]isothiazol-6-yloxy]-ethyl]-(2-methoxy-ethyl)-methyl-amine,
3-(4-Bromo-phenyl)-6-(4-morpholin-4-yl-butoxy)-benzo[d]isothiazole,
3-(4-Bromo-phenyl)-6-(3-morpholin-4-yl-propoxy)-benzo[d]isothiazole,
3-(4-Bromo-phenyl)-6-(2-morpholin-4-yl-ethoxy)-benzo[d]isothiazole,
2-[[4-[3-(4-Bromo-phenyl)-benzo[d]isothiazol-6-yloxy]-butyl]-ethyl-amino]-ethanol,
2-[[3-[3-(4-Bromo-phenyl)-benzo[d]isothiazol-6-yloxy]-propyl]-ethyl-amino]-ethanol,
2-[[2-[3-(4-Bromo-phenyl)-benzo[d]isothiazol-6-yloxy]-ethyl]-ethyl-amino]-ethanol,
3-(4-Bromo-phenyl)-6-(4-pyrrolidin-1-yl-butoxy)-benzo[d]isothiazole,
3-(4-Bromo-phenyl)-6-(3-pyrrolidin-1-yl-propoxy)-benzo[d]isothiazole,
3-(4-Bromo-phenyl)-6-(2-pyrrolidin-1-yl-ethoxy)-benzo[d]isothiazole,
6-(4-Azetidin-1-yl-butoxy)-3-(4-bromo-phenyl)-benzo[d]isothiazole,
6-(3-Azetidin-1-yl-propoxy)-3-(4-bromo-phenyl)-benzo[d]isothiazole,
6-(2-Azetidin-1-yl-ethoxy)-3-(4-bromo-phenyl)-benzo[d]isothiazole,
2-({4-[3-(4-Bromo-phenyl)-benzo[b]thiophen-6-yloxy]-butyl}-methyl-amino)-ethanol,
{4-[3-(4-Bromo-phenyl)-benzo[b]thiophen-6-yloxy]-butyl}-(2-methoxy-ethyl)-methyl-amine,
4-{4-[3-(4-Bromo-phenyl)-benzo[b]thiophen-6-yloxy]-butyl}-morpholine,
2-({4-[3-(4-Bromo-phenyl)-benzo[b]thiophen-6-yloxy]-butyl}-ethyl-amino)-ethanol,
1-{4-[3-(4-Bromo-phenyl)-benzo[b]thiophen-6-yloxy]-butyl}-pyrrolidine,
1-{4-[3-(4-Bromo-phenyl)-benzo[b]thiophen-6-yloxy]-butyl}-azetidine,
{4-[3-(4-Bromo-phenyl)-benzo[b]thiophen-6-yloxy]-butyl}-isopropyl-methyl-amine,
{4-[3-(4-Bromo-phenyl)-benzo[b]thiophen-6-yloxy]-butyl}-diethyl-amine,
{4-[3-(4-Bromo-phenyl)-benzo[d]isothiazol-6-yloxy]-butyl}-ethyl-(2-methoxy-ethyl)-amine,
Allyl-{4-[3-(4-chloro-phenyl)-benzo[d]isothiazol-6-yloxy]-butyl}-methyl-amine,
2-({4-[3-(4-Chloro-phenyl)-benzo[d]isothiazol-6-yloxy]-butyl}-ethyl-amino)-ethanol,
6-(4-Azetidin-1-yl-butoxy)-3-(4-chloro-phenyl)-benzo[d]isothiazole,
3-(4-Chloro-phenyl)-6-(4-piperidin-1-yl-butoxy)-benzo[d]isothiazole,
{4-[3-(4-Chloro-phenyl)-benzo[d]isothiazol-6-yloxy]-butyl}-ethyl-(2-methoxy-ethyl)-amine,
Allyl-(3-[3-(4-bromo-phenyl)-1,1-dioxo-1H-11 6-benzo[d]isothiazol-6-yloxy]-propyl)-methyl-amine, Allyl-(4-[3-(4-bromo-phenyl)-1,1-dioxo-1H-1λ 6-benzo[d]isothiazol-6-yloxy]-butyl)-methyl-amine,
(3-[3-(4-Bromo-phenyl)-1,1-dioxo-1H-1λ 6-benzo[d]isothiazol-6-yloxy]-propyl)-dimethyl-amine,
(4-[3-(4-Bromo-phenyl)-1,1-dioxo-1H-1λ 6-benzo[d]isothiazol-6-yloxy]-butyl)-dimethyl-amine,
6-(3-Azetidin-1-yl-propoxy)-3-(4-bromo-phenyl)-benzo[d]isothiazole 1,1-dioxide,
6-(4-Azetidin-1-yl-butoxy)-3-(4-bromo-phenyl)-benzo[d]isothiazole 1,1-dioxide,
{3-[3-(4-Bromo-phenyl)-1,1-dioxo-1H-1λ 6-benzo[d]isothiazol-6-yloxy]-propyl}-methyl-propyl-amine,
{4-[3-(4-Bromo-phenyl)-1,1-dioxo-1H-1λ 6-benzo[d]isothiazol-6-yloxy]-butyl}-methyl-propyl-amine,
2-({3-[3-(4-Bromo-phenyl)-1,1-dioxo-1H-1λ 6-benzo[d]isothiazol-6-yloxy]-propyl}-ethyl-amino)-ethanol,
2-({4-[3-(4-Bromo-phenyl)-1,1-dioxo-1H-1λ 6-benzo[d]isothiazol-6-yloxy]-butyl}-ethyl-amino)-ethanol,
{3-[3-(4-Bromo-phenyl)-1,1-dioxo-1H-1λ 6-benzo[d]isothiazol-6-yloxy]-propyl}-diethyl-amine, p0 {4-[3-(4-Bromo-phenyl)-1,1-dioxo-1H-1λ 6-benzo[d]isothiazol-6-yloxy]-butyl}-diethyl-amine,
{3-[3-(4-Bromo-phenyl)-1,1-dioxo-1H-1λ 6-benzo[d]isothiazol-6-yloxy]-propyl}-(2-methoxy-ethyl)-methyl-amine,
{4-[3-(4-Bromo-phenyl)-1,1-dioxo-1H-1λ 6-benzo[d]isothiazol-6-yloxy]-butyl}-(2-methoxy-ethyl)-methyl-amine,
2-({3-[3-(4-Bromo-phenyl)-1,1-dioxo-1H-1λ 6-benzo[d]isothiazol-6-yloxy]-propyl}-methyl-amino)-ethanol,
2-({4-[3-(4-Bromo-phenyl)-1,1-dioxo-1H-1λ 6-benzo[d]isothiazol-6-yloxy]-butyl}-methyl-amino)-ethanol,
{3-[3-(4-Bromo-phenyl)-1,1-dioxo-1H-1λ 6-benzo[d]isothiazol-6-yloxy]-propyl}-ethyl-(2-methoxy-ethyl)-amine,
{4-[3-(4-Bromo-phenyl)-1,1-dioxo-1H-1λ 6-benzo[d]isothiazol-6-yloxy]-butyl}-ethyl-(2-methoxy-ethyl)-amine,
{4-[3-(4-Chloro-phenyl)-benzo[d]isothiazol-6-yloxy]-butyl}-diethyl-amine,
{4-[3-(4-Chloro-phenyl)-benzo[d]isothiazol-6-yloxy]-butyl}-cyclopropylmethyl-methyl-amine,
{4-[3-(4-Chloro-phenyl)-benzo[d]isothiazol-6-yloxy]-butyl}-isopropyl-methyl-amine,
"3-(4-Chloro-phenyl)-6-(4-pyrrolidin-1-yl-butoxy)-benzo[d]isothiazole,
"{4-[3-(4-Chloro-phenyl)-benzo[d]isothiazol-6-yloxy]-butyl}-(2-methoxy-ethyl)-methyl-amine,
2-({4-[3-(4-Chloro-phenyl)-benzo[d]isothiazol-6-yloxy]-butyl}-methyl-amino)-ethanol,
(3R)-1-{4-[3-(4-Chloro-phenyl)-benzo[d]isothiazol-6-yloxy]-butyl}-pyrrolidin-3-ol,
2-[{3-[3-(4-Bromo-phenyl)-benzo[b]thiophen-6-yloxy]-propyl}-(2-hydroxy-ethyl)-ethanol,
{3-[3-(4-Bromo-phenyl)-benzo[b]thiophen-6-yloxy]-propyl}-bis-(2-methoxy-ethyl)-amine,
2-[{4-[3-(4-Bromo-phenyl)-benzo[b]thiophen-6-yloxy]-butyl}-(2-hydroxy-ethyl)-amino]-ethanol,
{4-[3-(4-Bromo-phenyl)-benzo[b]thiophen-6-yloxy]-butyl}-bis-(2-methoxy-ethyl)-amine,
2-[[4-[3-(4-Bromo-phenyl)-benzo[d]isothiazol-6-yloxy]-butyl]-(2-hydroxy-ethyl)-amino]-ethanol,
[4-[3-(4-Bromo-phenyl)-benzo[d]isothiazol-6-yloxy]-butyl]-bis-(2-methoxy-ethyl)-amine,
2-[[3-[3-(4-Bromo-phenyl)-benzo[d]isothiazol-6-yloxy]-propyl]-(2-hydroxy-ethyl)-amino]-ethanol,
[3-[3-(4-Bromo-phenyl)-benzo[d]isothiazol-6-yloxy]-propyl]-bis-(2-methoxy-ethyl)-amine,
[3-[3-(4-Bromo-phenyl)-benzo[d]isothiazol-6-yloxy]-propyl]-ethyl-(2-methoxy-ethyl)-amine,
3-(4-Chloro-phenyl)-6-(4-piperidin-1-yl-butoxy)-benzo[d]isothiazole 1,1-dioxide,
Allyl-{4-[3-(4-chloro-phenyl)-1,1-dioxo-1H-1λ 6-benzo[d]isothiazol-6-yloxy]-butyl}-methyl-amine,
6-(4-Azetidin-1-yl-butoxy)-3-(4-chloro-phenyl)-benzo[d]isothiazole 1,1-dioxide,
{4-[3-(4-Chloro-phenyl)-1,1-dioxo-1H-1λ 6-benzo[d]isothiazol-6-yloxy]-butyl}-ethyl-(2-methoxy-ethyl)-amine,
2-({4-[3-(4-Chloro-phenyl)-1,1-dioxo-1H-1λ 6-benzo[d]isothiazol-6-yloxy]-butyl}-ethyl-amino)-ethanol,
{4-[3-(4-Chloro-phenyl)-1,1-dioxo-1H-1λ 6-benzo[d]isothiazol-6-yloxy]-butyl}-diethyl-amine,
2-({4-[3-(4-Chloro-phenyl)-1,1-dioxo-1H-1λ 6-benzo[d]isothiazol-6-yloxy]-butyl}-methyl-amino)-ethanol,
{4-[3-(4-Chloro-phenyl)-1,1-dioxo-1H-1λ 6-benzo[d]isothiazol-6-yloxy]-butyl}-(2-methoxy-ethyl)-methyl-amine,
3-(4-Chloro-phenyl)-6-(4-pyrrolidin-1-yl-butoxy)-benzo[d]isothiazole 1,1-dioxide,
1-{4-[3-(4-Chloro-phenyl)-1H-dioxo-1H-1λ 6-benzo[d]isothiazol-6-yloxy]-butyl}-pyrrolidin-3-ol,
{4-[3-(4-Chloro-phenyl)-1,1-dioxo-1H-1λ 6-benzo[d]isothiazol-6-yloxy]-butyl}-isopropyl-methyl-amine,
{4-[3-(4-Chloro-phenyl)-1,1-dioxo-1H-1λ 6-benzo[d]isothiazol-6-yloxy]-butyl}-cyclopropylmethyl-methyl-amine,
(4-[3-(4-Bromo-phenyl)-1,1-dioxo-1H-1λ 6-benzo[d]isothiazol-6-yloxy]-butyl)-bis-(2-methoxy-ethyl)-amine,
{4-[3-(4-Bromo-phenyl)-1,1-dioxo-1H-1λ 6-benzo[d]isothiazol-6-yloxy]-butyl}-dimethyl-amine N-oxide,
{4-[3-(4-Bromo-phenyl)-1,1-dioxo-1H-1λ 6-benzo[d]isothiazol-6-yloxy]-butyl}-(2-methoxy-ethyl)-methyl-amine N-oxide,
(4-[3-(4-Bromo-phenyl)-1,1-dioxo-1H-1λ 6-benzo[d]isothiazol-6-yloxy]-butyl)-bis-(2-methoxy-ethyl)-amine N-oxide,
Allyl-{3-[3-(4-chloro-phenyl)-benzo[d]isothiazol-6-yl]-prop-2-ynyl}-methyl-amine,
2-({3-[3-(4-Chloro-phenyl)-benzo[d]isothiazol-6-yl]-prop-2-ynyl}-ethyl-amino)-ethanol,
Allyl-{5-[3-(4-bromo-phenyl)-benzo[d]isothiazol-6-yl]-pent-4-ynyl}-methyl-amine,
{5-[3-(4-Bromo-phenyl)-benzo[d]isothiazol-6-yl]-pent-4-ynyl}-dimethyl-amine,
2-({5-[3-(4-Bromo-phenyl)-benzo[d]isothiazol-6-yl]-pent-4-ynyl}-methyl-amino)-ethanol,
{5-[3-(4-Bromo-phenyl)-benzo[d]isothiazol-6-yl]-pent-4-ynyl}-(2-methoxy-ethyl)-methyl-amine,
2-({5-[3-(4-Bromo-phenyl)-benzo[d]isothiazol-6-yl]-pent-4-ynyl}-ethyl-amino)-ethanol,
6-(5-Azetidin-1-yl-pent-1-ynyl)-3-(4-bromo-phenyl)-benzo[d]isothiazole,
Diethyl-{4-[3-(4-trifluoromethyl-phenyl)-benzo[d]isothiazol-6-yloxy]-butyl}-amine,
6-(4-Piperidin-1-yl-butoxy)-3-(4-trifluoromethyl-phenyl)-benzo[d]isothiazole,
Allyl-methyl-{4-[3-(4-trifluoromethyl-phenyl)-benzo[d]isothiazol-6-yloxy]-butyl}-amine,
6-(4-Azetidin-1-yl-butoxy)-3-(4-trifluoromethyl-phenyl)-benzo[d]isothiazole,
2-(Ethyl-{4-[3-(4-trifluoromethyl-phenyl)-benzo[d]isothiazol-6-yloxy]-butyl}-amino)-ethanol,
2-((2-Hydroxy-ethyl)-{4-[3-(4-trifluoromethyl-phenyl)-benzo[d]isothiazol-6-yloxy]-butyl}-amino)-ethanol, Dimethyl-{4-[3-(4-trifluoromethyl-phenyl)-benzo[d]
  isothiazol-6-yloxy]-butyl}-amine,
2-[{3-[3-(4-Chloro-phenyl)-benzo[d]isothiazol-6-yl]-prop-
  2-ynyl}-(2-hydroxy-ethyl)-amino]-ethanol,
Allyl-{3-[3-(4-fluoro-phenyl)-benzo[b]thiophen-6-yloxy]-
  propyl}-methyl-amine,
Allyl-{4-[3-(4-fluoro-phenyl)-benzo[b]thiophen-6-yloxy]-
  butyl}-methyl-amine,
{3-[3-(4-Fluoro-phenyl)-benzo[b]thiophen-6-yloxy]-
  propyl}-dimethyl-amine,
{4-[3-(4-Fluoro-phenyl)-benzo[b]thiophen-6-yloxy]-butyl -
  dimethyl-amine,
2-({3-[3-(4-Fluoro-phenyl)-benzo[b]thiophen-6-yloxy]-
  propyl}-methyl-amino)-ethanol,
2-({4-[3-(4-Fluoro-phenyl)-benzo[b]thiophen-6-yloxy]-
  butyl}-methyl-amino)-ethanol,
{3-[3-(4-Fluoro-phenyl)-benzo[b]thiophen-6-yloxy]-
  propyl}-(2-methoxy-ethyl)-methyl-amine,
{4-[3-(4-Fluoro-phenyl)-benzo[b]thiophen-6-yloxy]-
  butyl}-(2-methoxy-ethyl)-methyl-amine,
2-(Ethyl-3-[3-(4-fluoro-phenyl)-benzo[b]thiophen-6-
  yloxy]-propyl}1-amino)-ethanol,
2-(Ethyl-4-[3-(4-fluoro-phenyl)-benzo[b]thiophen-6-
  yloxy]-butyl}1-amino)-ethanol,
Ethyl-{3-[3-(4-fluoro-phenyl)-benzo[b]thiophen-6-yloxy]-
  propyl}-(2-methoxy-ethyl)-amino, -amine,
Ethyl-{4-[3-(4-fluoro-phenyl)-benzo[b]thiophen-6-yloxy]-
  butyl}-(2-methoxy-ethyl)-amino]-amine,
2-[({3-[3-(4-Fluoro-phenyl)-benzo[b]thiophen-6-yloxy]-
  propyl}-(2-hydroxy-ethyl)-amino]-ethanol,
2-[{4-[3-(4-Fluoro-phenyl)-benzo[b]thiophen-6-yloxy]-
  butyl}-(2-hydroxy-ethyl)-amino]-ethanol,
{3-[3-(4-Fluoro-phenyl)-benzo[b]thiophen-6-yloxy]-
  propyl}-bis-(2-methoxy-ethyl)-amine,
{4-[3-(4-Fluoro-phenyl)-benzo[b]thiophen-6-yloxy]-
  butyl}-bis-(2-methoxy-ethyl)-amine,
1-{3-[3-(4-Fluoro-phenyl)-benzo[b]thiophen-6-yloxy]-
  propyl}-pyrrolidine,
1-{4-[3-(4-Fluoro-phenyl)-benzo[b]thiophen-6-yloxy]-
  butyl}-pyrrolidine,
1-{3-[3-(4-Fluoro-phenyl)-benzo[b]thiophen-6-yloxy]-
  propyl}-azetidine,
1-{4-[3-(4-Fluoro-phenyl)-benzo[b]thiophen-6-yloxy]-
  butyl}-azetidine,
Allyl-{4-[1,1-dioxo-3-(4-trifluoromethyl-phenyl)-1H-11
  6-benzo[d]isothiazol-6-yloxy]-butyl}-methyl-amine,
2-({4-[1,1-Dioxo-3-(4-trifluoromethyl-phenyl)-1H-11
  6-benzo[d]isothiazol-6-yloxy]-butyl}-ethyl-amino)-
  ethanol,
{4-[1,1-Dioxo-3-(4-trifluoromethyl-phenyl)-1H-11 6-benzo
  [d]isothiazol-6-yloxy]-butyl}-diethyl-amine,
{4-[1,1-Dioxo-3-(4-trifluoromethyl-phenyl)-1H-11 6-benzo
  [d]isothiazol-6-yloxy]-butyl}-dimethyl-amine,
6-(4-Piperidin-1-yl-butoxy)-3-(4-trifluoromethyl-phenyl)-
  benzo[d]isothiazole 1,1-dioxide,
6-(4-Azetidin-1-yl-butoxy)-3-(4-trifluoromethyl-phenyl)-
  benzo[d]isothiazole 1,1-dioxide,
2-[{4-[1,1-Dioxo-3-(4-trifluoromethyl-phenyl)-1H-11
  6-benzo[d]isothiazol-6-yloxy]-butyl}-(2-hydroxy-ethyl)-
  amino]-ethanol,
{4-[3-(4-Bromo-phenyl)-benzo[d]isothiazol-6-yloxy]-
  butyl}-(1,1-dimethyl-prop-2-ynyl)-amine,
2-{4-[3-(4-Bromo-phenyl)-benzo[d]isothiazol-6-yloxy]-
  butylamino}-ethanol,
{4-[3-(4-Bromo-phenyl)-benzo[d]isothiazol-6-yloxy]-
  butyl}-methyl-prop-2-ynyl-amine,
{4-[3-(4-Bromo-phenyl)-benzo[d]isothiazol-6-yloxy]-
  butyl}-prop-2-ynyl-amine,
6-(4-Azetidin-1-yl-but-1-ynyl)-3-(4-bromo-phenyl)-benzo
  [d]isothiazole,
2-({4-[3-(4-Bromo-phenyl)-benzo[d]isothiazol-6-yl]-but-3-
  ynyl}-methyl-amino)-ethanol,
2-({3-[3-(4-Bromo-phenyl)-benzo[d]isothiazol-6-yl]-prop-
  2-ynyl}-methyl-amino)-ethanol,
2-({3-[3-(4-Bromo-phenyl)-benzo[d]isothiazol-6-yl]-prop-
  2-ynyl}-ethyl-amino)-ethanol,
Allyl-{3-[3-(4-bromo-phenyl)-1,1-dioxo-1H-11 6-benzo[b]
  thiophen-6-yloxy]-propyl}-methyl-amine,
Allyl-{4-[3-(4-bromo-phenyl)-1,1-dioxo-1H-11 6-benzo[b]
  thiophen-6-yloxy]-butyl}-methyl-amine,
{3-[3-(4-Bromo-phenyl)-1,1-dioxo-1H-11 6-benzo[b]
  thiophen-6-yloxy]-propyl}-dimethyl-amine,
2-({3-[3-(4-Bromo-phenyl)-1,1-dioxo-1H-11 6-benzo[b]
  thiophen-6-yloxy]-propyl}-methyl-amino)-ethanol,
2-({4-[3-(4-Bromo-phenyl)-1,1-dioxo-1H-11 6-benzo[b]
  thiophen-6-yloxy]-butyl}-methyl-amino)-ethanol,
2-({3-[3-(4-Bromo-phenyl)-1,1-dioxo-1H-11 6-benzo[b]
  thiophen-6-yloxy]-propyl}-ethyl-amino)-ethanol,
2-({4-[3-(4-Bromo-phenyl)-1,1-dioxo-1H-11 6-benzo[b]
  thiophen-6-yloxy]-butyl}-ethyl-amino)-ethanol,
{3-[3-(4-Bromo-phenyl)-1,1-dioxo-1H-11 6-benzo[b]
  thiophen-6-yloxy]-propyl}-(2-methoxy-ethyl)-methyl-
  amine,
{4-[3-(4-Bromo-phenyl)-1,1-dioxo-1H-11 6-benzo[b]
  thiophen-6-yloxy]-butyl}-(2-methoxy-ethyl)-methyl-
  amine,
1-{3-[3-(4-Bromo-phenyl)-1,1-dioxo-1H-11 6-benzo[b]
  thiophen-6-yloxy]-propyl}-azetidine,
1-{4-[3-(4-Bromo-phenyl)-1,1-dioxo-1H-11 6-benzo[b]
  thiophen-6-yloxy]-butyl}-azetidine,
Allyl-methyl-{5-[3-(4-trifluoromethyl-phenyl)-benzo[d]
  isothiazol-6-yl]-pent-4-ynyl}-amine,
2-(Methyl-{5-[3-(4-trifluoromethyl-phenyl)-benzo[d]
  isothiazol-6-yl]-pent-4-ynyl}-amino)-ethanol,
6-(5-Azetidin-1-yl-pent-1-ynyl)-3-(4-trifluoromethyl-
  phenyl)-benzo[d]isothiazole,
(2-Methoxy-ethyl)-methyl-{5-[3-(4-trifluoromethyl-
  phenyl)-benzo[d]isothiazol-6-yl]-pent-4-ynyl}-amine,
Dimethyl-{5-[3-(4-trifluoromethyl-phenyl)-benzo[d]
  isothiazol-6-yl]-pent-4-ynyl}-amine,
{5-[3-(4-Chloro-phenyl)-benzo[d]isothiazol-6-yl]-pent-4-
  ynyl}-dimethyl-amine,
3-(4-Chloro-phenyl)-6-(5-piperidin-1-yl-pent-1-ynyl)-
  benzo[d]isothiazole,
6-(5-Azetidin-1-yl-pent-1-ynyl)-3-(4-chloro-phenyl)-benzo
  [d]isothiazole,
{4-[3-(4-Bromo-phenyl)-1,1-dioxo-1H-11 6-benzo[b]
  thiophen-6-yloxy]-butyl}-dimethyl-amine,
Z-2-({3-[3-(4-Chloro-phenyl)-benzo[d]isothiazol-6-yl]-
  allyl}-ethyl-amino)-ethanol acetate,
Allyl-{5-[3-(4-chloro-phenyl)-benzo[d]isothiazol-6-yl]-
  pent-4-ynyl}-methyl-amine,
{5-[3-(4-Chloro-phenyl)-benzo[d]isothiazol-6-yl]-pent-4-
  ynyl}-diethyl-amine,
2-[{5-[3-(4-Chloro-phenyl)-benzo[d]isothiazol-6-yl]-pent-
  4-ynyl}-(2-hydroxy-ethyl)-amino]-ethanol,
2-({5-[3-(4-Chloro-phenyl)-benzo[d]isothiazol-6-yl]-pent-
  4-ynyl}-ethyl-amino)-ethanol,
Allyl-methyl-{3-[3-(4-trifluoromethyl-phenyl)-benzo[d]
  isothiazol-6-yl]-prop-2-ynyl}-amine,
2-(Methyl-{3-[3-(4-trifluoromethyl-phenyl)-benzo[d]
  isothiazol-6-yl]-prop-2-ynyl}-amino)-ethanol,
2-(Ethyl-{3-[3-(4-trifluoromethyl-phenyl)-benzo[d]
  isothiazol-6-yl]-prop-2-ynyl}-amino)-ethanol,
6-(3-Azetidin-1-yl-prop-1-ynyl)-3-(4-trifluoromethyl-
  phenyl)-benzo[d]isothiazole, (2-Methoxy-ethyl)-methyl-{3-[3-(4-trifluoromethyl-phenyl)-benzo[d]isothiazol-6-yl]-prop-2-ynyl}-amine,
Dimethyl-{3-[3-(4-trifluoromethyl-phenyl)-benzo[d]isothiazol-6-yl]-prop-2-ynyl}-amine,
3-(4-Bromo-phenyl)-6-(4-piperidin-1-yl-butoxy)-benzo[d]isothiazole,
3-(4-Bromo-phenyl)-6-[4-(4-methyl-piperazin-1-yl)-butoxy]-benzo[d]isothiazole,
1-(4-(4-[3-(4-Bromo-phenyl)-benzo[d]isothiazol-6-yloxy]-butyl)-piperazin-1-yl)-ethanone,
Allyl-{4-[3-(4-bromo-phenyl)-2-methyl-benzo[b]thiophen-6-yloxy]-butyl}-methyl-amine,
{4-[3-(4-Bromo-phenyl)-2-methyl-benzo[b]thiophen-6-yloxy]-butyl}-dimethyl-amine,
2-({4-[3-(4-Bromo-phenyl)-2-methyl-benzo[b]thiophen-6-yloxy]-butyl}-ethyl-amino)-ethanol,
{4-[3-(4-Bromo-phenyl)-2-methyl-benzo[b]thiophen-6-yloxy]-butyl}-diethyl-amine,
1-{4-[3-(4-Bromo-phenyl)-2-methyl-benzo[b]thiophen-6-yloxy]-butyl}-piperidine,
1-{4-[3-(4-Bromo-phenyl)-2-methyl-benzo[b]thiophen-6-yloxy]-butyl}-azetidine,
2-[{4-[3-(4-Bromo-phenyl)-2-methyl-benzo[b]thiophen-6-yloxy]-butyl}-(2-hydroxy-ethyl)-amino]-ethanol,
{4-[3-(4-Bromo-phenyl)-benzo[d]isothiazol-6-yl]-but-3-ynyl}-(2-methoxy-ethyl)-methyl-amine,
{4-[3-(4-Bromo-phenyl)-benzo[d]isothiazol-6-yl]-but-3-ynyl}-dimethyl-amine,
Allyl-{4-[3-(4-bromo-phenyl)-benzo[d]isothiazol-6-yl]-but-3-ynyl}-methyl-amine,
2-({4-[3-(4-Bromo-phenyl)-benzo[d]isothiazol-6-yl]-but-3-ynyl}-ethyl-amino)-ethanol,
2-(Ethyl-{5-[3-(4-trifluoromethyl-phenyl)-benzo[d]isothiazol-6-yl]-pent-4-ynyl}-amino)-ethanol,
2-({4-[3-(4-Chloro-phenyl)-benzo[d]isothiazol-6-yl]-but-3-ynyl}-ethyl-amino)-ethanol,
{4-[3-(4-Chloro-phenyl)-1,1-dioxo-1H-11 6-benzo[d]isothiazol-6-yloxy]-butyl}-methyl-propyl-amine,
{3-[3-(4-Chloro-phenyl)-benzo[d]isothiazol-6-yl]-prop-2-ynyl}-dimethyl-amine,
{3-[3-(4-Chloro-phenyl)-benzo[d]isothiazol-6-yl]-propyl}-dimethyl-amine,
2-(Ethyl-{3-[3-(4-trifluoromethyl-phenyl)-benzo[d]isothiazol-6-yl]-propyl}-amino)-ethanol,
Dimethyl-{3-[3-(4-trifluoromethyl-phenyl)-benzo[disothiazol-6-yl]-propyl}-amine,
2-(Methyl-{3-[3-(4-trifluoromethyl-phenyl)-benzo[d]isothiazol-6-yl]-propyl}-amino)-ethanol,
Allyl-{4-[3-(4-bromo-phenyl)-2-methyl-1,1-dioxo-1H-11 6-benzo[b]thiophen-6-yloxy]-butyl}-methyl-amine,
{4-[3-(4-Bromo-phenyl)-2-methyl-1,1-dioxo-1H-11 6-benzo[b]thiophen-6-yloxy]-butyl}-diethyl-amine,
{4-[3-(4-Bromo-phenyl)-2-methyl-1,1-dioxo-1H-11 6-benzo[b]thiophen-6-yloxy]-butyl}-methyl-propyl-amine,
2-[{4-[3-(4-Bromo-phenyl)-2-methyl-1,1-dioxo-1H-11 6-benzo[b]thiophen-6-yloxy]-butyl}-(2-hydroxy-ethyl)-amino]-ethanol,
2-({4-[3-(4-Bromo-phenyl)-2-methyl-1,1-dioxo-1H-11 6-benzo[b]thiophen-6-yloxy]-butyl}-ethyl-amino)-ethanol,
{4-[3-(4-Bromo-phenyl)-2-methyl-1,1-dioxo-1H-11 6-benzo[b]thiophen-6-yloxy]-butyl}-ethyl-(2-methoxy-ethyl)-amine,
1-{4-[3-(4-Bromo-phenyl)-2-methyl-1,1-dioxo-1H-11 6-benzo[b]thiophen-6-yloxy]-butyl}-azetidine,
Dimethyl-{4-[3-(4-trifluoromethyl-phenyl)-benzo[d]isothiazol-6-yl]-but-3-ynyl}-amine,
Allyl-methyl-{4-[3-(4-trifluoromethyl-phenyl)-benzo[d]isothiazol-6-yl]-but-3-ynyl}-amine,
2-(Ethyl-{4-[3-(4-trifluoromethyl-phenyl)-benzo[d]isothiazol-6-yl]-but-3-ynyl}-amino)-ethanol,
2-(Methyl-{4-[3-(4-trifluoromethyl-phenyl)-benzo[d]isothiazol-6-yl]-but-3-ynyl}-amino)-ethanol,
Allyl-{4-[3-(4-chloro-phenyl)-benzo[d]isothiazol-6-yl]-butyl}-methyl-amine,
{4-[3-(4-Chloro-phenyl)-benzo[d]isothiazol-6-yl]-butyl}-diethyl-amine,
{4-[3-(4-Chloro-phenyl)-benzo[d]isothiazol-6-yl]-butyl}-methyl-propyl-amine,
2-[{4-[3-(4-Chloro-phenyl)-benzo[d]isothiazol-6-yl]-butyl}-(2-hydroxy-ethyl)-amino]-ethanol,
2-({4-[3-(4-Chloro-phenyl)-benzo[d]isothiazol-6-yl]-butyl}-ethyl-amino)-ethanol,
{4-[3-(4-Chloro-phenyl)-benzo[d]isothiazol-6-yl]-butyl}-ethyl-(2-methoxy-ethyl)-amine,
6-(4-Azetidin-1-yl-butyl)-3-(4-chloro-phenyl)-benzo[d]isothiazole,
(2-Methoxy-ethyl)-methyl-{4-[3-(4-trifluoromethyl-phenyl)-benzo[d]isothiazol-6-yl]-but-3-ynyl}-amine,
2-(Ethyl-{4-[3-(4-trifluoromethyl-phenyl)-benzo[d]isothiazol-6-yl]-butyl}-amino)-ethanol,
Dimethyl-{4-[3-(4-trifluoromethyl-phenyl)-benzo[d]isothiazol-6-yl]-butyl}-amine,
2-(Methyl-{4-[3-(4-trifluoromethyl-phenyl)-benzo[d]isothiazol-6-yl]-butyl}-amino)-ethanol,
2-({3-[3-(4-Chloro-phenyl)-benzo[d]isothiazol-6-yl]-propyl}-ethyl-amino)-ethanol, and pharmaceutically acceptable salts and/or pharmaceutically acceptable esters thereof.

Other preferred compounds of general formula (I) are those selected from the group consisting of 2-({5-[3-(4-Fluoro-phenyl)-benzo[b]thiophen-6-yl]-pent-4-ynyl}-methyl-amino)-ethanol,
2-(Ethyl-{5-[3-(4-fluoro-phenyl)-benzo[b]thiophen-6-yl]-pent-4-ynyl}-amino)-ethanol,
{5-[3-(4-Fluoro-phenyl)-benzo[b]thiophen-6-yl]-pent-4-ynyl}-dimethyl-amine,
Allyl-{5-[3-(4-fluoro-phenyl)-benzo[b]thiophen-6-yl]-pent-4-ynyl}-methyl-amine,
Ethyl-{5-[3-(4-fluoro-phenyl)-benzo[b]thiophen-6-yl]-pent-4-ynyl}-(2-methoxy-ethyl)-amine,
{5-[3-(4-Fluoro-phenyl)-benzo[b]thiophen-6-yl]-pent-4-ynyl}-(2-methoxy-ethyl)-methyl-amine,
2-(Ethyl-{4-[3-(4-ethynyl-phenyl)-benzo[d]isothiazol-6-yloxy]-butyl}-amino)-ethanol,
2-(Ethyl-{4-[3-(4-ethyl-phenyl)-benzo[d]isothiazol-6-yloxy]-butyl}-amino)-ethanol,
2-((3-[3-(4-Bromo-phenyl)-benzo[d]isothiazol-6-yl]-1,1-dimethyl-prop-2-ynyl)-ethyl-amino)-ethanol,
2-({4-[3-(4-Bromo-phenyl)-benzo[d]isothiazol-6-yloxy]-butyl}-ethyl-amino)-ethanol N-oxide,
2-(Ethyl-{4-[3-(4-piperidin-1-yl-phenyl)-benzo[d]isothiazol-6-yloxy]-butyl}-amino)-ethanol,
2-(Ethyl-{4-[3-(4-morpholin-4-yl-phenyl)-benzo[d]isothiazol-6-yloxy]-butyl}-amino)-ethanol,
2-[Ethyl-(4-{3-[4-(methyl-phenyl-amino)-phenyl]-benzo[d]isothiazol-6-yloxy}-butyl)-amino]-ethanol,
Allyl-{4-[3-(4-bromo-phenyl)-benzo[d]isothiazol-6-yl]-butyl}-methyl-amine,
{4-[3-(4-Bromo-phenyl)-benzo[d]isothiazol-6-yl]-butyl}-dimethyl-amine,
2-({4-[3-(4-Bromo-phenyl)-benzo[d]isothiazol-6-yl]-butyl}-methyl-amino)-ethanol, 2-({4-[3-(4-Bromo-phenyl)-benzo[d]isothiazol-6-yl]-butyl}-ethyl-amino)-ethanol,
{4-[3-(4-Bromo-phenyl)-benzo[d]isothiazol-6-yl]-butyl}-ethyl-(2-methoxy-ethyl)-amine,
{4-[3-(4-Bromo-phenyl)-benzo[d]isothiazol-6-yl]-butyl}-(2-methoxy-ethyl)-methyl-amine,
2-{Ethyl-[4-(3-phenyl-benzo[d]isothiazol-6-yloxy)-butyl]-amino}-ethanol,
2-(Ethyl-{4-[3-(4-piperazin-1-yl-phenyl)-benzo[d]isothiazol-6-yloxy]-butyl}-amino)-ethanol,
1-{4-[4-(6-{4-[Ethyl-(2-hydroxy-ethyl)-amino]-butoxy}-benzo[d]isothiazol-3-yl)-phenyl]-piperazin-1-yl}-ethanone,
2-({4-[3-(4-Benzylamino-phenyl)-benzo[d]isothiazol-6-yloxy]-butyl}-ethyl-amino)-ethanol,
2-({4-[3-(4-Fluoro-phenyl)-benzo[d]isothiazol-6-yloxy]-butyl}-methyl-amino)-ethanol,
{4-[3-(4-Fluoro-phenyl)-benzo[d]isothiazol-6-yloxy]-butyl}-(2-methoxy-ethyl)-methyl-amine,
Ethyl-{4-[3-(4-fluoro-phenyl)-benzo[d]isothiazol-6-yloxy]-butyl}-(2-methoxy-ethyl)-amine,
2-(Ethyl-{4-[3-(4-fluoro-phenyl)-benzo[d]isothiazol-6-yloxy]-butyl}-amino)-ethanol,
2-{3-[3-(4-Bromo-phenyl)-benzo[d]isothiazol-6-yloxy]-propylamino}-ethanol,
3-[3-(4-Bromo-phenyl)-benzo[d]isothiazol-6-yloxy]-propyl}-methyl-prop-2-ynyl-amine,
{3-[3-(4-Bromo-phenyl)-benzo[d]isothiazol-6-yloxy]-propyl}-prop-2-ynyl-amine,
3-(4-Bromo-phenyl)-6-(3-piperidin-1-yl-propoxy)-benzo[d]isothiazole,
3-(4-Bromo-phenyl)-6-[3-(4-methyl-piperazin-1-yl)-propoxy]-benzo[d]isothiazole,
1-(4-{3-[3-(4-Bromo-phenyl)-benzo[d]isothiazol-6-yloxy]-propyl}-piperazin-1-yl)-ethanone,
2-({4-[3-(4-Amino-phenyl)-benzo[d]isothiazol-6-yloxy]-butyl}-ethyl-amino)-ethanol,
Allyl-{1,1-dimethyl-3-[3-(4-trifluoromethyl-phenyl)-benzo[d]isothiazol-6-yl]-prop-2-ynyl}-methyl-amine,
2-((1,1-Dimethyl-3-[3-(4-trifluoromethyl-phenyl)-benzo[d]isothiazol-6-yl]-prop-2-ynyl)-ethyl-amino)-ethanol,
{1,1-Dimethyl-3-[3-(4-trifluoromethyl-phenyl)-benzo[d]isothiazol-6-yl]-prop-2-ynyl}-(2-methoxy-ethyl)-methyl-amine,
{1,1-Dimethyl-3-[3-(4-trifluoromethyl-phenyl)-benzo[d]isothiazol-6-yl]-prop-2-ynyl}-ethyl-(2-methoxy-ethyl)-amine,
2-(Ethyl-{1-[3-(4-trifluoromethyl-phenyl)-benzo[d]isothiazol-6-ylethynyl]-cyclohexyl}-amino)-ethanol,
{4-[3-(4-Bromo-phenyl)-benzo[d]isothiazol-6-yloxy]-butyl}-ethyl-(2-fluoro-ethyl)-amine,
Ethyl-(2-fluoro-ethyl)-{4-[3-(4-trifluoromethyl-phenyl)-benzo[d]isothiazol-6-yloxy]-butyl}-amine,
2-[(4-{3-[4-(3-Dimethylamino-prop-1-ynyl)-phenyl]-benzo[d]isothiazol-6-yloxy}-butyl)-ethyl-amino]-ethanol,
3-[4-(6-{4-[Ethyl-(2-hydroxy-ethyl)-amino]-butoxy}-benzo[d]isothiazol-3-yl)-phenyl]-prop-2-yn-1-ol,
2-[Ethyl-(4-{3-[4-(3-methylamino-prop-1-ynyl)-phenyl]-benzo[d]isothiazol-6-yloxy}-butyl)-amino]-ethanol,
2-(Ethyl-{1-methyl-3-[3-(4-trifluoromethyl-phenyl)-benzo[d]isothiazol-6-yl]-prop-2-ynyl}-amino)-ethanol,
(2-Methoxy-ethyl)-methyl-{1-methyl-3-[3-(4-trifluoromethyl-phenyl)-benzo[d]isothiazol-6-yl]-prop-2-ynyl}-amine,
Ethyl-(2-methoxy-ethyl)-{1-methyl-3-[3-(4-trifluoromethyl-phenyl)-benzo[d]isothiazol-6-yl]-prop-2-ynyl}-amine,
Allyl-methyl-{1-[3-(4-trifluoromethyl-phenyl)-benzo[d]isothiazol-6-ylethynyl]-cyclopentyl}-amine,
{4-[3-(4-Bromo-phenyl)-benzo[d]isothiazol-6-yloxy]-butyl}-ethyl-amine,
{3-[3-(4-Bromo-phenyl)-benzo[d]isothiazol-6-yloxy]-propyl}-ethyl-amine,
2-{Ethyl-[4-(3-methyl-benzo[d]isothiazol-6-yloxy)-butyl]-amino}-ethanol,
Ethyl-(2-methoxy-ethyl)-[4-(3-methyl-benzo[d]isothiazol-6-yloxy)-butyl]-amine,
{2-[3-(4-Bromo-phenyl)-benzo[d]isothiazol-6-yloxy]-1,1-dimethyl-ethyl}-dimethyl-amine,
{2-[3-(4-Bromo-phenyl)-benzo[d]isothiazol-6-yloxy]-1-methyl-ethyl}-dimethyl-amine,
1-{4-[2-Methyl-3-(4-trifluoromethyl-phenyl)-benzo[b]thiophen-6-yloxy]-butyl}-piperidin-4-ol,
{4-[2-Methyl-3-(4-trifluoromethyl-phenyl)-benzo[b]thiophen-6-yloxy]-butyl}-propyl-amine,
2-{4-[2-Methyl-3-(4-trifluoromethyl-phenyl)-benzo[b]thiophen-6-yloxy]-butylamino}-ethanol,
2-(Ethyl-{4-[2-methyl-3-(4-trifluoromethyl-phenyl)-benzo[b]thiophen-6-yloxy]-butyl}-amino)-ethanol,
Allyl-methyl-{4-[2-methyl-3-(4-trifluoromethyl-phenyl)-benzo[b]thiophen-6-yloxy]-butyl}-amine,
1-{4-[2-Methyl-3-(4-trifluoromethyl-phenyl)-benzo[b]thiophen-6-yloxy]-butyl}-piperidine,
{4-[3-(4-Bromo-phenyl)-2-methyl-benzo[b]thiophen-6-yloxy]-butyl}-ethyl-(2-methoxy-ethyl)-amine,
{4-[3-(4-Bromo-phenyl)-2-methyl-benzo[b]thiophen-6-yloxy]-butyl}-dimethyl-amine,
2-(Ethyl-{4-[2-methyl-1,1-dioxo-3-(4-trifluoromethyl-phenyl)-1H-1l 6-benzo[b]thiophen-6-yloxy]-butyl}-amino)-ethanol,
Diethyl-{4-[2-methyl-1,1-dioxo-3-(4-trifluoromethyl-phenyl)-1H-1l 6-benzo[b]thiophen-6-yloxy]-butyl}-amine,
Methyl-{4-[2-methyl-1,1-dioxo-3-(4-trifluoromethyl-phenyl)-1H-1l 6-benzo[b]thiophen-6-yloxy]-butyl}-propyl-amine,
Ethyl-(2-methoxy-ethyl)-{4-[2-methyl-1,1-dioxo-3-(4-trifluoromethyl-phenyl)-1H-1l 6-benzo[b]thiophen-6-yloxy]-butyl}-amine,
2-((2-Hydroxy-ethyl)-{4-[2-methyl-1,1-dioxo-3-(4-trifluoromethyl-phenyl)-1H-1l 6-benzo[b]thiophen-6-yloxy]-butyl}-amino)-ethanol,
Methyl-{3-[2-methyl-3-(4-trifluoromethyl-phenyl)-benzo[b]thiophen-6-yl]-prop-2-ynyl}-propyl-amine,
2-(Ethyl-{3-[2-methyl-3-(4-trifluoromethyl-phenyl)-benzo[b]thiophen-6-yl]-prop-2-ynyl}-amino)-ethanol,
Diethyl-{3-[2-methyl-3-(4-trifluoromethyl-phenyl)-benzo[b]thiophen-6-yl]-prop-2-ynyl}-amine,
Allyl-methyl-{3-[2-methyl-3-(4-trifluoromethyl-phenyl)-benzo[b]thiophen-6-yl]-prop-2-ynyl}-amine,
Allyl-methyl-{5-[2-methyl-3-(4-trifluoromethyl-phenyl)-benzo[b]thiophen-6-yl]-pent-4-ynyl}-amine,
Methyl-{5-[2-methyl-3-(4-trifluoromethyl-phenyl)-benzo[b]thiophen-6-yl]-pent-4-ynyl}-propyl-amine,
2-(Ethyl-{5-[2-methyl-3-(4-trifluoromethyl-phenyl)-benzo[b]thiophen-6-yl]-pent-4-ynyl}-amino)-ethanol,
Diethyl-{5-[2-methyl-3-(4-trifluoromethyl-phenyl)-benzo[b]thiophen-6-yl]-pent-4-ynyl}-amine,
1-{3-[2-Methyl-3-(4-trifluoromethyl-phenyl)-benzo[b]thiophen-6-yl]-propyl}-azetidine,
1-{3-[2-Methyl-3-(4-trifluoromethyl-phenyl)-benzo[b]thiophen-6-yl]-propyl}-piperidin-4-ol,
1-{3-[2-Methyl-3-(4-trifluoromethyl-phenyl)-benzo[b]thiophen-6-yl]-propyl}-piperidine, 1-{3-[2-Methyl-3-(4-trifluoromethyl-phenyl)-benzo[b]thiophen-6-yl]-propyl}-pyrrolidine,
2-(Ethyl-{3-[2-methyl-3-(4-trifluoromethyl-phenyl)-benzo[b]thiophen-6-yl]-propyl}-amino)-ethanol,
Allyl-methyl-{3-[2-methyl-3-(4-trifluoromethyl-phenyl)-benzo[b]thiophen-6-yl]-propyl}-amine,
Allyl-methyl-{4-[2-methyl-3-(4-trifluoromethyl-phenyl)-benzo[b]thiophen-6-yl]-butyl}-amine,
2-(Ethyl-{4-[2-methyl-3-(4-trifluoromethyl-phenyl)-benzo[b]thiophen-6-yl]-butyl}-amino)-ethanol,
2-{4-[2-Methyl-3-(4-trifluoromethyl-phenyl)-benzo[b]thiophen-6-yl]-butylamino}-ethanol,
1-{4-[2-Methyl-3-(4-trifluoromethyl-phenyl)-benzo[b]thiophen-6-yl]-butyl}-piperidine,
1-{4-[2-Methyl-3-(4-trifluoromethyl-phenyl)-benzo[b]thiophen-6-yl]-butyl}-piperidin-4-ol,
{4-[2-Methyl-3-(4-trifluoromethyl-phenyl)-benzo[b]thiophen-6-yl]-butyl}-propyl-amine,
2-(Ethyl-{3-[2-methyl-1,1-dioxo-3-(4-trifluoromethyl-phenyl)-1H-11 6-benzo[b]thiophen-6-yl]-propyl}-amino)-ethanol,
2-{3-[2-Methyl-1,1-dioxo-3-(4-trifluoromethyl-phenyl)-1H-11 6-benzo[b]thiophen-6-yl]-propylamino}-ethanol,
{3-[2-Methyl-1,1-dioxo-3-(4-trifluoromethyl-phenyl)-1H-11 6-benzo[b]thiophen-6-yl]-propyl}-propyl-amine,
1-{3-[2-Methyl-1,1-dioxo-3-(4-trifluoromethyl-phenyl)-1H-11 6-benzo[b]thiophen-6-yl]-propyl}-piperidin-4-ol,
1-{3-[2-Methyl-1,1-dioxo-3-(4-trifluoromethyl-phenyl)-1H-11 6-benzo[b]thiophen-6-yl]-propyl}-piperidine,
Allyl-methyl-{3-[2-methyl-1,1-dioxo-3-(4-trifluoromethyl-phenyl)-1H-11 6-benzo[b]thiophen-6-yl]-propyl}-amine,
2-(Ethyl-{4-[2-methyl-1,1-dioxo-3-(4-trifluoromethyl-phenyl)-1H-11 6-benzo[b]thiophen-6-yl]-butyl}-amino)-ethanol,
Allyl-methyl-{4-[2-methyl-1,1-dioxo-3-(4-trifluoromethyl-phenyl)-1H-11 6-benzo[b]thiophen-6-yl]-butyl}-amine,
1-{4-[2-Methyl-1,1-dioxo-3-(4-trifluoromethyl-phenyl)-1H-11 6-benzo[b]thiophen-6-yl]-butyl}-piperidine,
1-{4-[2-Methyl-1,1-dioxo-3-(4-trifluoromethyl-phenyl)-1H-11 6-benzo[b]thiophen-6-yl]-butyl}-piperidin-4-ol,
{4-[2-Methyl-1,1-dioxo-3-(4-trifluoromethyl-phenyl)-1H-11 6-benzo[b]thiophen-6-yl]-butyl}-propyl-amine,
2-{4-[2-Methyl-1,1-dioxo-3-(4-trifluoromethyl-phenyl)-1H-11 6-benzo[b]thiophen-6-yl]-butylamino}-ethanol,
2-(Ethyl-{5-[2-methyl-1,1-dioxo-3-(4-trifluoromethyl-phenyl)-1H-11 6-benzo[b]thiophen-6-yl]-pent-4-ynyl}-amino)-ethanol,
Methyl-{5-[2-methyl-1,1-dioxo-3-(4-trifluoromethyl-phenyl)-1H-11 6-benzo[b]thiophen-6-yl]-pent-4-ynyl}-propyl-amine,
Allyl-methyl-{5-[2-methyl-1,1-dioxo-3-(4-trifluoromethyl-phenyl)-1H-11 6-benzo[b]thiophen-6-yl]-pent-4-ynyl}-amine,
Diethyl-{5-[2-methyl-1,1-dioxo-3-(4-trifluoromethyl-phenyl)-1H-11 6-benzo[b]thiophen-6-yl]-pent-4-ynyl}-amine,
Methyl-{2-[2-methyl-3-(4-trifluoromethyl-phenyl)-benzo[b]thiophen-6-yloxy]-ethyl}-amine,
{4-[3-(4-Bromo-phenyl)-2-methyl-benzo[b]thiophen-6-yloxy]-butyl}-methyl-amine,
Methyl-(2-methyl-pyrimidin-4-yl)-{2-[2-methyl-3-(4-trifluoromethyl-phenyl)-benzo[b]thiophen-6-yloxy]-ethyl}-amine,
Methyl-{2-[2-methyl-3-(4-trifluoromethyl-phenyl)-benzo[b]thiophen-6-yloxy]-ethyl}-pyrimidin-4-yl-amine,
(2-Methyl-pyrimidin-4-yl)-{2-[2-methyl-3-(4-trifluoromethyl-phenyl)-benzo[b]thiophen-6-yloxy]-ethyl}-amine,
{2-[2-Methyl-3-(4-trifluoromethyl-phenyl)-benzo[b]thiophen-6-yloxy]-ethyl}-pyrimidin-4-yl-amine,
{4-[3-(4-Bromo-phenyl)-2-methyl-benzo[b]thiophen-6-yloxy]-butyl}-methyl-(2-methyl-pyrimidin-4-yl)-amine,
{4-[3-(4-Bromo-phenyl)-2-methyl-benzo[b]thiophen-6-yloxy]-butyl}-methyl-pyrimidin-4-yl-amine,
{4-[3-(4-Bromo-phenyl)-2-methyl-benzo[b]thiophen-6-yloxy]-butyl}-(2-methyl-pyrimidin-4-yl)-amine,
{4-[3-(4-Bromo-phenyl)-2-methyl-benzo[b]thiophen-6-yloxy]-butyl}-pyrimidin-4-yl-amine,
{4-[3-(4-Bromo-phenyl)-2-methyl-benzo[b]thiophen-6-yloxy]-butyl}-methyl-pyridin-4-yl-amine,
1-{4-[3-(4-Bromo-phenyl)-2-methyl-benzo[b]thiophen-6-yloxy]-butyl}-1H-imidazole, and
1-{2-[2-Methyl-3-(4-trifluoromethyl-phenyl)-benzo[b]thiophen-6-yloxy]-ethyl}-1H-imidazole, and pharmaceutically acceptable salts and/or pharmaceutically acceptable esters thereof.

Particularly preferred compounds of general formula (I) are those selected from the group consisting of 2-({5-[3-(4-Bromo-phenyl)-benzo[d]isothiazol-6-yl]-pent-4-ynyl}-ethyl-amino)-ethanol, 2-(Ethyl-{5-[3-(4-trifluoromethyl-phenyl)-benzo[d]isothiazol-6-yl]-pent-4-ynyl}-amino)-ethano,
2-[{4-[3-(4-Bromo-phenyl)-2-methyl-benzo[b]thiophen-6-yloxy]-butyl}-(2-hydroxy-ethyl)-amino]-ethanol,
{5-[3-(4-Bromo-phenyl)-benzo[d]isothiazol-6-yl]-pent-4-ynyl}-dimethyl-amine,
{4-[3-(4-Bromo-phenyl)-2-methyl-1,1-dioxo-1H-11 6-benzo[b]thiophen-6-yloxy]-butyl}-ethyl-(2-methoxy-ethyl)-amine,
3-(4-Bromo-phenyl)-6-[4-(4-methyl-piperazin-1-yl)-butoxy]-benzo[d]isothiazole,
{4-[3-(4-Bromo-phenyl)-2-methyl-1,1-dioxo-1H-11 6-benzo[b]thiophen-6-yloxy]-butyl}-diethyl-amine, and
Allyl-methyl-{5-[3-(4-trifluoromethyl-phenyl)-benzo[d]isothiazol-6-yl]-pent-4-ynyl}-amine, and pharmaceutically acceptable salts and/or pharmaceutically acceptable esters thereof.

Other particularly preferred compounds of general formula (I) are those selected from the group consisting of 2-[[3-[3-(4-Bromo-phenyl)-benzo[d]isothiazol-6-yloxy]-propyl]-ethyl-amino]-ethanol,
Dimethyl-{4-[3-(4-trifluoromethyl-phenyl)-benzo[d]isothiazol-6-yloxy]-butyl}-amine,
2-[[4-[3-(4-Bromo-phenyl)-benzo[d]isothiazol-6-yloxy]-butyl]-ethyl-amino]-ethanol,
6-(3-Azetidin-1-yl-prop-1-ynyl)-3-(4-trifluoromethyl-phenyl)-benzo[d]isothiazole,
2-(Ethyl-{4-[3-(4-trifluoromethyl-phenyl)-benzo[d]isothiazol-6-yloxy]-butyl}-amino)-ethanol,
2-[[4-[3-(4-Bromo-phenyl)-benzo[d]isothiazol-6-yloxy]-butyl]-(2-hydroxy-ethyl)-amino]-ethanol,
{4-[3-(4-Chloro-phenyl)-1,1-dioxo-1H-11 6-benzo[d]isothiazol-6-yloxy]-butyl}-cyclopropylmethyl-methyl-amine, and
Dimethyl-{5-[3-(4-trifluoromethyl-phenyl)-benzo[d]isothiazol-6-yl]-pent-4-ynyl}-amine, and pharmaceutically acceptable salts and/or pharmaceutically acceptable esters thereof.

Other particularly preferred compounds of general formula (I) are those selected from the group consisting of {5-[3-(4-Chloro-phenyl)-benzo[d]isothiazol-6-yl]-pent-4-ynyl}-diethyl-amine,
2-({5-[3-(4-Chloro-phenyl)-benzo[d]isothiazol-6-yl]-pent-4-ynyl}-ethyl-amino)-ethanol,
Allyl-{4-[3-(4-bromo-phenyl)-2-methyl-1,1-dioxo-1H-11 6-benzo[b]thiophen-6-yloxy]-butyl}-methyl-amine,
{4-[3-(4-Chloro-phenyl)-1,1-dioxo-1H-11 6-benzo[d]isothiazol-6-yloxy]-butyl}-methyl-propyl-amine,
2-[{4-[3-(4-Bromo-phenyl)-2-methyl-1,1-dioxo-1H-11 6-benzo[b]thiophen-6-yloxy]-butyl}-(2-hydroxy-ethyl)-amino]-ethanol,
6-(5-Azetidin-1-yl-pent-1-ynyl)-3-(4-trifluoromethyl-phenyl)-benzo[d]isothiazole, and
2-(Ethyl-{4-[3-(4-trifluoromethyl-phenyl)-benzo[d]isothiazol-6-yl]-but-3-ynyl}-amino)-ethanol, and pharmaceutically acceptable salts and/or pharmaceutically acceptable esters thereof.

Other particularly preferred compounds of general formula (I) are those selected from the group consisting of {4-[3-(4-Chloro-phenyl)-1,1-dioxo-1H-11 6-benzo[d]isothiazol-6-yloxy]-butyl}-ethyl-(2-methoxy-ethyl)-amine,
(4-[3-(4-Bromo-phenyl)-1,1-dioxo-1H-11 6-benzo[d]isothiazol-6-yloxy]-butyl)-dimethyl-amine, and
2-({4-[3-(4-Chloro-phenyl)-benzo[d]isothiazol-6-yloxy]-butyl}-methyl-amino)-ethanol, and pharmaceutically acceptable salts and/or pharmaceutically acceptable esters thereof.

Other particularly preferred compounds of general formula (I) are those selected from the group consisting of 3-(4-Bromo-phenyl)-6-(3-piperidin-1-yl-propoxy)-benzo[d]isothiazole,
2-(Ethyl-{4-[2-methyl-3-(4-trifluoromethyl-phenyl)-benzo[b]thiophen-6-yl]-butyl}-amino)-ethanol,
2-(Ethyl-{1-methyl-3-[3-(4-trifluoromethyl-phenyl)-benzo[d]isothiazol-6-yl]-prop-2-ynyl}-amino)-ethanol,
Ethyl-(2-methoxy-ethyl)-{4-[2-methyl-1,1-dioxo-3-(4-trifluoromethyl-phenyl)-1H-11 6-benzo[b]thiophen-6-yloxy]-butyl}-amine,
{4-[3-(4-Bromo-phenyl)-benzo[d]isothiazol-6-yl]-butyl}-ethyl-(2-methoxy-ethyl)-amine,
2-(Ethyl-{3-[2-methyl-3-(4-trifluoromethyl-phenyl)-benzo[b]thiophen-6-yl]-propyl}-amino)-ethanol,
2-((1,1-Dimethyl-3-[3-(4-trifluoromethyl-phenyl)-benzo[d]isothiazol-6-yl]-prop-2-ynyl)-ethyl-amino)-ethanol,
2-((3-[3-(4-Bromo-phenyl)-benzo[d]isothiazol-6-yl]-1,1-dimethyl-prop-2-ynyl)-ethyl-amino)-ethanol,
Methyl-(2-methyl-pyrimidin-4-yl)-{2-[2-methyl-3-(4-trifluoromethyl-phenyl)-benzo[b]thiophen-6-yloxy]-ethyl}-amine, and
(2-Methyl-pyrimidin-4-yl)-{2-[2-methyl-3-(4-trifluoromethyl-phenyl)-benzo[b]thiophen-6-yloxy]-ethyl}-amine, and pharmaceutically acceptable salts and/or pharmaceutically acceptable esters thereof.

Compounds of formula (I) can have one or more asymmetric carbon atoms and can exist in the form of optically pure enantiomers or as racemats. The invention embraces all of these forms.

It will be appreciated, that the compounds of general formula (I) in this invention may be derivatised at functional groups to provide derivatives which are capable of conversion back to the parent compound in vivo.

Another particularly preferred embodiment of of the present invention is compounds of formula (VII)

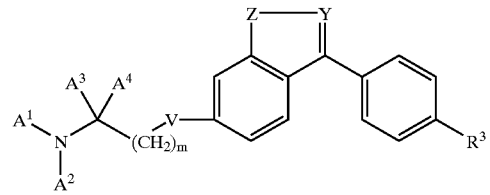

(VII)

wherein

Y N or CR$^1$,
Z is S or S(O$_2$),
V is O, CH$_2$, or C≡C,
R$^3$ is halogen or CF$_3$,
m is 1, 2 or 3,
A$^1$ is hydrogen, lower-alkyl or lower-alkoxy, and
A$^2$ is lower alkyl, lower alkoxy, lower alkyl-lower alkoxy, lower alkenyl, cycloalkyl, pyrimidine or pyrimidine-lower alkyl or
A$^1$ and A$^2$ are bonded to each other to form a lower alkyl in which one —CH$_2$— group is optionally replaced by a NR$^5$,
A$^3$ is hydrogen or lower alkyl,
A$^4$ is hydrogen or lower-alkyl,
R$^1$ is hydrogen or lower-alkyl,
R$^2$ is hydrogen or lower-alkyl, and
R$^5$ is hydrogen or lower-alkyl;

pharmaceutically acceptable salts of compounds of formula (VII); and pharmaceutically acceptable esters of compounds of formula (VII).

The present invention also relates to a process for the manufacture of compounds as described above, which process comprises reacting a compound of formula (II)

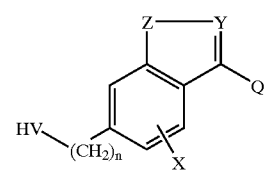

(II)

with a compound (A$^1$,A$^2$,U)N—C(A$^3$,A$^4$)—(CH$_2$)$_m$—M, wherein V is O, S or NR$^2$, M is mesylate, tosylate, triflate, Cl, Br or I, and X, Y, Z, Q, U, A$^1$, A$^2$, A$^3$, A$^4$, m, n and R$^2$ have the significances given above, or wherein HV is mesylate, tosylate, triflate, Cl, Br or I, and M is OH, SH or NHR², and R² has the significance given above,
or b) reacting a compound of formula (III)

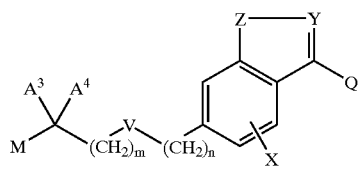
(III)

with a compound NHA¹,A², wherein M is mesylate, tosylate, triflate, Cl, Br or I, and A¹, A², A³, A⁴, V, X, Y, Z, Q, m and n are as defined above,
or c) reacting a compound of formula (IV)

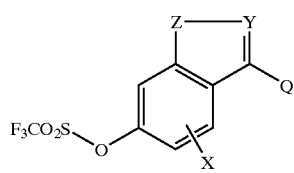
(IV)

with a compound (A¹,A²,U)N—C(A³,A⁴)—(CH₂)$_m$—C≡CH, wherein X, Y, Z, Q, U, A¹, A², A³, A⁴ and m are as defined above,
or d) reacting a compound of formula (V)

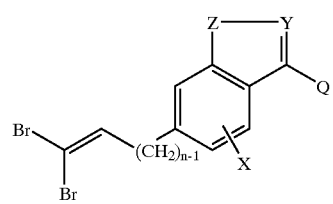
(V)

with a compound (A¹, A²,U)N—C(A³,A⁴)—(CH₂)$_m$—M, wherein M is mesylate, tosylate, Cl, Br or I, and A¹, A², A³, A⁴, U, X, Y, Z, Q, m and n are as defined above,
or e) hydrogenating a compound of formula (VI)

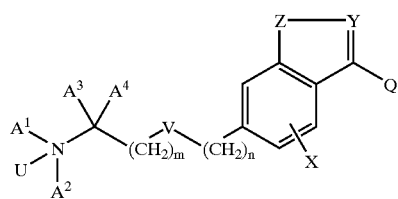
(VI)

wherein V is —C≡C—, and A¹, A², A³, A⁴, U, X, Y, Z, Q, m and n are as defined above, and optionally converting a compound of formula (I) as defined above, wherein U is a lone pair, to a corresponding compound wherein U is O.

The invention further relates to compounds of formula (I) as defined above, when manufactured according to a process as defined above.

As described above, the compounds of formula (I) of the present invention can be used for the treatment and/or prophylaxis of diseases which are associated with OSC such as hypercholesterolemia, hyperlipemia, arteriosclerosis, vascular diseases, mycoses, parasite infections and gallstones, and/or treatment and/or prophylaxis of impaired glucose tolerance, diabetes, tumors and/or hyperproliferative disorders, preferably for the treatment and/or prophylaxis of hypercholesterolemia and/or hyperlipemia. Hyperproliferative skin and vascular disorders particularly come into consideration as hyperproliferative disorders.

The invention therefore also relates to pharmaceutical compositions comprising a compound as defined above and a pharmaceutically acceptable carrier and/or adjuvant.

Further, the invention relates to compounds as defined above for use as therapeutic active substances, particularly as therapeutic active substances for the treatment and/or prophylaxis of of diseases which are associated with OSC such as hypercholesterolemia, hyperlipemia, arteriosclerosis, vascular diseases, mycoses, parasite infections, gallstones, tumors and/or hyperproliferative disorders, and/or treatment and/or prophylaxis of impaired glucose tolerance and diabetes, preferably for the treatment and/or prophylaxis of hypercholesterolemia and/or hyperlipemia.

In another embodiment, the invention relates to a method for the treatment and/or prophylaxis of diseases which are associated with OSC such as hypercholesterolemia, hyperlipemia, arteriosclerosis, vascular diseases, mycoses, parasite infections, gallstones, tumors and/or hyperproliferative disorders, and/or treatment and/or prophylaxis of impaired glucose tolerance and diabetes, preferably for the treatment and/or prophylaxis of hypercholesterolemia and/or hyperlipemia, which method comprises administering a compound as defined above to a human being or animal.

The invention further relates to the use of compounds as defined above for the treatment and/or prophylaxis of diseases which are associated with OSC such as hypercholesterolemia, hyperlipemia, arteriosclerosis, vascular diseases, mycoses, parasite infections, gallstones, tumors and/or hyperproliferative disorders, and/or treatment and/or prophylaxis of impaired glucose tolerance and diabetes, preferably for the treatment and/or prophylaxis of hypercholesterolemia and/or hyperlipemia.

In addition, the invention relates to the use of compounds as defined above for the preparation of medicaments for the treatment and/or prophylaxis of diseases which are associated with OSC such as hypercholesterolemia, hyperlipemia, arteriosclerosis, vascular diseases, mycoses, parasite infections, gallstones, tumors and/or hyperproliferative disorders, and/or treatment and/or prophylaxis of impaired glucose tolerance and diabetes, preferably for the treatment and/or prophylaxis of hypercholesterolemia and/or hyperlipemia. Such medicaments comprise a compound as defined above.

The compounds of formula (I) can be manufactured by the methods given below, by the methods given in the examples or by analogous methods. Appropriate reaction conditions for the individual reaction steps are known to the person skilled in the art. Starting materials are either commercially available or can be prepared by methods analogous to the methods given in the examples or by methods known in the art.

25
Scheme 1
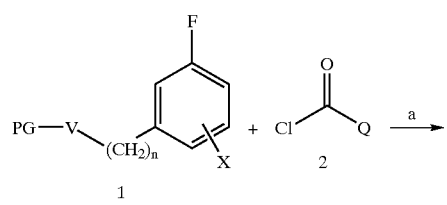
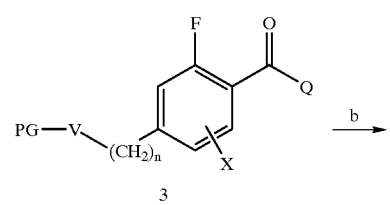
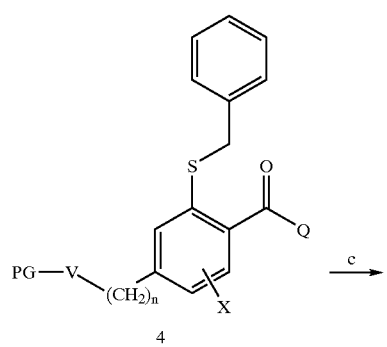
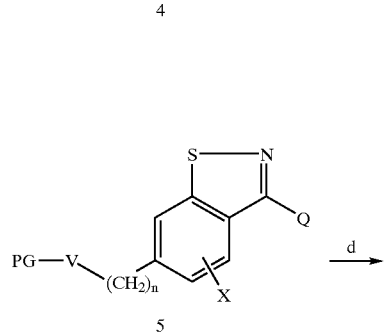
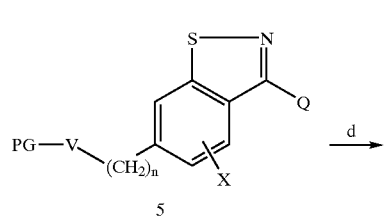
PG = protecting group
26
Scheme 2
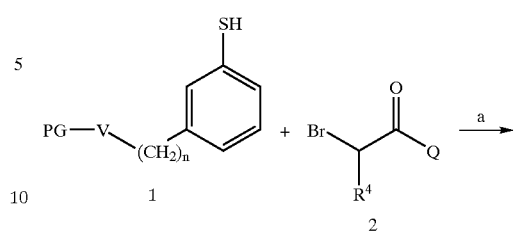
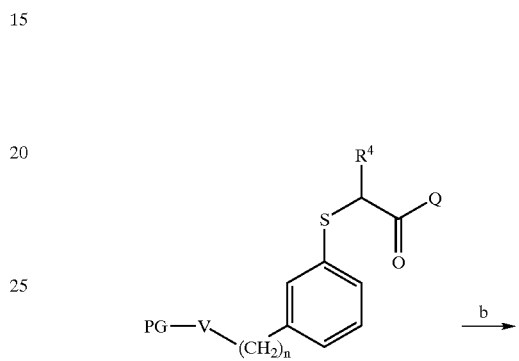
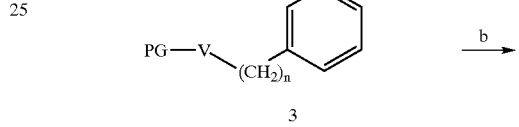
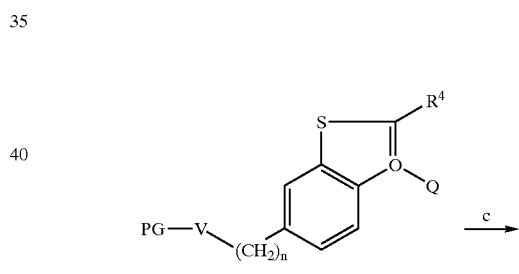
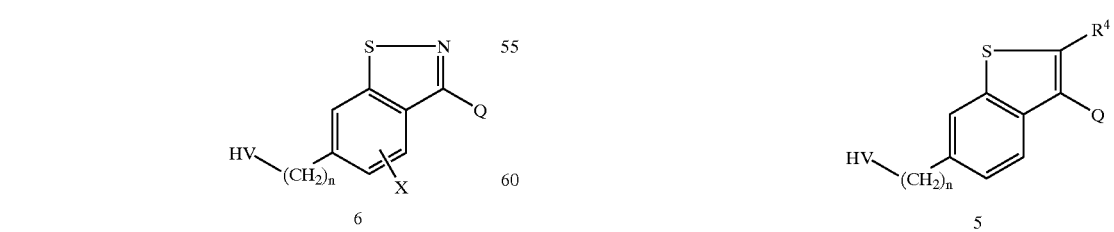
PG = protecting group Scheme 3
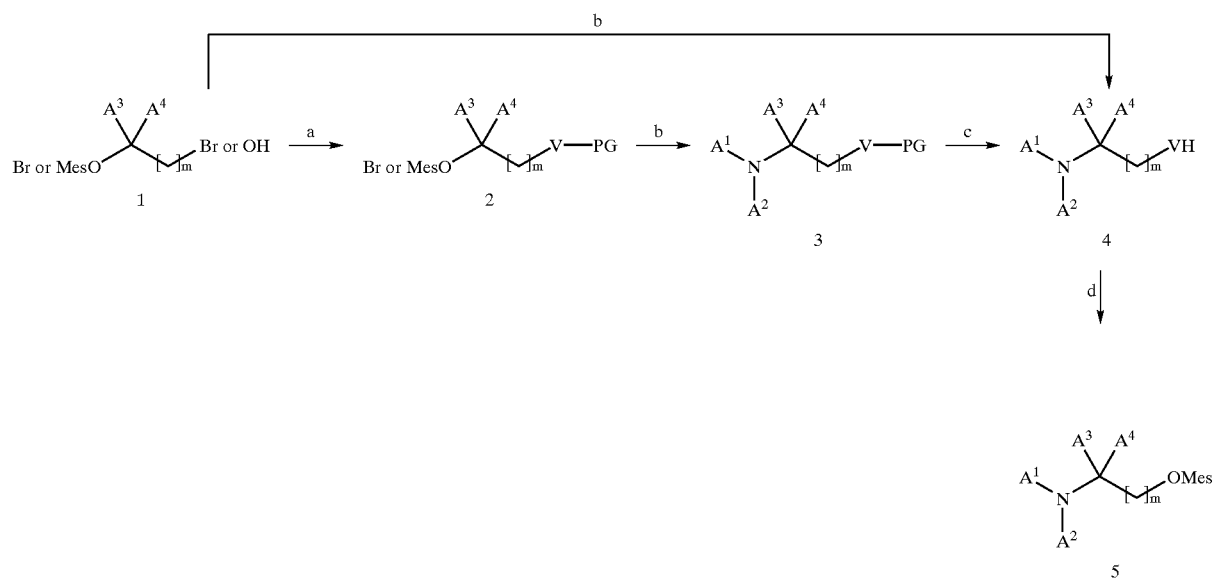
PG = protecting group, such as trityl for sulfur or BOC for NR²
Scheme 4
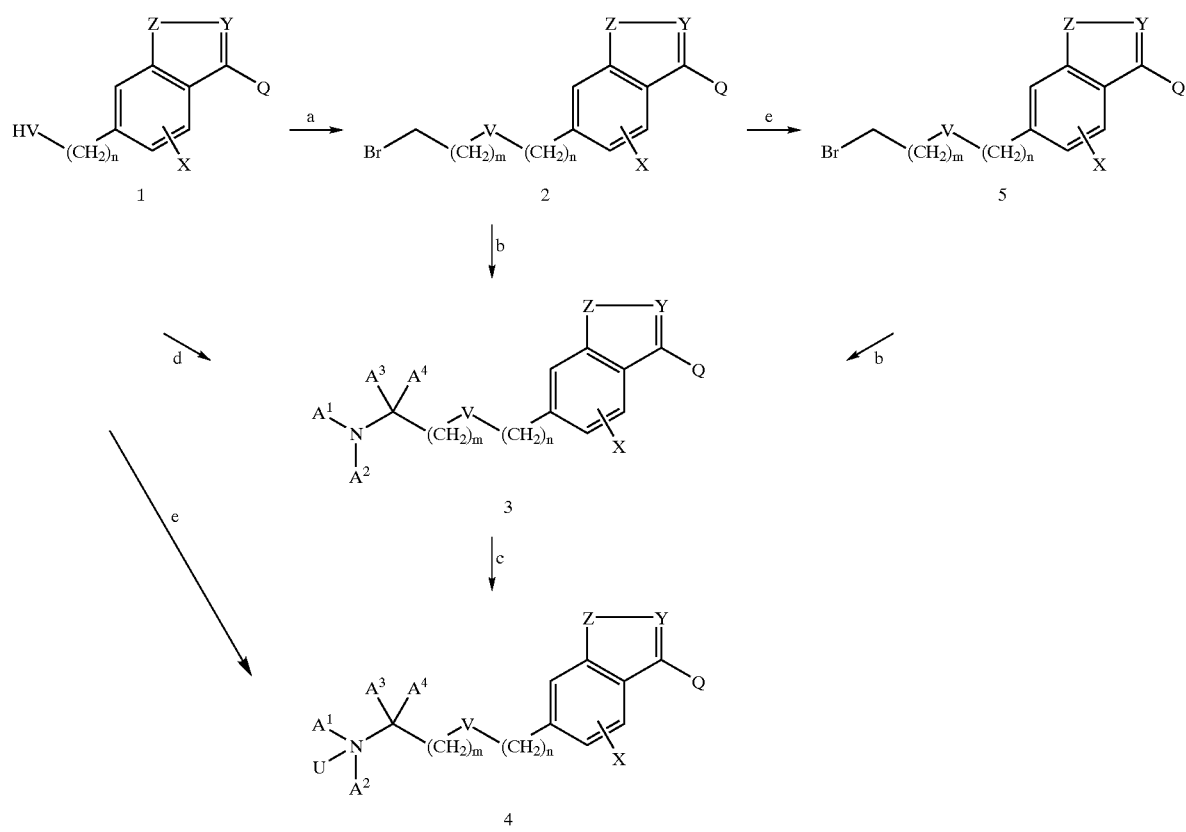

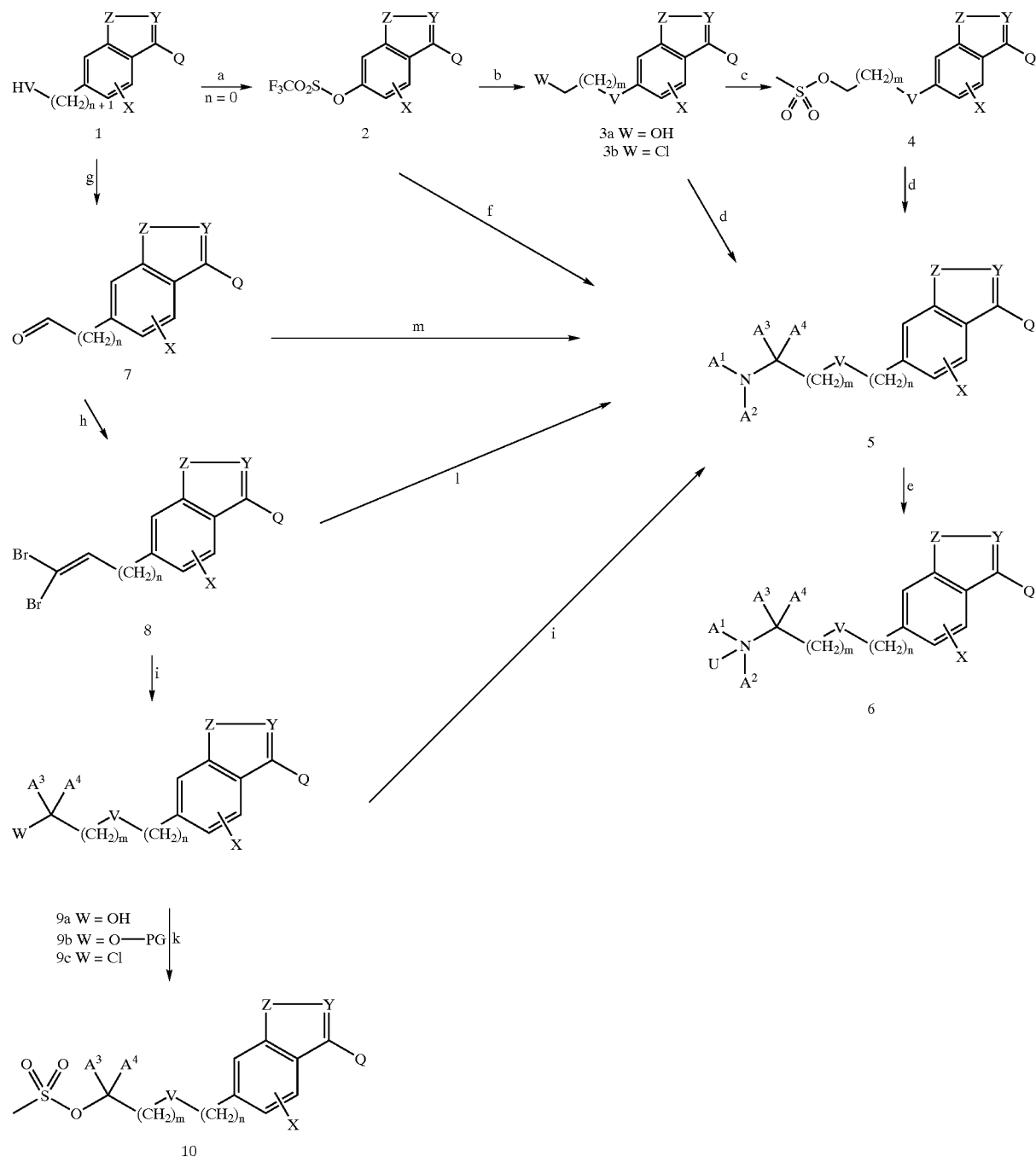

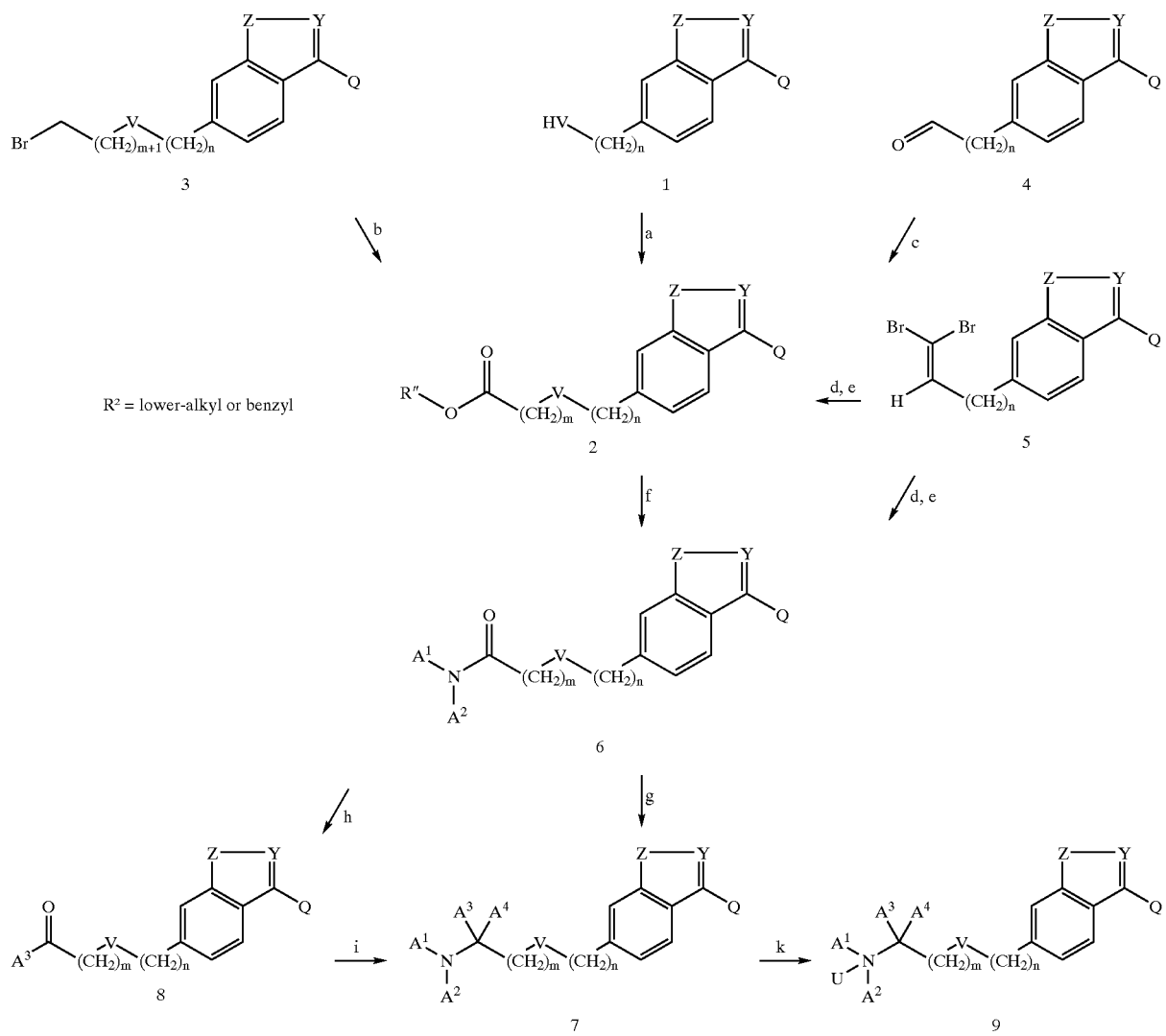

Scheme 1:

For compounds which are benzo[d]isothiazole derivatives, the synthesis starts from a suitable protected fluoro-substituted aromatic system 1 (V=O or NR², and n=0–6, or V=S and n=0) and an acid chloride 2 which is converted under Friedel-Crafts conditions with a Lewis acid such as aluminium chloride to the phenone 3 (step a). The starting materials 1 are either commercially available or can be obtained by methods known in the art, e.g. from the corresponding acids. The transformation to the heterocyclic system may be achieved by reacting the fluoride 3 with e.g. benzylmercaptane in the presence of potassium tert.butylate in THF at RT, treating the benzylthio ether 4 obtained with sulfuryl chloride in methylene chloride (at 0° C.) and cyclizing the resulting intermediate in THF with a solution of ammonia in ethanol to 5, as described in European Patent application 778271 (steps b and c). In case of methoxyphenylether 5 (n=0, V-PG=OMe) treatment with boron tribromide in methylene chloride at −78° C. to RT or with 62% aqueous HBr in acetic acid at reflux gives phenol 6. For V=NR² or V=O and n>0, deprotection using procedures known in the art (step d) gives the free HV-building block 6.

Oxidation of a suitable protected benzo[d]isothiazols 5 (V=O or NR², and n=0–6, or V=S and n=0) may be effected with e.g. KMnO₄ on silicagel in CH₂Cl₂ at 50° C. to yield the corresponding benzo[d]isothiazole 1,1-dioxide.

For V=S and n>0, the sulfur is introduced in a later step (see Scheme 4).

Scheme 2:

For compounds which are benzo[b]thiophene derivatives, the synthesis starts from a suitable protected thiol 1 and α-bromoacetophenone derivative 2 which are converted to the thioether 3 by treatment with KOH in EtOH at 0° C. to RT (step a). The starting materials 1 are either commercially available or can be obtained by methods known in the art, e.g. from the corresponding acids. The cyclization can be carried out by heating the compound 3 in polyphosphoric acid to 80–100° C. or by treatment with BF₃.Et₂O to give benzo[b]thiophene 4 (step b).

In the case of methoxyphenylether 4 (n=0, V-PG=OMe), treatment with boron tribromide in methylene chloride at -78° C. to RT or with 62% aqueous HBr in acetic acid at reflux gives phenol 5. For V=S, $NR^2$ or V=O and n>0, deprotection using procedures known in the art (step d) gives the free HV-building block 5.

Oxidation of a suitable protected benzo[b]thiophene 4 (V=O or $NR^2$, and n=0–6, or V=S and n=0) may be effected with e.g. sodium perborate in acetic acid at 50° C. yield the corresponding benzo[b]thiophene 1,1-dioxide 4.

For V=S and n>0, the sulfur is introduced in a later step (see Scheme 4). Alternatively compound of the formula 5 maybe prepared as described previously in European Patent application 778271.

Scheme 3:

Scheme 3 shows the synthesis of amino-VH sidechain 4 that may be used for the synthesis of compounds with the corresponding V-spacers (V=$NR^2$, S, or O). α,ω-dihaloalkane or mesyl-alkanyl-halogenide 1 may be treated with a suitable protected amine ($HNR^2$-PG, PG=protecting group, e.g. BOC) in DMA or a thiol (HS-PG) e.g., triphenylmethanethiol in the presence of NaH in DMA to give the compound 2 (step a). Treatment with the amine $A^1A^2$NH yields the S- or N-protected amine 3 (step b) and in the case of α,ω-haloalkanol 1 directly amino-alcohol 4. N-deprotection with procedures known in the art e.g. TFA in $CH_2Cl_2$ gives the amine side chain 4 (step c). The deprotection of the thiol moiety in 3 may be achieved with TFA/triisopropylsilane in $CH_2Cl_2$ at 0° C. to RT to yield the aminothiol 4 (step c). Aminoalkanol 4 can further be transformed to mesylate 5 (step d).

Scheme 4:

Alkylation of the phenol 1 (V=O, S, n=0) in acetone with $K_2CO_3$ and a suitable dihaloalkane (halogene is here represented by bromine, but can also be chlorine or iodine. It is also possible to use mesylates or tosylates instead of halogenides) at reflux yields halogenide 2 (reaction step a). For the preparation of derivatives 2 (V=O, n>0), the alcohol 1 can be treated with α,ω-dihaloalkanes under phase transfer conditions e.g. α,ω-dihaloalkanes, NaOH, $nBu_4NHSO_4$. For V=S, O or $NR^2$-PG, the derivative 1 may be treated with α,ω-dihaloalkane in the presence of NaH in DMF 0° C. to RT to yield bromide 2. For shorter alkanes (m=1 or 2), the method of choice is the in situ generation of the haloalkane-triflate (from the corresponding haloalkanol with trifluoromethansulfonic anhydride/2,6-di-tert-butylpyridine in $CH_2Cl_2$ at 0° C.). This haloalkane-triflate may then be reacted with 1 in the presence of a base such as with 2,6-di-tert-butylpyridine as base in nitromethane at 60° C. to yield bromide 2 [analogously to a procedure of Belostotskii, Anatoly M.; Hassner, Alfred. Synthetic methods. 41. Etherification of hydroxysteroids via triflates. Tetrahedron Lett. (1994), 35(28), 5075]. Compound 2 can be converted (reaction step b) to the amine 3 with an excess of the corresponding amine $NHA^1A^2$ in a suitable solvent such as DMA, DMF, MeOH at RT or 50–65° C. or with amine $NHA^1A^2$, sodium hydride in DMF, DMA or THF. Alternatively, the compound 1 may be transferred to the amine 3 by attaching the pre-assembled fragment $A^1A^2NC(A^3A^4)$ $(CH_2)_m$—OMes/halogenide, which can be synthesised by known methods (shown e.g in Scheme 3), using alkylating conditions (step d). Heteroaromate 1 (V=O, n>0) can also be mesylated 1 (V=OMes) and then reacted with $A^1A^2NC(A^3A^4)(CH_2)_m$—VH (synthesis described Scheme 3) in e.g. DMF with NaH as base to give 3 (with V=O, S, $NR^2$).

Amine 3 may be converted to a salt or to the N-oxide 4 (step c). For the formation of N-oxide 4 (V=O) a mixture of hydrogen peroxide urea adduct and phthalic anhydride in $CH_2Cl_2$ at RT may be used. For the preparation of the N-oxides 4 (V=S or $NR^2$) step e may be performed: Oxidation of the pre-assembled fragment $A^1A^2NC(A^3A^4)$ $(CH_2)_m$ —OMes/halogenide to the corresponding N-oxide derivative, followed by alkylation of the compound 1.

Oxidation of 2 (V=O or $NR^2$) may be effected with e.g. $KMnO_4$ on silicagel in $CH_2Cl_2$ at 50° C. for benzo[d]isothiazols to give the corresponding benzo[d]isothiazole 1,1-dioxide 5. In the case of benzo[b]thiophene 2, oxidation with sodium perborate in acetic acid at 50° C. gives benzo[b]thiophene 1,1-dioxide 5. Bromide 5 can be transformed to 3 and 4 as described for bromide 2.

If $A^2$=H, heteroaromatic moieties $A^2$ may be introduced by treatment with halo heteroaromatics in the presence of Huenig's base in DMF (Ger. Offen. (1990), DE3905364 A1). Alternatively, Buchwald conditions e.g. $Pd(OAc)_2$, 2-(Dicyclohexylphosphino) biphenyl, NaOtBu in toluene might be applied (John P. Wolfe, Hiroshi Tomori, Joseph P. Sadighi, Jingjun Yin, and Stephen L. Buchwald, J. Org. Chem., 65 (4), 1158–1174, 2000).

Amine 3 may be further modified. For Q=methyl, deprotonation with e.g. lithium diisopropylamide in THF at −78° C. and then treatment with a bromide $BrCH_2$—$R^7$ or aldehyde HC(O)—$R^7$, wherein $R^7$ is an alkyl, alkenyl or alkadienyl group with up to 12 C atoms, may yield the corresponding compound 3 in which Q stands for $CH_2CH_2$—$R^7$ or $CH_2CH(OH)$—$R^7$.

For an amine 3 or also starting compound 1 in which Q is a halo- or hydroxy-substituted aromatic system (in case of the later, the corresponding triflate may be synthesized) the corresponding alkyne, alkyl, alkene, amine, alkoxy or thioalkoxy substituted derivative can be synthesized employing Sonogashira reaction or palladium catalyzed amination, C—O or C—S coupling reactions. For the Sonogashira reaction of the arylhalogenide or aryltriflate may be treated with a suitable alkynes or alkynol in THF in the presence of a base such as triethylamine or piperidine with a catalytic amount of e.g. $Pd(PPh_3)_4$/CuI or $Pd(OAc)2$/CuI or $PdCl_2(PPh_3)_2$/CuI at 45° C. to 80°. These alkynes can then selectively be reduced. The introduction of an amine moiety may be achieved using primary or secondary amines and the arylhalogenide or aryltriflate using methods developed by Buchwald e.g. tris(Dibenzylideneacetone)dipalladium, 2(ditertbutylphosphino)Biphenyl in toluene and Natrium tert-butylat as base to give the newly substituted 3 [e.g. Wolfe, John P.; Tomori, Hiroshi; Sadighi, Joseph P.; Yin, Jingjun; Buchwald, Stephen L. Simple, efficient catalyst system for the palladium-catalyzed amination of aryl chlorides, bromides, and triflates. J. Org. Chem. (2000), 65(4), 1158–1174].

For the oxygen analogues see for example Palucki, Michael; Wolfe, John P.; Buchwald, Stephen L. Palladium-Catalyzed Intermolecular Carbon-Oxygen Bond Formation: A New Synthesis of Aryl Ethers. J. Am. Chem. Soc. (1997), 119(14), 3395–3396.

These newly substituted amines 3 can then again be transformed to compound 4. For the preparation of the N-oxides 4 (V=S or $NR^2$) step e may be performed: Oxidation of the pre-assembled fragment $A^1A^2NC(A^3A^4)$ $(CH_2)_m$—OMes/halogenide to the corresponding N-oxide derivative, followed by alkylation of the compound 1.
Scheme 5:

In Scheme 5, the preparation of compounds of formula 6, in which V represents —$CH_2$—, —CH=CH— or —C≡C— is outlined starting from hydroxyphenyl derivative 1, which may be transformed to the triflate 2 in pyridine with trifluoromethanesulfonic anhydride at 0° C. to RT (reaction step a). Sonogashira-coupling (reaction step b) of the triflate 2 and a suitable alkynol or alkynechloride in piperidine with $Pd(PPh_3)_4$/CuI at 45° C. to 80° C. in analogy to a literature procedure yields alcohol 3a or chloride 3b [Stara, Irena G.; Stary, Ivo; Kollarovic, Adrian; Teply, Filip; Saman, David; Fiedler, Pavel. Coupling reactions of halobenzenes with alkynes. The synthesis of phenylacetylenes and symmetrical or unsymmetrical 1,2-diphenylacetylenes. Collect. Czech. Chem. Commun. (1999), 64(4), 649–672.]. In case of Q=Bromo or Iodo-substituted aromatic system, triflate 2 is dissolved in THF with $PdCl_2(PPh_3)_2$ as catalyst and alkynol or alkynechloride, triphenylphosphine, triethylamine and a catalytic amount of CuI to give alkyne 3a or 3b. Mesylation for alcohol 3a with methanesulfonylchloride e.g. in pyridine with DMAP (reaction step c) and subsequent amination (reaction step d) of the resulting mesylate 4 with a suitable amine $NHA^1A^2$ in DMA at RT or as descibed in Scheme 4 yields the amine 5. Alcohol 3a can also be treated with trifluoromethane sulfonic acid anhydride and Huenig's base at −15° C. in $CH_2Cl_2$ (in situ generation of the corresponding triflate) followed by treatment with the corresponding amine $NHA^1A^2$ at −15° C. to RT. This is especially the method of choice for but-3-yn-1-ol-derivatives 3a. Chloride 3b can be transformed directly or via iodide (Finkelstein reaction) to the amine 5, as described above (step d). Compounds 5 in which V is —$CH_2$— or —CH=CH— can be obtained by hydrogenation of compound 5 in EtOH with $Pt_2O.H_2O$ (yields the saturated analogue 5) or by selective hydrogenation with other known methods (yields the double bond analogue 5). Optionally, the hydrogenation described above can be performed at an earlier stage e.g. the alcohol 3a or mesylate 4.

For compounds in which $A^3$ and/or $A^4$ are not H, the group $A^1A^2NC(A^3A^4)$ [$CH_2$]$_m$— acetylene can be synthesised by known methods and attached to compound 2 (Sonogashira-coupling), to yield the compounds of the present invention 5 (reaction step f).

Compounds of the formula 5 (n>0) may be synthesised by Swern oxidation of the alcohol 1 (V=O and n>0) to the corresponding aldehyde 7 (step g). The aldehyde 7 may be treated with triphenylphosphine, tetra-bromo-methane and triethylamine in $CH_2Cl_2$ at 0° C. to RT to yield 2,2-Dibromo-vinyl derivative 8 (step h). Rearrangement with n-BuLi (ca 1.6 M in hexane) in THF at −78° C., followed by reaction with formaldehyde (−78° C. to RT) leads to the propargyl alcohol 9a (step i, side chain extension through application of the Corey-Fuchs method), following conditions described in: Marshall, James A.; Bartley, Gary S.; Wallace, Eli M. Total Synthesis of the Pseudopterane (−)-Kallolide B, the Enantiomer of Natural (+)-Kallolide B. J. Org. Chem. (1996), 61(17), 5729–5735; and Baker, Raymond; Boyes, Alastair L.; Swain, Christopher J. Synthesis of talaromycins A, B, C, and E. J. Chem. Soc., Perkin Trans. 1 (1990), (5), 1415–21.

For longer side chains, the rearrangement is performed with n-BuLi (ca 1.6 M in hexane) in THF at −78° C. as above, followed by addition of a cosolvens such as DMPU and reaction with O-protected 1-bromo-alcohols or α-chloro-ω-iodoalkane (e.g. 1-bromo-n-tetrahydropyaranyloxyalkane) to yield the O-protected compounds 9b or the chloro compound 9c (step i). O-protected compounds 9b can be deprotected to the corresponding alkynol 9a (in MeOH at 50–60° C., in the presence of catalytic amount of pyridinium toluene-4-sulfonate). Alcohol 9a can be reacted with Huenig's base/trifluoromethane sulfonic acid anhydride at −15° C. in $CH_2Cl_2$ (in situ generation of the corresponding triflate) followed by treatment with Huenig's base and the corresponding amine $NHA^1A^2$ at −15° C. to RT to give amine 5. Alternatively, mesylation of alcohol 9a with methanesulfonylchloride, pyridine and DMAP in $CH_2Cl_2$ at 0° C. to RT gives mesylate 10. Conversion of the mesylate 10 or the chloride 9c (or the in situ generated iodide) to the amine 5 can be accomplished with an excess of the corresponding amine $NHA^1A^2$ in DMA at RT or as described above (step 1).

Optionally compounds 5 in which V is —$CH_2$— or —CH=CH— can be obtained by hydrogenation of compound 5 itself or the intermediates 9a, 9b, 9c or 10. The hydrogenation may be done in EtOH with $Pt_2O.H_2O$ (yields the saturated analogues 5, 9a, 9b, 9c or 10) or by selective hydrogenation to the double bond with other known methods and transforming the intermediates afterwards to 5.

For the introduction of the group $A^1A^2N(A^3A^4C)$ [$CH_2$]$_m$ in compound 8 to obtain the final compound 5 in which $A^3$ and/or $A^4$ are not H, the following steps have to be performed (step m or step i and l): for m>0, the building block $A^1A^2N(A^3A^4C)$ [$CH_2$]$_m$— halogenide/mesylate is synthesised by known methods (or in analogy to the methods described in Scheme 3) and introduced (step m) under the same condition as described above for step i. For m=0, the introduction of the group $A^1A^2N(A^3A^4C)$ with $A^3$ and/or $A^4$ not H, a two step procedure has to be followed: first the rearrangement of 8 with n-BuLi (ca 1.6 M in hexane) in THF at −78° C., followed by reaction with the corresponding aldehyde ($A^3$ or $A^4$—COH) or ketone ($A^3COA^4$, at −78° C. to RT) leads to the $A^3A^4$ substituted propargyl alcohol 9a (step i) which is mesylated and reacted with the desired $A^1A^2$-substituted-amine to yield $A^3A^4$-substituted compound 5 (step 1).

If $A^2$=H, heteroaromatic moieties $A^2$ may be introduced by treatment with halo heteroaromatics in the presence of Huenig's base in DMF (Ger. Offen. (1990), DE3905364 A1). Alternatively, Buchwald conditions e.g. $Pd(OAc)_2$, 2-(Dicyclohexylphosphino) biphenyl, NaOtBu in toluene might be applied (John P. Wolfe, Hiroshi Tomori, Joseph P. Sadighi, Jingjun Yin, and Stephen L. Buchwald, J. Org. Chem., 65 (4), 1158–1174, 2000).

Amine 5 can further be transformed. For Q=methyl as described in Scheme 4 to the corresponding compound 5 in which Q stands for $CH_2CH_2$—$R^7$ or $CH_2CH(OH)$—$R^7$.

For an amine 5 in which Q is a halo-substituted aromatic system, the corresponding alkyne, alkyl, alkene, amine, alkoxy or thioalkoxy substituted derivative can be synthesized employing Sonogashira reaction or palladium catalyzed amination, C—O or C—S coupling reactions (as described for compound 3 in scheme 4) (or in case of a hydroxy substitution, the corresponding triflate may be synthesized).

Amine 5 may be converted to a salt or to the N-oxide 6 using a mixture of hydrogen peroxide urea adduct and phthalic anhydride in $CH_2Cl_2$ at RT (step e).

Scheme 6:

Another approach for the introduction of the substituted side chain is depicted in scheme 6. It starts by alkylation of the phenol 1 (V=O, S, n=0) directly with a suitable ω-haloalkane carboxylic ester or via the in situ generated triflate of an ω-hydroxy alkane carboxylic ester in analogy to Belostotskii, Anatoly M.; Hassner, Alfred. Synthetic methods. 41. Etherification of hydroxysteroids via triflates. Tetrahedron Lett. (1994), 35(28), 5075–6(step a). For the preparation of derivatives 2 (V=O, n>0), the alcohol 1 can be treated with ω-haloalkane carboxylic ester (halogene is here represented by bromine, but can also be chlorine or iodine. It is also possible to use mesylates or tosylatesor triflates instead of halogenides) under phase transfer conditions. For V=S, O or $NR^2$-PG, the derivative 1 may be treated with with ω-haloalkane carboxylic ester in the presence of NaH in DMF 0° C. to RT to yield ester 2. Alternatively, the ester 2 can be prepared from the bromide 3 (synthesis according to scheme 4) by treatment with e.g. acetocyanhydrine in acetonitrile, followed by a Pinner reaction and hydrolysis of the imidate to the corresponding ester (step b).

For V=CH=CH, the ester 2 or its corresponding acid may be prepared from aldehyde 4 (synthesis described in scheme 5) by treatment with the corresponding Wittig reagent $X^-$ $Ph_3P^+$ $(CH_2)_{m+1}CO_2R/H$. For V=C, hydrogenation of the Wittig product under standard conditions yields the saturated product 2.

For V=C≡C, ester 2 or amide 6 may be derived from the dibromoderivative 5 (synthesis according to scheme 5) by rearrangement with n-BuLi (ca 1.6 M in hexane) in THF at –78 C, followed by reaction with chloroformate or dimethylcarbamoyl chloride (–78° C. to RT; step d). For longer side chains, the rearrangement of dibromoalkene 5 may be performed with n-BuLi (ca 1.6 M in hexane) in THF at –78° C. as above, followed by addition of a cosolvens such as DMPU and reaction with a suitable protected 1-bromoalkylalcohol Br—$(CH_2)_m$$CH_2OH$, followed by oxidation to yield the compound 2 as acid (step e).

Saponification of the ester 2 using standard conditions e.g. LiOH in EtOH, MeOH or THF, followed by treatment with $NHA^1A^2$, EDCI, HOBT and a base such as Huenig's base, $NEt_3$, NMM in $CH_2Cl_2$, DMF, DMA or dioxane gives amide 6. Amide 6 can be transferred to amine 7 ($A^3,A^4$=Me) by reaction with methylmagnesium bromide, $ZrCl_4$ in THF at low temperature (see Stephen M. Denton, Anthony Wood, A Modified Bouveault Reaction for the Preparation of α,α-dimethylamines from Amides, Synlett 1999,1, 55–56.) or by treatment with other grignard reagents in the presence of $ZrCl_4$ or $Ti(OiPr)_4$ (see V. Chalinski, A. de Meijere, A versatile New Preparation of Cyclopropylamines from acid dialkylamides, Angew.Chem. Int. Ed. Engl. 1996, 35, No4, 413–4.).

For $A^1$=Me, $A^2$=OMe, the amide 3 can be treated with a grignard reagent $A^3MgX$ to give the corresponding ketone 8.

Reductive alkylation of the ketone 8 by treatment with $NHA^1A^2$ in the presence of tetraisopropyl orthotitanate, followed by reduction with $NaCNBH_3$ in ethanol yields the amine 7 (see: R. J. Mattson, K. M. Pham, D. J. Leuck, K. A. Cowen, J. O. C. 1990,55,2552–4.).

Amine 7 may be converted to a salt or to the N-oxide 9 using a mixture of hydrogen peroxide urea adduct and phthalic anhydride in $CH_2Cl_2$ at RT.

Amine 7 can be transformed further. For Q=methyl as described in Scheme 4 to the corresponding compound 7 in which Q stands for $CH_2CH_2$—$R^7$ or $CH_2CH(OH)$—$R^7$.

For an amine 7 in which Q is a halo-substituted aromatic system, the corresponding alkyne, alkyl, alkene, amine, alkoxy or thioalkoxy substituted derivative can be synthesized employing Sonogashira reaction or palladium catalyzed amination, C—O or C—S coupling reactions (as described for compound 3 in scheme 4) (or in case of a hydroxy substitution, the corresponding triflate may be synthesized).

The following tests were carried out in order to determine the activity of the compounds of formula I and their salts.

Inhibition of Human Liver Microsomal 2,3-oxidosqualene-lanosterol Cyclase (OSC)

Liver microsomes from a healthy volunteer were prepared in sodium phosphate buffer (pH 7.4). The OSC activity was measured in the same buffer, which also contained 1 mM EDTA and 1 mM dithiothreitol. The microsomes were diluted to 0.8 mg/ml protein in cold phosphate buffer. Dry [$^{14}$C]R,S-monooxidosqualene (MOS, 12.8 mCi/mmol) was diluted to 20 mCi/µl with ethanol and mixed with phosphate buffer-1% BSA (bovine serum albumin). A stock solution of 1 mM test substance in DMSO was diluted to the desired concentration with phosphate buffer-1% BSA. 40 µl of microsomes were mixed with 20 µl of the solution of the test substance and the reaction was subsequently started with 20 µl of the [$^{14}$C]R,S-MOS solution. The final conditions were: 0.4 mg/ml of microsomal proteins and 30 µl of [$^{14}$C]R,S-MOS in phosphate buffer, pH 7.4, containing 0.5% albumin, DMSO<0.1% and ethanol<2%, in a total volume of 80 µl.

After 1 hour at 37° C. the reaction was stopped by the addition of 0.6 ml of 10% KOH-methanol, 0.7 ml of water and 0.1 ml of hexane:ether (1:1, v/v) which contained 25 µg of non-radioactive MOS and 25 µg of lanosterol as carriers. After shaking, 1 ml of hexane:ether (1:1, v/v) was added to each test tube, these were again shaken and then centrifuged. The upper phase was transferred into a glass test tube, the lower phase was again extracted with hexane:ether and combined with the first extract. The entire extract was evaporated to dryness with nitrogen, the residue was suspended in 50 µl of hexane:ether and applied to a silica gel plate. Chromatographic separation was effected in hexane:ether (1:1, v/v) as the eluent. The Rf values for the MOS substrate and the lanosterol product were 0.91 and, respectively, 0.54. After drying, radioactive MOS and lanosterol were observed on the silica gel plate. The ratio of MOS to lanosterol was determined from the radioactive bands in order to determine the yield of the reaction and OSC inhibition.

The test was carried out on the one hand with a constant test substance concentration of 100 nM and the percentage OSC inhibition against controls was calculated. The more preferred compounds of the present invention exhibit inhibitions larger than 50%. In addition, the test was carried out with different test substance concentrations and subsequently the $IC_{50}$ value was calculated, i.e. the concentration required to reduce the conversion of MOS into lanosterol to 50% of the control value. The preferred compounds of the present invention exhibit $IC_{50}$ values of 1 nM to 10 μM, preferrably of 1–100 nM.

The compounds of formula I and their pharmaceutically acceptable acid addition salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula I and their pharmaceutically acceptable acid addition salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 50 mg to about 500 mg, comes into consideration for the prevention and control of topical and systemic infections by pathogenic fungi. For cholesterol lowering and treatment of impaired glucose tolerance and diabetes the daily dosage conveniently amounts to between 1 and 1000 mg, preferably 5 to 200 mg, for adult patients. Depending on the dosage it is convenient to administer the daily dosage in several dosage units.

The pharmaceutical preparations conveniently contain about 1–500 mg, preferably 5–200 mg, of a compound of formula I.

The following Examples serve to illustrate the present invention in more detail. They are, however, not intended to limit its scope in any manner.

EXAMPLES

Abbreviations:

AcOH=acetic acid, Aq=aqueous, BOC=t-butyloxycarbonyl, $CH_2Cl_2$=dichloromethane, DAST=Diethylaminosulfur trifluoride, EDCI=N-(3-Dimethylaminopropyl)-N'-ethylcarbodiimide hydrochloride, $Et_3N$=triethylamine, $Et_2O$=diethylether, EtOAc=ethylacetate, EtOH=ethanol, eq=equivalents, HOBT=1-Hydroxybenzo-triazole, Huenigs base=$iPr_2NEt$ N-ethyldiisopropylamine, LAH=Lithium aluminium hydride, $LiBH_4$=lithium borohydride, MeOH=methanol, NMM=N-methyl-morpholine, TBDMSCl=t-butyldimethylsilyl chloride, $Pd(Ph_3P)_4$=tetrakis (triphenylphosphine)palladium, $PdCl_2(PPh_3)_2$=bis (triphenylphosphine)palladium(II) chloride, TFA=trifluoroacetic acid, DMAP=4-Dimethylaminopyridine, THF=tetrahydrofurane.

General Remarks

All reactions were performed under argon.

The purification of the final amines by preparative HPLC [e.g. RP-18, acetonitrile (0.1% HCOOH)/water (0.1% HCOOH), 10% to 95% acetonitrile] yielded mixtures of the corresponding amino formate and the corresponding halogenide or mesylate which was used in the reaction. The ratio was not always determined, the purity of the final amino salts was >80% after LC-MS.

Example 1

1.1

1.4 l of nitrobenzene were cooled in an ice bath and treated in succession at a maximum temperature of 6° C. with 492.6 g (3.656 mol) of aluminum chloride and 700 g (3.355 mol) of 4-trifluoromethyl-2-fluoro-benzoyl chloride in 350 ml of nitrobenzene. The mixture was stirred (15 min) and 427.5 g (3.388 mol) of 3-fluoroanisole were added slowly so that the temperature did not rise above 6° C. The solution was left to warm to room temperature, stirred 2 h at this temperature, poured on to ice-water (2.5 l) and extracted with methylene chloride. The organic phase was washed with water and concentrated. After crystallization from THF (1.2 l)/hexane (4.2 l), 237 g (24%) of (2-Fluoro-4-methoxy-phenyl)-(4-trifluoromethyl-phenyl)-methanone were obtained, MS: 298 (M).

1.2

12.01 g (107 mmol) of potassium tert. butylate were dissolved in 425 ml of THF and treated slowly with 13.29 g (107 mmol) of benzyl mercaptane. The suspension was stirred at RT (1 h) and then treated with 29.56 g (99 mmol) of (2-Fluoro-4-methoxy-phenyl)-(4-trifluoromethyl-phenyl)-methanone in 220 ml of THF. The solution was stirred at RT (2 h), evaporated and treated with EtOAc/ aqueous NaHCO₃ solution and dried (Na₂SO₄). 42.8 g (corresponds to 99 mmol) of (2-Benzylsulfanyl-4-methoxy-phenyl)-(4-trifluoromethyl-phenyl)-methanone were obtained which were taken up in 340 ml of methylene chloride, treated at 0° C. with 13.38 g (99 mmol) of sulphuryl chloride and stirred at 0° C. for 90 min. After evaporation, the residue was taken up in 307 ml of THF, treated at 0° C. with 307 ml of a saturated ammonia solution in ethanol and stirred (16 h at RT). The solvent was removed and the residue was again taken up in sodium hydrogen carbonate solution and ethyl acetate. The phases were separated and the inorganic phase was extracted with ethyl acetate. The organic phases were washed with sodium chloride solution and dried. Recrystallization from CH₂Cl₂/methanol (−20° C.) yielded 19.8 g (71%) of 6-Methoxy-3-(4-trifluoromethyl-phenyl)-benzo[d]isothiazole, MS: 309 (M).

1.3

A solution of 20 g (64.66 mmol) of 6-Methoxy-3-(4-trifluoromethyl-phenyl)-benzo[d]isothiazole in 150 ml of acetic acid and 75 ml 62% aqueous HBr solution was heated to reflux for 70 h, subsequently cooled and taken up in ice water and extracted with tert-butylmethyleter (3×). The organic phases were washed with saturated sodium hydrogen carbonate solution (3×) and dried (Na₂SO₄). The residue was suspended in 350 ml boiling CH₂Cl₂, cooled to 3° C. and filtered to yield 15.8 g (83%) of 3-(4-Trifluoromethyl-phenyl)-benzo[d]isothiazol-6-ol, MS: 295 (M).

1.4

In analogy to examples 1.1 to 1.3, 4-bromo-benzoyl chloride and 3-fluoroanisole were converted to yield 3-(4-bromo-phenyl)-benzo[d]isothiazol-6-ol, MS: 305 (M, 1Br).

1.5

In analogy to examples 1.1 to 1.3, 4-chloro-benzoyl chloride and 3-fluoroanisole were converted to yield 3-(4-chloro-phenyl)-benzo[d]isothiazol-6-ol, MS: 261 (M, 1Cl).

1.6

In analogy to examples 1.1 to 1.3, 4-fluoro-benzoyl chloride and 3-fluoroanisole were converted to yield 3-(4-Fluoro-phenyl)-benzo[d]isothiazol-6-ol as white solide, MS: 245 (M).

1.7

In analogy to example 1.2 to 1.3, 2-fluoro-4-methoxyacetophenone gave 3-Methyl-benzo[d]isothiazol-6-ol, MS: 166 (MH⁺).

Example 2

2.1

2.0 g (6.55 mmol) 3-(4-bromo-phenyl)-benzo[d] isothiazol-6-ol in 30 ml acetone were treated with 5.89 g (42.5 mmol, 6.5 eq) K₂CO₃ and 1.9 ml (16.33 mmol, 2.5 eq) 1,4-dibromobutane. The reaction mixture was stirred at 45° C. for 8 h and at RT over night, filtered and evaporated. The excess of dibromide was removed in vacuo and the crude product was purified by column chromatography on silica gel with a gradient EtOAc:hexane 1:9 to 1:4 to yield 2.0 g (71%) 6-(4-Bromo-butoxy)-3-(4-bromo-phenyl)-benzo[d] isothiazole as yellow semisolid, MS: 439 (M, 2Br).

2.2

In analogy to example 2.1, 3-(4-bromo-phenyl)-benzo[d] isothiazol-6-ol and 1,2-dibromoethane were converted to yield 6-(2-Bromo-ethoxy)-3-(4-bromo-phenyl)-benzo[d] isothiazole as off-white solid, 105° C., MS: 411 (M, 2Br).

2.3

In analogy to example 2.1, 3-(4-bromo-phenyl)-benzo[d] isothiazol-6-ol and 1,3-dibromopropane were converted to yield 3-(4-Bromo-phenyl)-6-(3-bromo-propoxy)-benzo[d] isothiazole as yellow oil, MS: 425 (M, 2Br).

2.4

In analogy to example 2.1, 3-(4-Trifluoromethyl-phenyl)-benzo[d]isothiazol-6-ol and 1,4-dibromobutane were converted to yield 6-(4-Bromo-butoxy)-3-(4-trifluoromethyl-phenyl)-benzo[d]isothiazole as light yellow solid, MS: 429 (M, 1Br).

2.5

In analogy to example 2.1, 3-(4-chloro-phenyl)-benzo[d] isothiazol-6-ol and 1,4-dibromobutane were converted to yield 6-(4-Bromo-butoxy)-3-(4-chloro-phenyl)-benzo[d] isothiazole as white solid, mp: 68–69° C., MS: 395 (M, 1Br, 1 Cl).

2.6

In analogy to example 2.1, 3-(4-fluoro-phenyl)-benzo[d] isothiazol-6-ol and 1,4-dibromobutane were converted to yield 6-(4-Bromo-butoxy)-3-(4-fluoro-phenyl)-benzo[d] isothiazole, MS: 379 (M, 1Br).

2.7

In analogy to example 2.1, 3-Methyl-benzo[d]isothiazol-6-ol and 1,3-dibromobutane were converted to yield 6-(4-Bromo-butoxy)-3-methyl-benzo[d]isothiazole as brown oil, MS: 300 (MH⁺, 1 Br).

Example 3

3.1

75 mg (0.18 mmol) 6-(2-Bromo-ethoxy)-3-(4-bromo-phenyl)-benzo[d]isothiazole in 2.5 ml DMA were treated with 98 μl (0.54 mmol, 3eq) 5.6 M N,N-dimethylamine in ethanol for 35 h at RT. The solution was diluted with ether and a saturated aqueous solution of NaHCO₃. The inorganic phase was extracted with ether, the combined organic phases were washed with brine and dried over Na₂SO₄. Column chromatography on silica gel with CH₂Cl₂:MeOH 8:1 yielded 63 mg (92%) [2-[3-(4-Bromo-phenyl)-benzo[d] isothiazol-6-yloxy]-ethyl]-dimethyl-amine as colorless oil, MS: 377(MH⁺, 1Br).

3.2

In analogy to example 3.1, 6-(2-Bromo-ethoxy)-3-(4-bromo-phenyl)-benzo[d]isothiazole and N-Allylmethylamine were converted to yield Allyl-[2-[3-(4-bromo-phenyl)-benzo[d]isothiazol-6-yloxy]-ethyl]-methyl-amine as colorless oil, MS: 403(MH⁺, 1Br).

3.3

In analogy to example 3.1, 3-(4-Bromo-phenyl)-6-(3-bromo-propoxy)-benzo[d]isothiazole and N-Allylmethylamine were converted to yield Allyl-[3-[3-(4-bromo-phenyl)-benzo[d]isothiazol-6-yloxy]-propyl]-methyl-amine as colorless oil, MS: 417(MH⁺, 1Br).

3.4

In analogy to example 3.1, 3-(4-Bromo-phenyl)-6-(3-bromo-propoxy)-benzo[d]isothiazole and Dimethylamine were converted to yield [3-[3-(4-Bromo-phenyl)-benzo[d] isothiazol-6-yloxy]-propyl]-dimethyl-amine as white semisolid, MS: 391 (MH⁺, 1Br).

3.5

In analogy to example 3.1, 3-(4-Bromo-phenyl)-6-(3-bromo-propoxy)-benzo[d]isothiazole and N-(2-methoxyethyl)ethylamine were converted to yield (without extraction) [3-[3-(4-Bromo-phenyl)-benzo[d]isothiazol-6-yloxy]-propyl]-ethyl-(2-methoxy-ethyl)-amine hydrobromide as colorless oil, MS: 449(MH$^+$, 1Br).

3.6

In analogy to example 3.1, 6-(4-Bromo-butoxy)-3-(4-bromo-phenyl)-benzo[d]isothiazole and N-Allylmethylamine were converted to yield Allyl-[4-[3-(4-bromo-phenyl)-benzo[d]isothiazol-6-yloxy]-butyl]-methyl-amine as white semisolid, MS: 431(MH$^+$, 1Br).

3.7

In analogy to example 3.1, 6-(4-Bromo-butoxy)-3-(4-bromo-phenyl)-benzo[d]isothiazole and Dimethylamine were converted to yield [4-[3-(4-Bromo-phenyl)-benzo[d]isothiazol-6-yloxy]-butyl]-dimethyl-amine as white semisolid, MS: 405(MH$^+$, 1Br).

3.8

In analogy to example 3.1, 6-(4-Bromo-butoxy)-3-(4-bromo-phenyl)-benzo[d]isothiazole and N-(2-Methoxyethyl)ethylamine were converted to {4-[3-(4-Bromo-phenyl)-benzo[d]isothiazol-6-yloxy]-butyl}-ethyl-(2-methoxy-ethyl)-amine which was converted to the hydrochloride by treatment with HCl in methanol to yield {4-[3-(4-Bromo-phenyl)-benzo[d]isothiazol-6-yloxy]-butyl}-ethyl-(2-methoxy-ethyl)-amine hydrochloride as light yellow oil, MS: 463(MH$^+$, 1Br).

3.9

In analogy to example 3.1, 6-(4-Bromo-butoxy)-3-(4-bromo-phenyl)-benzo[d]isothiazole and piperidine were converted to yield 3-(4-Bromo-phenyl)-6-(4-piperidin-1-yl-butoxy)-benzo[d]isothiazole as white solid, MS: 445(MH$^+$, 1Br).

3.10

In analogy to example 3.1, 6-(4-Bromo-butoxy)-3-(4-bromo-phenyl)-benzo[d]isothiazole and 1-Methylpiperazine were converted to yield 3-(4-Bromo-phenyl)-6-[4-(4-methyl-piperazin-1-yl)-butoxy]-benzo[d]isothiazole as white solid, MS: 460(MH$^+$, 1Br).

3.11

In analogy to example 3.1, 6-(4-Bromo-butoxy)-3-(4-bromo-phenyl)-benzo[d]isothiazole and 1-Acetylpiperazine were converted to yield 1-(4-(4-[3-(4-Bromo-phenyl)-benzo[d]isothiazol-6-yloxy]-butyl)-piperazin-1-yl)-ethanone as white solid, MS: 488(MH$^+$, 1Br).

3.12

In analogy to example 3.1, 3-(4-Bromo-phenyl)-6-(3-bromo-propoxy)-benzo[d]isothiazole and Hydroxyethylamine were converted to yield 2-{3-[3-(4-Bromo-phenyl)-benzo[d]isothiazol-6-yloxy]-propylamino}-ethanol as white semisolid, MS: 407 (MH$^+$, 1Br).

3.13

In analogy to example 3.1, 3-(4-Bromo-phenyl)-6-(3-bromo-propoxy)-benzo[d]isothiazole and Methyl-prop-2-ynyl-amine were converted to yield {3-[3-(4-Bromo-phenyl)-benzo[d]isothiazol-6-yloxy]-propyl}-methyl-prop-2-ynyl-amine as colorless oil, MS: 415 (MH$^+$, 1Br).

3.14

In analogy to example 3.1, 3-(4-Bromo-phenyl)-6-(3-bromo-propoxy)-benzo[d]isothiazole and Prop-2-ynylamine were converted to yield {3-[3-(4-Bromo-phenyl)-benzo[d]isothiazol-6-yloxy]-propyl}-prop-2-ynyl-amine as off-white semisolid, MS: 40 1 (MH$^+$, 1Br).

3.15

In analogy to example 3.1, 3-(4-Bromo-phenyl)-6-(3-bromo-propoxy)-benzo[d]isothiazole and Piperidine were converted to yield 3-(4-Bromo-phenyl)-6-(3-piperidin-1-yl-propoxy)-benzo[d]isothiazole as pink oil, MS: 431 (MH$^+$, 1Br).

3.16

In analogy to example 3.1, 3-(4-Bromo-phenyl)-6-(3-bromo-propoxy)-benzo[d]isothiazole and 1-Methyl-piperazine were converted to yield 3-(4-Bromo-phenyl)-6-[3-(4-methyl-piperazin-1-yl)-propoxy]-benzo[d]isothiazole as colorless oil, MS: 446 (MH$^+$, 1Br).

3.17

In analogy to example 3.1, 3-(4-Bromo-phenyl)-6-(3-bromo-propoxy)-benzo[d]isothiazole and 1-Piperazin-1-yl-ethanone were converted to yield 1-(4-{3-[3-(4-Bromo-phenyl)-benzo[d]isothiazol-6-yloxy]-propyl}-piperazin-1-yl)-ethanone as colorless oil, MS: 474 (MH$^+$, 1Br).

3.18

In analogy to example 3.1, 6-(4-Bromo-butoxy)-3-(4-bromo-phenyl)-benzo[d]isothiazole and Ethylamine were converted to yield {4-[3-(4-Bromo-phenyl)-benzo[d]isothiazol-6-yloxy]-butyl}-ethyl-amine as white solid, MS: 405 (MH$^+$, 1Br).

3.19

In analogy to example 3.1, 3-(4-Bromo-phenyl)-6-(3-bromo-propoxy)-benzo[d]isothiazole and Ethylamine were converted to yield {3-[3-(4-Bromo-phenyl)-benzo[d]isothiazol-6-yloxy]-propyl}-ethyl-amine as white solid, MS: 391 (MH$^+$, 1Br).

3.20

In analogy to example 3.1, 6-(4-Bromo-butoxy)-3-(4-fluoro-phenyl)-benzo[d]isothiazole and methylaminoethanol were converted to yield 2-({4-[3-(4-Fluoro-phenyl)-benzo[d]isothiazol -6-yloxy]-butyl}-methyl -amino)-ethanol which was transferred into its salt by treatment with formic acid, MS: 375 (MH$^+$).

3.21

In analogy to example 3.1, 6-(4-Bromo-butoxy)-3-(4-fluoro-phenyl)-benzo[d]isothiazole and N-(2-Methoxyethyl)methylamine were converted to yield {4-[3-(4-Fluoro-phenyl)-benzo[d]isothiazol-6-yloxyl]-butyl}-(2-methoxy-ethyl)-methyl-amine which was transferred into its salt by treatment with formic acid, MS: 389 (MH$^+$).

3.22

In analogy to example 3.1, 6-(4-Bromo-butoxy)-3-(4-fluoro-phenyl)-benzo[d]isothiazole and N-(2-Methoxyethyl)ethylamine were converted to yield Ethyl-{4-[3-(4-fluoro-phenyl)-benzo[d]isothiazol-6-yloxy]-butyl}-(2-methoxy-ethyl)-amine which was transferred into its salt by treatment with formic acid, MS: 403 (MH$^+$).

3.23

In analogy to example 3.1, 6-(4-Bromo-butoxy)-3-(4-fluoro-phenyl)-benzo[d]isothiazole and ethylaminoethanol were converted to yield 2-(Ethyl-{4-[3-(4-fluoro-phenyl)-benzo[d]isothiazol-6-yloxy]-butyl}-amino)-ethanol which was transferred into its salt by treatment with formic acid, MS: 389 (MH$^+$).

3.24

In analogy to example 3.1, 6-(4-Bromo-butoxy)-3-methyl-benzo[d]isothiazole Ethylamino ethanol were converted to yield 2-{Ethyl-[4-(3-methyl-benzo[d]isothiazol-6-yloxy)-butyl]-amino}-ethanol as yellow oil, MS: 309 (MH$^+$).

3.25

In analogy to example 3.1, 6-(4-Bromo-butoxy)-3-methyl-benzo[d]isothiazole N-(2-Methoxyethyl)ethylamine were converted to yield Ethyl-(2-methoxy-ethyl)-[4-(3-methyl-benzo[d]isothiazol-6-yloxy)-butyl]-amine as yellow oil, MS: 323 (MH$^+$).

Example 4

1 eq of the corresponding bromide was treated with 3 eq of the corresponding amine in DMF (1 ml/mmol bromide) in the presence of 1 eq diisopropylethylamine and a catalytic amount of NaI at RT until no starting material could be detected with HPLC. Formic acid was added and the crude materials were purified by preparative HPLC [RP-18, acetonitrile (0.1% HCOOH)/water (0.1% HCOOH), 10% to 95% acetonitrile]. After evaporation the product was obtained as a mixture of amino-hydrobromides and formates.

4.1

According to the method in example 4, 6-(2-Bromo-ethoxy)-3-(4-bromo-phenyl)-benzo[d]isothiazole and 2-(methylamino)ethanol were converted to yield 2-[[2-[3-(4-Bromo-phenyl)-benzo[d]isothiazol-6-yloxy]-ethyl]-methyl-amino]-ethanol, MS: 408 (MH$^+$, 1Br).

4.2

According to the method in example 4, 6-(2-Bromo-ethoxy)-3-(4-bromo-phenyl)-benzo[d]isothiazole and N-(2-methoxyethyl)methylamine were converted to yield [2-[3-(4-Bromo-phenyl)-benzo[d]isothiazol-6-yloxy]-ethyl]-(2-methoxy-ethyl)-methyl-amine, MS: 422 (MH$^+$, 1Br).

4.3

According to the method in example 4, 6-(2-Bromo-ethoxy)-3-(4-bromo-phenyl)-benzo[d]isothiazole and morpholine were converted to yield 3-(4-Bromo-phenyl)-6-(2-morpholin-4-yl-ethoxy)-benzo[d]isothiazole, MS: 420 (MH$^+$, 1Br).

4.4

According to the method in example 4, 6-(2-Bromo-ethoxy)-3-(4-bromo-phenyl)-benzo[d]isothiazole and 2-(ethylamino)ethanol were converted to yield 2-[[2-[3-(4-Bromo-phenyl)-benzo[d]isothiazol-6-yloxy]-ethyl]-ethyl-amino]-ethanol, MS: 422 (MH$^+$, 1Br).

4.5

According to the method in example 4, 6-(2-Bromo-ethoxy)-3-(4-bromo-phenyl)-benzo[d]isothiazole and pyrrolidine were converted to yield 3-(4-Bromo-phenyl)-6-(2-pyrrolidin-1-yl-ethoxy)-benzo[d]isothiazole, MS: 404 (MH$^+$, 1Br).

4.6

According to the method in example 4, 6-(2-Bromo-ethoxy)-3-(4-bromo-phenyl)-benzo[d]isothiazole and azetidine were converted to yield 6-(2-Azetidin-1-yl-ethoxy)-3-(4-bromo-phenyl)-benzo[d]isothiazole, MS: 390 (MH$^+$, 1Br).

4.7

According to the method in example 4, 3-(4-Bromo-phenyl)-6-(3-bromo-propoxy)-benzo[d]isothiazole and 2-(methylamino)ethanol were converted to yield 2-[[3-[3-(4-Bromo-phenyl)-benzo[d]isothiazol-6-yloxy]-propyl]-methyl-amino]-ethanol, MS: 422 (MH$^+$, 1Br).

4.8

According to the method in example 4, 3-(4-Bromo-phenyl)-6-(3-bromo-propoxy)-benzo[d]isothiazole and N-(2-methoxyethyl)methylamine were converted to yield [3-[3-(4-Bromo-phenyl)-benzo[d]isothiazol-6-yloxy]-propyl]-(2-methoxy-ethyl)-methyl-amine, MS: 436 (MH$^+$, 1Br).

4.9

According to the method in example 4, 3-(4-Bromo-phenyl)-6-(3-bromo-propoxy)-benzo[d]isothiazole and morpholine were converted to yield 3-(4-Bromo-phenyl)-6-(3-morpholin-4-yl-propoxy)-benzo[d]isothiazole, MS: 434 (MH$^+$, 1Br).

4.10

According to the method in example 4, 3-(4-Bromo-phenyl)-6-(3-bromo-propoxy)-benzo[d]isothiazole and 2-(ethylamino)ethanol were converted to yield 2-[[3-[3-(4-Bromo-phenyl)-benzo[d]isothiazol-6-yloxy]-propyl]-ethyl-amino]-ethanol, MS: 436 (MH$^+$, 1Br).

4.11

According to the method in example 4, 3-(4-Bromo-phenyl)-6-(3-bromo-propoxy)-benzo[d]isothiazole and pyrrolidine were converted to yield 3-(4-Bromo-phenyl)-6-(3-pyrrolidin-1-yl-propoxy)-benzo[d]isothiazole, MS: 418 (MH$^+$, 1Br).

4.12

According to the method in example 4, 3-(4-Bromo-phenyl)-6-(3-bromo-propoxy)-benzo[d]isothiazole and azetidine were converted to yield 6-(3-Azetidin-1-yl-propoxy)-3-(4-bromo-phenyl)-benzo[d]isothiazole, MS: 404 (MH$^+$, 1Br).

4.13

According to the method in example 4, 6-(4-Bromo-butoxy)-3-(4-bromo-phenyl)-benzo[d]isothiazole and 2-(methylamino)ethanol were converted to yield 2-[[4-[3-(4-Bromo-phenyl)-benzo[d]isothiazol-6-yloxy]-butyl]-methyl-amino]-ethanol, MS: 436 (MH$^+$, 1Br).

4.14

According to the method in example 4, 6-(4-Bromo-butoxy)-3-(4-bromo-phenyl)-benzo[d]isothiazole and N-(2-methoxyethyl)methylamine were converted to yield [4-[3-(4-Bromo-phenyl)-benzo[d]isothiazol-6-yloxy]-butyl]-(2-methoxy-ethyl)-methyl-amine, MS: 450 (MH$^+$, 1Br).

4.15

According to the method in example 4, 6-(4-Bromo-butoxy)-3-(4-bromo-phenyl)-benzo[d]isothiazole and morpholine were converted to yield 3-(4-Bromo-phenyl)-6-(4-morpholin-4-yl-butoxy)-benzo[d]isothiazole, MS: 448 (MH$^+$, 1Br).

4.16

According to the method in example 4, 6-(4-Bromo-butoxy)-3-(4-bromo-phenyl)-benzo[d]isothiazole and 2-(ethylamino)ethanol were converted to yield 2-[[4-[3-(4-Bromo-phenyl)-benzo[d]isothiazol-6-yloxy]-butyl]-ethyl-amino]-ethanol, MS: 450 (MH$^+$, 1Br).

4.17

According to the method in example 4, 6-(4-Bromo-butoxy)-3-(4-bromo-phenyl)-benzo[d]isothiazole and pyrrolidine were converted to yield 3-(4-Bromo-phenyl)-6-(4-pyrrolidin-1-yl-butoxy)-benzo[d]isothiazole, MS: 432 (MH$^+$, 1Br).

4.18

According to the method in example 4, 6-(4-Bromo-butoxy)-3-(4-bromo-phenyl)-benzo[d]isothiazole and azetidine were converted to yield 6-(4-Azetidin-1-yl-butoxy)-3-(4-bromo-phenyl)-benzo[d]isothiazole, MS: 418 (MH$^+$, 1Br).

Example 5

1 eq of the corresponding bromide was treated with 3 eq of the corresponding amine in DMA (1 ml/0.25 mmol bromide) at RT until no starting material could be detected with HPLC. Formic acid was added and the crude materials were purified by preparative HPLC [RP-18, acetonitrile (0.1% HCOOH)/water (0.1% HCOOH), 10% to 95% acetonitrile]. After evaporation the product was obtained as a mixture of amino-hydrobromides and formates.

5.1

According to the method in example 5, 3-(4-Bromo-phenyl)-6-(3-bromo-propoxy)-benzo[d]isothiazole and diethanolamine were converted to yield 2-[[3-[3-(4-Bromo-phenyl)-benzo[d]isothiazol-6-yloxy]-propyl]-(2-hydroxy-ethyl)-amino]-ethanol as white semisolid, MS: 451 (MH$^+$, 1Br).

5.2

According to the method in example 5, 3-(4-Bromo-phenyl)-6-(3-bromo-propoxy)-benzo[d]isothiazole and bis(2-methoxyethyl) amine were converted to yield [3-[3-(4-Bromo-phenyl)-benzo[d]isothiazol-6-yloxy]-propyl]-bis-(2-methoxy-ethyl)-amine as orange oil, MS: 479 (MH$^+$, 1Br).

5.2

According to the method in example 5, 6-(4-Bromo-butoxy)-3-(4-bromo-phenyl)-benzo[d]isothiazole and diethanolamine were converted to yield 2-[[4-[3-(4-Bromo-phenyl)-benzo[d]isothiazol-6-yloxy]-butyl]-(2-hydroxy-ethyl)-amino]-ethanol as white semisolid, MS: 465(MH$^+$, 1Br).

5.3

According to the method in example 5, 6-(4-Bromo-butoxy)-3-(4-bromo-phenyl)-benzo[d]isothiazole and bis(2-methoxyethyl)amine were converted to yield [4-[3-(4-Bromo-phenyl)-benzo[d]isothiazol-6-yloxy]-butyl]-bis-(2-methoxy-ethyl)-amine as light yellow oil, MS: 493 (MH$^+$, 1Br).

Example 6

1 eq of the corresponding bromide was treated with 3 eq of the corresponding amine in DMA (1 ml/0.25 mmol bromide) at RT until no starting material could be detected with HPLC. Formic acid was added and the crude materials were purified by prep HPLC [RP-18, acetonitrile (0.1% HCOOH)/water (0.1% HCOOH), 10% to 95% acetonitrile]. After separation, the product was extracted with EtOAc and sat. NaHCO$_3$/H$_2$O to isolate the product as free amine. The hydrochloride salt was optionally obtained after addition of 1N HCl/MeOH and evaporation of the solvent.

6.1

According to the method in example 6, 6-(4-Bromo-butoxy)-3-(4-bromo-phenyl)-benzo[d]isothiazole and 1,1-dimethylpropargylamine were converted to yield {4-[3-(4-Bromo-phenyl)-benzo[d]isothiazol-6-yloxy]-butyl}-(1,1-dimethyl-prop-2-ynyl)-amine as colorless oil, MS: 443 (MH$^+$, 1Br).

6.2

According to the method in example 6, 6-(4-Bromo-butoxy)-3-(4-bromo-phenyl)-benzo[d]isothiazole and ethanolamine were converted to yield 2–4{-[3-(4-Bromo-phenyl)-benzo[d]isothiazol-6-yloxy]-butylamino}-ethanol as white solid, MS: 421 (MH$^+$, 1Br).

6.3

According to the method in example 6, 6-(4-Bromo-butoxy)-3-(4-bromo-phenyl)-benzo[d]isothiazole and Methyl-prop-2-ynyl-amine were converted to yield {4-[3-(4-Bromo-phenyl)-benzo[d]isothiazol-6-yloxy]-butyl-methyl-prop-2-ynyl-amine as light yellow oil, MS: 429 (MH$^+$, 1Br).

6.4

According to the method in example 6, 6-(4-Bromo-butoxy)-3-(4-bromo-phenyl)-benzo[d]isothiazole and propargylamine were converted to yield {4-[3-(4-Bromo-phenyl)-benzo[d]isothiazol-6-yloxy]-butyl}-prop-2-ynyl-amine hydrochloride as off-white solid, MS: 415(MH$^+$, 1Br).

Example 7

A solution of 0.25 mmol (1 equivalent) of the corresponding bromide in 0.7 ml dry DMA was treated with a solution of 0.5 mmol (2 equivalents) of the corresponding secondary amine in 0.15 ml dry DMA at room temperature. After 16 h, 2 equivalents of secondary amine were added again to the solution. The reaction mixture was allowed to stand over night at room temperature, treated with 0.2 ml formic acid and purified by preparative HPLC [RP-18, acetonitrile (0.1% HCOOH)/water (0.1% HCOOH), 10% to 95% acetonitrile]. After evaporation, the product was obtained as a mixture of amino hydrobromide and formate. Optionally the product was extracted with EtOAc and sat. NaHCO$_3$/H$_2$O to obtain the corresponding free amine.

7.1

According to the method in example 7, 6-(4-Bromo-butoxy)-3-(4-trifluoromethyl-phenyl)-benzo[d]isothiazole and Diethylamine were converted to yield Diethyl-{4-[3-(4-trifluoromethyl-phenyl)-benzo[d]isothiazol-6-yloxy]-butyl}-amine, MS: 423 (MH$^+$).

7.2

According to the method in example 7, 6-(4-Bromo-butoxy)-3-(4-trifluoromethyl-phenyl)-benzo[d]isothiazole and Piperidine were converted to yield 6-(4-Piperidin-1-yl-butoxy)-3-(4-trifluoromethyl-phenyl)-benzo[d]isothiazole, MS: 435 (MH$^+$).

7.3

According to the method in example 7, 6-(4-Bromo-butoxy)-3-(4-trifluoromethyl-phenyl)-benzo[d]isothiazole and Allylmethylamine were converted to yield Allyl-methyl-{4-[3-(4-trifluoromethyl-phenyl)-benzo[d]isothiazol-6-yloxy]-butyl}-amine, MS: 421 (MH$^+$).

7.4

According to the method in example 7, 6-(4-Bromo-butoxy)-3-(4-trifluoromethyl-phenyl)-benzo[d]isothiazole and Trimethyleneimine were converted to yield 6-(4-Azetidin-1-yl-butoxy)-3-(4-trifluoromethyl-phenyl)-benzo[d]isothiazole, MS: 407 (MH$^+$).

7.5

According to the method in example 7, 6-(4-Bromo-butoxy)-3-(4-trifluoromethyl-phenyl)-benzo[d]isothiazole and Ethylamino ethanol were converted to yield 2-(Ethyl-{4-[3-(4-trifluoromethyl-phenyl)-benzo[d]isothiazol-6-yloxy]-butyl}-amino)-ethanol, MS: 439 (MH$^+$).

7.6

According to the method in example 7, 6-(4-Bromo-butoxy)-3-(4-trifluoromethyl-phenyl)-benzo[d]isothiazole and Diethanoleamine were converted to yield 2-((2-Hydroxy-ethyl)-{4-[3-(4-trifluoromethyl-phenyl)-benzo[d]isothiazol-6-yloxy]-butyl}-amino)-ethanol, MS: 455 (MH$^+$).

7.7

According to the method in example 7, 6-(4-Bromo-butoxy)-3-(4-trifluoromethyl-phenyl)-benzo[d]isothiazole and Dimethylamine were converted to yield Dimethyl-{4-[3-(4-trifluoromethyl-phenyl)-benzo[d]isothiazol-6-yloxy]-butyl}-amine, MS: 395 (MH$^+$).

7.8

According to the method in example 7, 6-(4-Bromo-butoxy)-3-(4-chloro-phenyl)-benzo[d]isothiazole and N-Allylmethylamine were converted to yield Allyl-{4-[3-(4-chloro-phenyl)-benzo[d]isothiazol-6-yloxy]-butyl}-methyl-amine, MS: 387 (MH$^+$, 1 Cl).

7.9

According to the method in example 7, 6-(4-Bromo-butoxy)-3-(4-chloro-phenyl)-benzo[d]isothiazole and 2-Ethylamino-ethanol were converted to yield 2-({4-[3-(4-Chloro-phenyl)-benzo[d]isothiazol-6-yloxy]-butyl}-ethyl-amino)-ethanol, MS: 405 (MH$^+$, 1Cl).

7.10

According to the method in example 7, 6-(4-Bromo-butoxy)-3-(4-chloro-phenyl)-benzo[d]isothiazole and Azetidine were converted to yield 6-(4-Azetidin-1-yl-butoxy)-3-(4-chloro-phenyl)-benzo[d]isothiazole, MS: 373 (MH$^+$, 1Cl).

7.11

According to the method in example 7, 6-(4-Bromo-butoxy)-3-(4-chloro-phenyl)-benzo[d]isothiazole and Piperidine were converted to yield 3-(4-Chloro-phenyl)-6-(4-piperidin-1-yl-butoxy)-benzo[d]isothiazole, MS: 401 (MH$^+$, 1Cl).

7.12

According to the method in example 7, 6-(4-Bromo-butoxy)-3-(4-chloro-phenyl)-benzo[d]isothiazole and N-(2-Methoxyethyl)ethylamine were converted to yield {4-[3-(4-Chloro-phenyl)-benzo[d]isothiazol-6-yloxy]-butyl}-ethyl-(2-methoxy-ethyl)-amine, MS: 419 (MH$^+$, 1Cl).

7.13

According to the method in example 7, 6-(4-Bromo-butoxy)-3-(4-chloro-phenyl)-benzo[d]isothiazole and Diethylamine were converted to yield {4-[3-(4-Chloro-phenyl)-benzo[d]isothiazol-6-yloxy]-butyl}-diethyl-amine, MS: 389 (MH$^+$, 1Cl).

7.14

According to the method in example 7, 6-(4-Bromo-butoxy)-3-(4-chloro-phenyl)-benzo[d]isothiazole and N-Methylcyclopropanemethylamine were converted to yield {4-[3-(4-Chloro-phenyl)-benzo[d]isothiazol-6-yloxy]-butyl}-cyclopropylmethyl-methyl-amine, MS: 401 (MH$^+$, 1Cl).

7.15

According to the method in example 7, 6-(4-Bromo-butoxy)-3-(4-chloro-phenyl)-benzo[d]isothiazole and N-Isopropylmethylamine were converted to yield {4-[3-(4-Chloro-phenyl)-benzo[d]isothiazol-6-yloxy]-butyl}-isopropyl-methyl-amine, MS: 389 (MH$^+$, 1Cl).

7.16

According to the method in example 7, 6-(4-Bromo-butoxy)-3-(4-chloro-phenyl)-benzo[d]isothiazole and Pyrrolidine were converted to yield 3-(4-Chloro-phenyl)-6-(4-pyrrolidin-1-yl-butoxy)-benzo[d]isothiazole, MS: 387 (MH$^+$, 1Cl).

7.17

According to the method in example 7, 6-(4-Bromo-butoxy)-3-(4-chloro-phenyl)-benzo[d]isothiazole and N-(2-Methoxyethyl)Methylamine were converted to yield {4-[3-(4-Chloro-phenyl)-benzo[d]isothiazol-6-yloxy]-butyl}-(2-methoxy-ethyl)-methyl-amine, MS: 405 (MH$^+$, 1Cl).

7.18

According to the method in example 7, 6-(4-Bromo-butoxy)-3-(4-chloro-phenyl)-benzo[d]isothiazole and 2-(Methylamino)Ethanol were converted to yield 2-({4-[3-(4-Chloro-phenyl)-benzo[d]isothiazol-6-yloxy]-butyl}-methyl-amino)-ethanol, MS: 391 (MH$^+$, 1Cl).

7.19

According to the method in example 7, 6-(4-Bromo-butoxy)-3-(4-chloro-phenyl)-benzo[d]isothiazole and (R)-3-Hydroxypyrrolidine were converted to yield (3R)—1-{4-[3-(4-Chloro-phenyl)-benzo[d]isothiazol-6-yloxy]-butyl}-pyrrolidin-3-ol, MS: 403 (MH$^+$, 1Cl).

Example 8

8.1

To 4.4 g (10 mmol) 6-(4-Bromo-butoxy)-3-(4-bromo-phenyl)-benzo[d]isothiazole in 400 ml CH$_2$Cl$_2$, 24 g potassium permanganate on silica gel were added, which were prepared from 7 g KMnO$_4$, 20 g silica gel and 10 ml water prior to use. The mixture was stirred at 50° C. for 2 days, filtered and the crude material purified by column chromatography with EtOAc:hexane 1:4 to give 1.6 g (34%) 6-(4-Bromo-butoxy)-3-(4-bromo-phenyl)-benzo[d]isothiazole 1,1-dioxide as off-white solid, MS: 473 (MH$^+$, 1Br).

8.2

In analogy to example 8.1, 3-(4-Bromo-phenyl)-6-(3-bromo-propoxy)-benzo[d]isothiazole was converted to 3-(4-Bromo-phenyl)-6-(3-bromo-propoxy)-benzo[d]isothiazole 1,1-dioxide as off-white solid, MS: 457 (M, 2Br).

8.3

In analogy to example 8.1, 6-(4-Bromo-butoxy)-3-(4-trifluoromethyl-phenyl)-benzo[d]isothiazole was converted to 6-(4-Bromo-butoxy)-3-(4-trifluoromethyl-phenyl)-benzo[d]isothiazole 1,1-dioxide as light brown solid, which was used in subsequent reaction steps without further purification.

8.4

In analogy to example 8.1, 6-(4-Bromo-butoxy)-3-(4-chloro-phenyl)-benzo[d]isothiazole was converted to 6-(4-Bromo-butoxy)-3-(4-chloro-phenyl)-benzo[d]isothiazole 1,1-dioxide as light yellow solid, MS: 426 (M, 1Br, 1 Cl).

Example 9

1 eq of the corresponding bromide was treated with 3 eq of the corresponding amine in DMA (1 ml/0.25 mmol bromide) at RT until no starting material could be detected with HPLC. Formic acid was added and the crude materials were purified by preparative HPLC [RP-18, acetonitrile (0.1% HCOOH)/water (0.1% HCOOH), 10% to 95% acetonitrile]. After evaporation the product was obtained as a mixture of amino-hydrobromides and formates.

9.1
According to the method in example 9, 3-(4-Bromo-phenyl)-6-(3-bromo-propoxy)-benzo[d]isothiazole 1,1-dioxide and dimethylamine were converted to yield (3-[3-(4-Bromo-phenyl)-1,1-dioxo-1H-11 6-benzo[d]isothiazol-6-yloxy]-propyl)-dimethyl-amine as yellow solid, MS: 423 (MH$^+$, 1Br).

9.2
According to the method in example 9, 3-(4-Bromo-phenyl)-6-(3-bromo-propoxy)-benzo[d]isothiazole 1,1-dioxide and N-allylmethylamine were converted to yield Allyl-(3-[3-(4-bromo-phenyl)-1,1-dioxo-1H-11 6-benzo[d]isothiazol-6-yloxy]-propyl)-methyl-amine as yellow solid, MS: 449 (MH$^+$, 1Br).

9.3
According to the method in example 9, 3-(4-Bromo-phenyl)-6-(3-bromo-propoxy)-benzo[d]isothiazole 1,1-dioxide and azetidine were converted to yield 6-(3-Azetidin-1-yl-propoxy)-3-(4-bromo-phenyl)-benzo[d]isothiazole 1,1-dioxide as yellow solid, MS: 435 (MH$^+$, 1Br).

9.4
According to the method in example 9, 3-(4-Bromo-phenyl)-6-(3-bromo-propoxy)-benzo[d]isothiazole 1,1-dioxide and N-Methylproylamine were converted to yield {3-[3-(4-Bromo-phenyl)-1,1-dioxo-1H-11 6-benzo[d]isothiazol-6-yloxy]-propyl}-methyl-propyl-amine as yellow solid, MS: 451 (MH$^+$, 1Br).

9.5
According to the method in example 9, 3-(4-Bromo-phenyl)-6-(3-bromo-propoxy)-benzo[d]isothiazole 1,1-dioxide and 2-Ethylaminoethanol were converted to yield 2-({3-[3-(4-Bromo-phenyl)-1,1-dioxo-1H-11 6-benzo[d]isothiazol-6-yloxy]-propyl}-ethyl-amino)-ethanol as yellow solid, MS: 467(MH$^+$, 1Br).

9.6
According to the method in example 9, 3-(4-Bromo-phenyl)-6-(3-bromo-propoxy)-benzo[d]isothiazole 1,1-dioxide and diethylamine were converted to yield {3-[3-(4-Bromo-phenyl)-1,1-dioxo-1H-11 6-benzo[d]isothiazol-6-yloxy]-propyl}-diethyl-amine as yellow solid, MS: 451 (MH$^+$, 1Br).

9.7
According to the method in example 9, 3-(4-Bromo-phenyl)-6-(3-bromo-propoxy)-benzo[d]isothiazole 1,1-dioxide and N-(2-methoxyethyl)methylamine were converted to yield {3-[3-(4-Bromo-phenyl)-1,1-dioxo-1H-11 6-benzo[d]isothiazol-6-yloxy]-propyl}-(2-methoxy-ethyl)-methyl-amine as yellow solid, MS: 467 (MH$^+$, 1Br).

9.8
According to the method in example 9, 3-(4-Bromo-phenyl)-6-(3-bromo-propoxy)-benzo[d]isothiazole 1,1-dioxide and 2-methylaminoethanol were converted to yield 2-({3-[3-(4-Bromo-phenyl)-1H-dioxo-1H-11 6-benzo[d]isothiazol-6-yloxy]-propyl}-methyl-amino)-ethanol as yellow solid, MS: 453 (MH$^+$, 1Br).

9.9
According to the method in example 9, 3-(4-Bromo-phenyl)-6-(3-bromo-propoxy)-benzo[d]isothiazole 1,1-dioxide and N-(2-methoxyethyl)ethylamine were converted to yield {3-[3-(4-Bromo-phenyl)-1,1-dioxo-1H-11 6-benzo[d]isothiazol-6-yloxy]-propyl}-ethyl-(2-methoxy-ethyl)-amine as yellow solid, MS: 481 (MH$^+$, 1Br).

9.10
According to the method in example 9, 6-(4-Bromo-butoxy)-3-(4-bromo-phenyl)-benzo[d]isothiazole 1,1-dioxide and dimethylamine were converted to yield (4-[3-(4-Bromo-phenyl)-1,1-dioxo-1H-11 6-benzo[d]isothiazol-6-yloxy]-butyl)-dimethyl-amine as yellow solid, MS: 437 (MH$^+$, 1Br).

9.11
According to the method in example 9, 6-(4-Bromo-butoxy)-3-(4-bromo-phenyl)-benzo[d]isothiazole 1,1-dioxide and N-allylmethylamine were converted to yield Allyl-(4-[3-(4-bromo-phenyl)-1,1-dioxo-1H-11 6-benzo[d]isothiazol-6-yloxy]-butyl)-methyl-amine as yellow solid, MS: 463 (MH$^+$, 1Br).

9.12
According to the method in example 9, 6-(4-Bromo-butoxy)-3-(4-bromo-phenyl)-benzo[d]isothiazole 1,1-dioxide and azetidine were converted to yield 6-(4-Azetidin-1-yl-butoxy)-3-(4-bromo-phenyl)-benzo[d]isothiazole 1,1-dioxide as yellow solid, MS: 449 (MH$^+$, 1Br).

9.13
According to the method in example 9, 6-(4-Bromo-butoxy)-3-(4-bromo-phenyl)-benzo[d]isothiazole 1,1-dioxide and N-Methylproylamine were converted to yield {4-[3-(4-Bromo-phenyl)-1,1-dioxo-1H-11 6-benzo[d]isothiazol-6-yloxy]-butyl}-methyl-propyl-amine as yellow solid, MS: 465 (MH$^+$, 1Br).

9.14
According to the method in example 9, 6-(4-Bromo-butoxy)-3-(4-bromo-phenyl)-benzo[d]isothiazole 1,1-dioxide and 2-Ethylaminoethanol were converted to yield 2-({4-[3-(4-Bromo-phenyl)-1,1-dioxo-1H-11 6-benzo[d]isothiazol-6-yloxy]-butyl}-ethyl-amino)-ethanol as yellow solid, MS: 481 (MH$^+$, 1Br).

9.15
According to the method in example 9, 6-(4-Bromo-butoxy)-3-(4-bromo-phenyl)-benzo[d]isothiazole 1,1-dioxide and diethylamine were converted to yield {4-[3-(4-Bromo-phenyl)-1,1-dioxo-1H-11 6-benzo[d]isothiazol-6-yloxy]-butyl}-diethyl-amine as yellow solid, MS: 465 (MH$^+$, 1Br).

9.16
According to the method in example 9, 6-(4-Bromo-butoxy)-3-(4-bromo-phenyl)-benzo[d]isothiazole 1,1-dioxide and N-(2-methoxyethyl)methylamine were converted to yield {4-[3-(4-Bromo-phenyl)-1,1-dioxo-1H-11 6-benzo[d]isothiazol-6-yloxy]-butyl}-(2-methoxy-ethyl)-methyl-amine as yellow solid, MS: 481 (MH$^+$, 1Br).

9.17
According to the method in example 9, 6-(4-Bromo-butoxy)-3-(4-bromo-phenyl)-benzo[d]isothiazole 1,1-dioxide and 2-methylaminoethanol were converted to yield 2-({4-[3-(4-Bromo-phenyl)-1,1-dioxo-1H-11 6-benzo[d]isothiazol-6-yloxy]-butyl}-methyl-amino)-ethanol as yellow solid, MS: 467 (MH$^+$, 1Br).

9.18
According to the method in example 9, 6-(4-Bromo-butoxy)-3-(4-bromo-phenyl)-benzo[d]isothiazole 1,1- dioxide and N-(2-methoxyethyl)ethylamine were converted to yield {4-[3-(4-Bromo-phenyl)-1,1-dioxo-1H-11 6-benzo[d]isothiazol-6-yloxy]-butyl}-ethyl-(2-methoxy-ethyl)-amine as yellow solid, MS: 495 (MH$^+$, 1Br).

9.19

According to the method in example 9, 6-(4-Bromo-butoxy)-3-(4-bromo-phenyl)-benzo[d]isothiazole 1,1-dioxide and bis(2-methoxyethyl)amine were converted to yield (4-[3-(4-Bromo-phenyl)-1,1-dioxo-1H-11 6-benzo[d]isothiazol-6-yloxy]-butyl)-bis-(2-methoxy-ethyl)-amine, which was converted with HCl/MeOH to yield the corresponding hydrochloride as yellow semisolid, MS: 525(MH$^+$, 1Br).

Example 10

A solution of 0.25 mmol (1 equivalent) of the corresponding bromide in 0.7 ml dry DMA was treated with a solution of 0.5 mmol (2 equivalents) of the corresponding secondary amine in 0.15 ml dry DMA at room temperature. After 16 h, additional 2 equivalents of secondary amine were added to the solution. The reaction mixture was allowed to stand over night at room temperature, treated with 0.2 ml formic acid and purified by preparative HPLC [RP-18, acetonitrile (0.1% HCOOH)/water (0.1% HCOOH), 10% to 95% acetonitrile]. After evaporation, the product was obtained as a mixture of amino hydrobromide and formate.

10.1

According to the method in example 10, 6-(4-Bromo-butoxy)-3-(4-trifluoromethyl-phenyl)-benzo[d]isothiazole 1,1-dioxide and Allylmethylamine were converted to yield Allyl-{4-[1,1-dioxo-3-(4-trifluoromethyl-phenyl)-1H-11 6-benzo[d]isothiazol-6-yloxy]-butyl}-methyl-amine, MS: 453 (MH$^+$).

10.2

According to the method in example 10, 6-(4-Bromo-butoxy)-3-(4-trifluoromethyl-phenyl)-benzo[d]isothiazole 1,1-dioxide and 2-Ethylaminoethanol were converted to yield 2-({4-[1,1-Dioxo-3-(4-trifluoromethyl-phenyl)-1H-11 6-benzo[d]isothiazol-6-yloxy]-butyl}-ethyl-amino)-ethanol, MS: 471 (MH$^+$).

10.3

According to the method in example 10, 6-(4-Bromo-butoxy)-3-(4-trifluoromethyl-phenyl)-benzo[d]isothiazole 1,1-dioxide and Diethylamine were converted to yield {4-[1,1-Dioxo-3-(4-trifluoromethyl-phenyl)-1H-11 6-benzo[d]isothiazol-6-yloxy]-butyl}-diethyl-amine, MS: 455 (MH$^+$).

10.4

According to the method in example 10, 6-(4-Bromo-butoxy)-3-(4-trifluoromethyl-phenyl)-benzo[d]isothiazole 1,1-dioxide and Dimethylamine were converted to yield {4-[1,1-Dioxo-3-(4-trifluoromethyl-phenyl)-1H-11 6-benzo[d]isothiazol-6-yloxy]-butyl}-dimethyl-amine, MS: 427 (MH$^+$).

10.5

According to the method in example 10, 6-(4-Bromo-butoxy)-3-(4-trifluoromethyl-phenyl)-benzo[d]isothiazole 1,1-dioxide and Piperidine were converted to yield 6-(4-Piperidin-1-yl-butoxy)-3-(4-trifluoromethyl-phenyl)-benzo[d]isothiazole 1,1-dioxide, MS: 467 (MH$^+$).

10.6

According to the method in example 10, 6-(4-Bromo-butoxy)-3-(4-trifluoromethyl-phenyl)-benzo[d]isothiazole 1,1-dioxide and Trimethyleneamine were converted to yield 6-(4-Azetidin-1-yl-butoxy)-3-(4-trifluoromethyl-phenyl)-benzo[d]isothiazole 1,1-dioxide, MS: 439 (MH$^+$).

10.7

According to the method in example 10, 6-(4-Bromo-butoxy)-3-(4-trifluoromethyl-phenyl)-benzo[d]isothiazole 1,1-dioxide and Diethanolamine were converted to yield 2-[{4-[1,1-Dioxo-3-(4-trifluoromethyl-phenyl)-1H-11 6-benzo[d]isothiazol-6-yloxy]-butyl}-(2-hydroxy-ethyl)-amino]-ethanol, MS: 487 (MH$^+$).

10.8

According to the method in example 10, 6-(4-Bromo-butoxy)-3-(4-chloro-phenyl)-benzo[d]isothiazole 1,1-dioxide and Piperidine were converted to yield 3-(4-Chloro-phenyl)-6-(4-piperidin-1-yl-butoxy)-benzo[d]isothiazole 1,1-dioxide, MS: 433 (MH$^+$, 1Cl).

10.9

According to the method in example 10, 6-(4-Bromo-butoxy)-3-(4-chloro-phenyl)-benzo[d]isothiazole 1,1-dioxide and Allyl-methyl-amine were converted to yield Allyl-{4-[3-(4-chloro-phenyl)-1,1-dioxo-1H-11 6-benzo[d]isothiazol-6-yloxy]-butyl}-methyl-amine, MS: 419 (MH$^+$, 1Cl).

10.10

According to the method in example 10, 6-(4-Bromo-butoxy)-3-(4-chloro-phenyl)-benzo[d]isothiazole 1,11-dioxide and Azetidine were converted to yield 6-(4-Azetidin-1-yl-butoxy)-3-(4-chloro-phenyl)-benzo[d]isothiazole 1,1-dioxide, MS: 405 (MH$^+$, 1Cl).

10.11

According to the method in example 10, 6-(4-Bromo-butoxy)-3-(4-chloro-phenyl)-benzo[d]isothiazole 1,1-dioxide and Ethyl-(2-methoxy-ethyl)-amine were converted to yield {4-[3-(4-Chloro-phenyl)-1,1-dioxo-1H-11 6-benzo[d]isothiazol-6-yloxy]-butyl}1-ethyl-(2-methoxy-ethyl)-amine, MS: 451 (MH$^+$, 1Cl).

10.12

According to the method in example 10, 6-(4-Bromo-butoxy)-3-(4-chloro-phenyl)-benzo[d]isothiazole 1,1-dioxide and 2-Ethylamino-ethanol were converted to yield 2-({4-[3-(4-Chloro-phenyl)-1,1-dioxo-1H-11 6-benzo[d]isothiazol-6-yloxy]-butyl-ethyl-amino)-ethanol, MS: 437 (MH$^+$, 1Cl).

10.13

According to the method in example 10, 6-(4-Bromo-butoxy)-3-(4-chloro-phenyl)-benzo[d]isothiazole 1,1-dioxide and Diethyl-amine were converted to yield 24-[3-(4-Chloro-phenyl)-1H-dioxo-1H-11 6-benzo[d]isothiazol-6-yloxy]-butyl}-diethyl-amine, MS: 421 (MH$^+$, 1Cl).

10.14

According to the method in example 10, 6-(4-Bromo-butoxy)-3-(4-chloro-phenyl)-benzo[d]isothiazole 1,1-dioxide and 2-Methylamino-ethanol were converted to yield 2-({4-[3-(4-Chloro-phenyl)-1,1-dioxo-1H-11 6-benzo[d]isothiazol-6-yloxy]-butyl}-methyl-amino)-ethanol, MS: 423 (MH$^+$, 1Cl).

10.15

According to the method in example 10, 6-(4-Bromo-butoxy)-3-(4-chloro-phenyl)-benzo[d]isothiazole 1H-dioxide and (2-Methoxy-ethyl)-methyl-amine were converted to yield {4-[3-(4-Chloro-phenyl)-1H-dioxo-1H-11 6-benzo[d]isothiazol-6-yloxy]-butyl}-(2-methoxy-ethyl)-methyl-amine, MS: 437 (MH$^+$, 1Cl).

10.16

According to the method in example 10, 6-(4-Bromo-butoxy)-3-(4-chloro-phenyl)-benzo[d]isothiazole 1,1-dioxide and Pyrrolidine were converted to yield 3-(4-Chloro-phenyl)-6-(4-pyrrolidin-1-yl-butoxy)-benzo[d]isothiazole 1,1-dioxide, MS: 419 (MH$^+$, 1 Cl).

10.17

According to the method in example 10, 6-(4-Bromo-butoxy)-3-(4-chloro-phenyl)-benzo[d]isothiazole 1,1-dioxide and (3R)-Pyrrolidin-3-ol were converted to yield 1-{4-[3-(4-Chloro-phenyl)-1H-dioxo-1H-11 6-benzo[d]isothiazol-6-yloxy]-butyl}-pyrrolidin-3-ol, MS: 435 (MH$^+$, 1Cl).

10.18

According to the method in example 10, 6-(4-Bromo-butoxy)-3-(4-chloro-phenyl)-benzo[d]isothiazole 1,1-dioxide and Isopropyl-methyl-amine were converted to yield {4-[3-(4-Chloro-phenyl)-1,1-dioxo-1H-11 6-benzo[d]isothiazol-6-yloxy]-butyl}-isopropyl-methyl-amine, MS: 421 (MH$^+$, 1Cl).

10.19

According to the method in example 10, 6-(4-Bromo-butoxy)-3-(4-chloro-phenyl)-benzo[d]isothiazole 1,1-dioxide and Cyclopropylmethyl-methyl-amine were converted to yield {4-[3-(4-Chloro-phenyl)-1,1-dioxo-1H-11 6-benzo[d]isothiazol-6-yloxy]-butyl}-cyclopropylmethyl-methyl-amine, MS: 433 (MH$^+$, 1Cl).

10.20

According to the method in example 10, 6-(4-Bromo-butoxy)-3-(4-chloro-phenyl)-benzo[d]isothiazole 1,1-dioxide and N-Methylpropylamine were converted to yield {4-[3-(4-Chloro-phenyl)-1,1-dioxo-1H-11 6-benzo[d]isothiazol-6-yloxy]-butyl-methyl-propyl-amine, MS: 421 (MH$^+$, 1Cl).

Example 11

To a suspension of 36 mg (0.38 mmol, 2.2 eq) Hydrogen peroxide-Urea adduct in 0.2 ml CH$_2$Cl$_2$, 28 mg (0.19 mmol, 1.1 eq) phthalic anhydride were added and stirred for 15 min at RT. 75 mg (0.17 mmol, 1.0 eq) {4-[3-(4-Bromo-phenyl)-1,1-dioxo-1H-11 6-benzo[d]isothiazol-6-yloxy]-butyl}-dimethyl-amine in 0.3 ml CH$_2$Cl$_2$ were added and the mixture was stirred at RT for 2 h. 1M aqueous K$_2$CO$_3$ solution was added (pH 7) and the inorganic phase was extracted with CH$_2$Cl$_2$. The organic phases were washed with water and brine and dried over Na$_2$SO$_4$. Column chromatography on silica gel with CH$_2$Cl$_2$:MeOH 8:1 yielded 48 mg (62%) {4-[3-(4-Bromo-phenyl)-1,1-dioxo-1H-11 6-benzo[d]isothiazol-6-yloxy]-butyl}-dimethyl-amine N-oxide as light yellow semisolid, MS: 453(MH$^+$, 1Br).

11.2

In analogy to example 11.1, {4-[3-(4-Bromo-phenyl)-1,1-dioxo-1H-11 6-benzo[d]isothiazol-6-yloxy]-butyl}-(2-methoxy-ethyl)-methyl-amine was converted to yield {4-[3-(4-Bromo-phenyl)-1,1-dioxo-1H-11 6-benzo[d]isothiazol-6-yloxy]-butyl}-(2-methoxy-ethyl)-methyl-amine N-oxide as light yellow semisolid, MS: 497 (MH$^+$, 1Br).

11.3

In analogy to example 11.1, (4-[3-(4-Bromo-phenyl)-1,1-dioxo-1H-11 6-benzo[d]isothiazol-6-yloxy]-butyl)-bis-(2-methoxy-ethyl)-amine was converted to yield (4-[3-(4-Bromo-phenyl)-1,1-dioxo-1H-11 6-benzo[d]isothiazol-6-yloxy]-butyl)-bis-(2-methoxy-ethyl)-amine N-oxide as yellow semisolid, MS: 541 (MH$^+$, 1Br).

11.4

In analogy to example 11,1, {4-[3-(4-Bromo-phenyl)-benzo[d]isothiazol-6-yloxy]-butyl}-[2-(tert-butyl-dimethyl-silanyloxy)-ethyl]-ethyl-amine was converted to {4-[3-(4-Bromo-phenyl)-benzo[d]isothiazol-6-yloxy]-butyl}-[2-(tert-butyl-dimethyl-silanyloxy)-ethyl-amine N-oxide which was dissolved in THF and treated with 1M Bu$_4$NF in THF over night (see example 36.1) to yield 2-({4-[3-(4-Bromo-phenyl)-benzo[d]isothiazol-6-yloxy]-butyl}-ethyl-amino)-ethanol N-oxide as off-white semisolid, MS: 465 (MH$^+$, 1Br).

Example 12

12.1

5.0 g (16.33 mmol) 3-(4-bromo-phenyl)-benzo[d]isothiazol-6-ol in 8 ml pyridine were treated with 3 ml (17.96 mmol) trifluoromethane sulfonic anhydride at 0° C. The solution was stirred for 1.5 h at RT. The solution was diluted with ether and water, the phases were separated and the inorganic phase was extracted with ether. The combined organic phases were washed with 2M HCl and brine and dried over Na$_2$SO$_4$. Evaporation yielded 7.21 crude Trifluoro-methanesulfonic acid 3-(4-bromo-phenyl)-benzo[d]isothiazol-6-yl ester as yellow oil, MS: 437 (M, 1Br).

12.2

In analogy to example 12.1, 3-(4-Trifluoromethyl-phenyl)-benzo[d]isothiazol-6-ol and trifluoromethane sulfonic anhydride were converted to yield Trifluoro-methanesulfonic acid 3-(4-trifluoromethyl-phenyl)-benzo[d]isothiazol-6-yl ester as light brown solid, MS: 427 (M).

12.3

In analogy to example 12.1, 3-(4-chloro-phenyl)-benzo[d]isothiazol-6-ol and trifluoromethane sulfonic anhydride were converted to yield Trifluoro-methanesulfonic acid 3-(4-chloro-phenyl)-benzo[d]isothiazol-6-yl ester as orange oil, MS: 393 (MH$^+$, 1Cl).

Example 13

13.1

3.0 g (6.846 mmol) Trifluoro-methanesulfonic acid 3-(4-bromo-phenyl)-benzo[d]isothiazol-6-yl ester were suspended three times with toluene prior to the reaction, then dissolved in 25 ml THF and added to 240 mg (0.34 mmol) PdCl$_2$(PPh$_3$)$_2$. To this suspension 0.67 ml (7.19 mmol) 4-pentyn-1-ol in 1 ml THF were added, followed by 54 mg (0.205 mmol) triphenylphosphine in 1 ml THF and 2.9 ml (20.54 mmol) triethylamine. The solution was stirred for 20 min at RT prior to the addition of 13 mg (0.07 mmol) CuI. The solution was heated to 50° C. overnight. Further 132 μl (1.4 mmol) 4-pentyn-1-ol in 0.8 ml THF were added in two portions and stirring at 50° C. was continued for 5 h and at RT over night. The reaction mixture was diluted with EtOAc and 1M KHSO$_4$. The inorganic phase was extracted with EtOAc and the combined organic phases were washed with water and brine and dried over Na$_2$SO$_4$. Column chromatography with a gradient hexane:EtOAc 2:1 to 1:1 gave 1.83 g (72%) 5-[3-(4-Bromo-phenyl)-benzo[d]isothiazol-6-yl]-pent-4-yn-1-ol as light yellow oil, MS: 371 (M, 1Br).

13.2

In analogy to example 13.1, Trifluoro-methanesulfonic acid 3-(4-bromo-phenyl)-benzo[d]isothiazol-6-yl ester and 2-propyn-1-ol were converted to yield 3-[3-(4-Bromo-phenyl)-benzo[d]isothiazol-6-yl]-prop-2-yn-1-ol as light brown solid, MS: 343 (MH$^+$, 1Br).

13.3

In analogy to example 13.1, Trifluoro-methanesulfonic acid 3-(4-bromo-phenyl)-benzo[d]isothiazol-6-yl ester and 3-butyn-1-ol were converted to yield 4-[3-(4-Bromo-phenyl)-benzo[d]isothiazol-6-yl]-but-3-yn-1-ol as orange solid, MS: 357 (M, 1Br).

13.4

In analogy to example 13.1, Trifluoro-methanesulfonic acid 3-(4-bromo-phenyl)-benzo[d]isothiazol-6-yl ester and 2-Methyl-3-butyn-2-ol were converted to yield 4-[3-(4-Bromo-phenyl)-benzo[d]isothiazol-6-yl]-2-methyl-but-3-yn-2-ol as light yellow semisolid, MS: 371 (M, 1Br).

Example 14

14.1

To 3.3 g (7.72 mmol) Trifluoro-methanesulfonic acid 3-(4-trifluoromethyl-phenyl)-benzo[d]isothiazol-6-yl ester in 20 ml piperidine 447.0 mg (3.9 mmol) tetrakis (triphenylphosphine)palladium and 73.6 mg (3.9 mmol) CuI were added. At 80° C. 1.43 ml (15.45 mmol) 4-pentyn-1-ol were added slowly, and the solution was stirred for an additional hour. The cooled solution was added to ice water, acidified with 2M HCl and extracted with ether. The combined organic phases were washed with water and dried over Na$_2$SO$_4$. Column chromatography on silica gel with CH$_2$Cl$_2$:MeOH 30:1 yielded 2.7 g (96%) 5-[3-(4-Trifluoromethyl-phenyl)-benzo[d]isothiazol-6-yl]-pent-4-yn-1-ol as orange oil, MS: 361(M).

14.2

In analogy to example 14.1, Trifluoro-methanesulfonic acid 3-(4-trifluoromethyl-phenyl)-benzo[d]isothiazol-6-yl ester and 2-propyn-1-ol were converted to yield 3-[3-(4-Trifluoromethyl-phenyl)-benzo[d]isothiazol-6-yl]-prop-2-yn-1-ol as off-white solid, MS: 333(M).

14.3

In analogy to example 14.1, Trifluoro-methanesulfonic acid 3-(4-trifluoromethyl-phenyl)-benzo[d]isothiazol-6-yl ester and 3-butyn-1-ol were converted to yield 4-[3-(4-Trifluoromethyl-phenyl)-benzo[d]isothiazol-6-yl]-but-3-yn-1-ol as orange semisolid, MS: 347 (M).

14.4

In analogy to example 14.1, Trifluoro-methanesulfonic acid 3-(4-chloro-phenyl)-benzo[d]isothiazol-6-yl ester and 2-propyn-1-ol were converted to yield 3-[3-(4-Chloro-phenyl)-benzo[d]isothiazol-6-yl]-prop-2-yn-1-ol as yellow solid, MS: 299 (M, 1 Cl).

14.5

In analogy to example 14.1, Trifluoro-methanesulfonic acid 3-(4-chloro-phenyl)-benzo[d]isothiazol-6-yl ester and 3-butyn-1-ol were converted to yield 4-[3-(4-Chloro-phenyl)-benzo[d]isothiazol-6-yl]-but-3-yn-1-ol as yellow solid, mp: 128–129° C., MS: 313 (M, 1 Cl).

14.6

In analogy to example 14.1, Trifluoro-methanesulfonic acid 3-(4-chloro-phenyl)-benzo[d]isothiazol-6-yl ester and 4-pentyn-1-ol were converted to yield 5-[3-(4-Chloro-phenyl)-benzo[d]isothiazol-6-yl]-pent-4-yn-1-ol as yellow oil, MS: 327 (M, 1 Cl).

Example 15

15.1

365 mg (1.02 mmol) 4-[3-(4-Bromo-phenyl)-benzo[d]isothiazol-6-yl]-but-3-yn-1-ol in 7 ml CH$_2$Cl$_2$ were treated with 94 µl (1.21 mmol) methane sulfonic acid chloride, 0.13 ml (1.53 mmol) pyridine and 135 mg (1.2 mmol) DMAP at 0° C. The solution was stirred at RT over night, was diluted with water and acidified with 10% aq. KHSO$_4$. The inorganic phase was extracted with CH$_2$Cl$_2$. The combined organic phases were washed with NaHCO$_3$ solution, brine and dried over Na$_2$SO$_4$. Evaporation gave 446 mg crude Methanesulfonic acid 4-[3-(4-bromo-phenyl)-benzo[d]isothiazol-6-yl]-but-3-ynyl ester, MS: 436 (MH$^+$).

15.2

In analogy to example 15.1, 3-[3-(4-Bromo-phenyl)-benzo[d]isothiazol-6-yl]-prop-2-yn-1-ol and methane sulfonyl chloride were converted to yield Methanesulfonic acid 3-[3-(4-bromo-phenyl)-benzo[d]isothiazol-6-yl]-prop-2-ynyl ester, which was directly subjected to the following reaction.

15.3

In analogy to example 15.1, 5-[3-(4-Bromo-phenyl)-benzo[d]isothiazol-6-yl]-pent-4-yn-1-ol and methane sulfonyl chloride were converted to yield Methanesulfonic acid 5-[3-(4-bromo-phenyl)-benzo[d]isothiazol-6-yl]-pent-4-ynyl ester, MS: 450 (MH$^+$, 1Br).

15.4

In analogy to example 15.1, 3-[3-(4-Trifluoromethyl-phenyl)-benzo[d]isothiazol-6-yl]-prop-2-yn-1-ol and methane sulfonyl chloride were converted to yield Methanesulfonic acid 3-[3-(4-trifluoromethyl-phenyl)-benzo[d]isothiazol-6-yl]-prop-2-ynyl ester, which was directly subjected to the following reaction.

15.5

In analogy to example 15.1, 5-[3-(4-Trifluoromethyl-phenyl)-benzo[d]isothiazol-6-yl]-pent-4-yn-1H-ol and methane sulfonyl chloride were converted to yield Methanesulfonic acid 5-[3-(4-trifluoromethyl-phenyl)-benzo[d]isothiazol-6-yl]-pent-4-ynyl ester light brown oil, MS: 369 (M).

15.6

In analogy to example 15.1, 3-[3-(4-Chloro-phenyl)-benzo[d]isothiazol-6-yl-prop-2-yn-1-ol and methane sulfonyl chloride were converted to yield Methanesulfonic acid 3-[3-(4-chloro-phenyl)-benzo[d]isothiazol-6-yl]-prop-2-ynyl ester as a brown oil, MS: 377 (M, 1Cl).

15.7

In analogy to example 15.1, 4-[3-(4-Chloro-phenyl)-benzo[d]isothiazol-6-yl]-but-3-yn-1-ol and methane sulfonyl chloride were converted to yield Methanesulfonic acid 4-[3-(4-chloro-phenyl)-benzo[d]isothiazol-6-yl]-but-3-ynyl ester as a light yellow oil, MS: 391 (M, 1Cl).

15.8

In analogy to example 15.1, 5-[3-(4-Chloro-phenyl)-benzo[d]isothiazol-6-yl]-pent-4-yn-1-ol and methane sulfonyl chloride were converted to yield Methanesulfonic acid 5-[3-(4-chloro-phenyl)-benzo[d]isothiazol-6-yl]-pent-4-ynyl ester as a light yellow oil, MS: 405 (M, 1Cl).

Example 16

16.1

73 mg (0.16 mmol) Methanesulfonic acid 4-[3-(4-bromo-phenyl)-benzo[d]isothiazol-6-yl]-but-3-ynyl ester in 1 ml DMA were treated with 35 µl (0.5 mmol) azetidine for 48 h. The solution was diluted with ether and aqueous $Na_2CO_3$, the phases were separated and the inorganic layer was extracted with ether. The combined organic phases were washed with brine, dried over $Na_2SO_4$. Column chromatography on silica gel with a gradient $CH_2Cl_2$ to $CH_2Cl_2$:MeOH 8:1 gave 22.2 mg (33%) 6-(4-Azetidin-1-yl-but-1-ynyl)-3-(4-bromo-phenyl)-benzo[d]isothiazole as brown oil, MS: 397($MH^+$, 1Br).

16.2

In analogy to example 16.1, Methanesulfonic acid 4-[3-(4-bromo-phenyl)-benzo[d]isothiazol-6-yl]-but-3-ynyl ester and 2-(Methylamino)ethanol were converted to yield 2-({4-[3-(4-Bromo-phenyl)-benzo[d]isothiazol-6-yl]-but-3-ynyl}-methyl-amino)-ethanol as brown oil, MS: 415($MH^+$, 1Br).

16.3

In analogy to example 16.1, Methanesulfonic acid 5-[3-(4-bromo-phenyl)-benzo[d]isothiazol-6-yl]-pent-4-ynyl ester and Allylmethylamine were converted to yield Allyl-{5-[3-(4-bromo-phenyl)-benzo[d]isothiazol-6-yl]-pent-4-ynyl}-methyl-amine as light yellow solid, MS: 425 ($MH^+$, 1Br).

16.4

In analogy to example 16.1, Methanesulfonic acid 5-[3-(4-bromo-phenyl)-benzo[d]isothiazol-6-yl]-pent-4-ynyl ester and 2-Methylaminoethanol were converted to yield 2-({5-[3-(4-Bromo-phenyl)-benzo[d]isothiazol-6-yl]-pent-4-ynyl}-methyl-amino)-ethanol as off-white semisolid, MS: 429($MH^+$, 1Br).

16.5

In analogy to example 16.1, Methanesulfonic acid 5-[3-(4-bromo-phenyl)-benzo[d]isothiazol-6-yl]-pent-4-ynyl ester and 2-Ethylaminoethanol were converted to yield 2-({5-[3-(4-Bromo-phenyl)-benzo[d]isothiazol-6-yl]-pent-4-ynyl}-ethyl-amino)-ethanol as off-white semisolid, MS: 443 ($MH^+$, 1Br).

16.6

In analogy to example 16.1, Methanesulfonic acid 5-[3-(4-bromo-phenyl)-benzo[d]isothiazol-6-yl]-pent-4-ynyl ester and N-(2-Methoxyethyl)methylamine were converted to yield {5-[3-(4-Bromo-phenyl)-benzo[d]isothiazol-6-yl]-pent-4-ynyl-(2-methoxy-ethyl)-methyl-amine as off-white semisolid, MS: 443 ($MH^+$, 1Br).

16.7

In analogy to example 16.1, Methanesulfonic acid 5-[3-(4-bromo-phenyl)-benzo[d]isothiazol-6-yl]-pent-4-ynyl ester and Dimethylamine were converted to yield {5-[3-(4-Bromo-phenyl)-benzo[d]isothiazol-6-yl]-pent-4-ynyl}-dimethyl-amine as off-white semisolid, MS: 399 ($MH^+$, 1Br).

16.8

In analogy to example 16.1, Methanesulfonic acid 5-[3-(4-bromo-phenyl)-benzo[d]isothiazol-6-yl]-pent-4-ynyl ester and azetidine were converted to yield 6-(5-Azetidin-1-yl-pent-1-ynyl)-3-(4-bromo-phenyl)-benzo[d]isothiazole as orange semisolid, MS: 411 ($MH^+$, 1Br).

16.9

In analogy to example 16.1, Methanesulfonic acid 3-[3-(4-chloro-phenyl)-benzo[d]isothiazol-6-yl]-prop-2-ynyl ester and Allylmethylamine (2×2 equivalents) were converted to yield Allyl-{3-[3-(4-chloro-phenyl)-benzo[d]isothiazol-6-yl]-prop-2-ynyl}-methyl-amine as brown oil, MS: 353 ($MH^+$, 1Cl).

16.10

In analogy to example 16.1, Methanesulfonic acid 3-[3-(4-chloro-phenyl)-benzo[d]isothiazol-6-yl]-prop-2-ynyl ester and 2-Ethylaminoethanol (2×2 equivalents) were converted to yield 2-({3-[3-(4-Chloro-phenyl)-benzo[d]isothiazol-6-yl]-prop-2-ynyl}-ethyl-amino)-ethanol, MS: 371 ($MH^+$, 1Cl).

16.11

In analogy to example 16.1, Methanesulfonic acid 3-[3-(4-chloro-phenyl)-benzo[d]isothiazol-6-yl]-prop-2-ynyl ester and Diethanolamine (2×2 equivalents) were converted to yield 2-[{3-[3-(4-Chloro-phenyl)-benzo[d]isothiazol-6-yl]-prop-2-ynyl}-(2-hydroxy-ethyl)-amino]-ethanol as white solid, MS: 387 ($MH^+$, 1Cl).

16.12

In analogy to example 16.1, Methanesulfonic acid 3-[3-(4-chloro-phenyl)-benzo[d]isothiazol-6-yl]-prop-2-ynyl ester and Dimethylamine (10 equivalents of a 5.6 M EtOH solution) were converted to yield {13-[3-(4-Chloro-phenyl)-benzo[d]isothiazol-6yl]-prop-2-ynyl}-dimethyl-amine as light brown solid, MS: 327 ($MH^+$, 1Cl).

Example 17

17.1

150 mg (0.34 mmol) Methanesulfonic acid 5-[3-(4-trifluoromethyl-phenyl)-benzo[d]isothiazol-6-yl]-pent-4-ynyl ester in 1.5 ml DMF were treated with 140 µl (1.7 mmol) N-allylmethylamine at 50° C. for 4 h. The solution was diluted with ether and water, the organic phase was washed with 0.5 M NaOH, and dried over $Na_2SO_4$. Column chromatography on silica gel gave 80 mg (56%) 2-(Methyl-{5-[3-(4-trifluoromethyl-phenyl)-benzo[d]isothiazol-6-yl]-pent-4-ynyl}-amino)-ethanol as light yellow, MS: 419 ($MH^+$).

17.2

In analogy to example 17.1, Methanesulfonic acid 3-[3-(4-bromo-phenyl)-benzo[d]isothiazol-6-yl]-prop-2-ynyl ester and 2-methylaminoethanol were converted to yield 2-({3-[3-(4-Bromo-phenyl)-benzo[d]isothiazol-6-yl]-prop-2-ynyl-methyl-amino)-ethanol as light brown semisolid, MS: 401($MH^+$, 1Br).

17.3

In analogy to example 17.1, Methanesulfonic acid 3-[3-(4-bromo-phenyl)-benzo[d]isothiazol-6-yl]-prop-2-ynyl ester and 2-ethylaminoethanol were converted to yield 2-({3-[3-(4-Bromo-phenyl)-benzo[d]isothiazol-6-yl]-prop-2-ynyl}-ethyl-amino)-ethanol as light brown semisolid, MS: 415($MH^+$, 1Br).

17.4

In analogy to example 17.1, Methanesulfonic acid 5-[3-(4-trifluoromethyl-phenyl)-benzo[d]isothiazol-6-yl]-pent-4-ynyl ester and N-allylmethylamine were converted to yield Allyl-methyl-{5-[3-(4-trifluoromethyl-phenyl)-benzo[d]isothiazol-6-yl]-pent-4-ynyl}-amine as light yellow oil, MS: 415($MH^+$).

17.5

In analogy to example 17.1, Methanesulfonic acid 5-[3-(4-trifluoromethyl-phenyl)-benzo[d]isothiazol-6-yl]-pent-4-ynyl ester and 2-Methoxyethylmethylamine were converted to yield (2-Methoxy-ethyl)-methyl-{5-[3-(4-trifluoromethyl-phenyl)-benzo[d]isothiazol-6-yl]-pent-4-ynyl}-amine as orange oil, MS: 433 ($MH^+$).

17.6

In analogy to example 17.1, Methanesulfonic acid 5-[3-(4-trifluoromethyl-phenyl)-benzo[d]isothiazol-6-yl]-pent-4-ynyl ester and dimethylamine were converted to yield Dimethyl-{5-[3-(4-trifluoromethyl-phenyl)-benzo[d]isothiazol-6-yl]-pent-4-ynyl}-amine as off-white solid, MS: 389 (MH+).

17.7

In analogy to example 17.1, Methanesulfonic acid 5-[3-(4-trifluoromethyl-phenyl)-benzo[d]isothiazol-6-yl]-pent-4-ynyl ester and 2-Ethylaminoethanol were converted to yield 2-(Ethyl-{5-[3-(4-trifluoromethyl-phenyl)-benzo[d]isothiazol-6-yl]-pent-4-ynyl}-amino)-ethanol as light yellow oil, MS: 433 (MH+).

17.8

In analogy to example 17.1, Methanesulfonic acid 5-[3-(4-trifluoromethyl-phenyl)-benzo[d]isothiazol-6-yl]-pent-4-ynyl ester and azetidine were converted to yield 6-(5-Azetidin-1-yl-pent-1-ynyl)-3-(4-trifluoromethyl-phenyl)-benzo[d]isothiazole as orange oil, MS: 401 (MH+).

17.9

In analogy to example 17.1, Methanesulfonic acid 3-[3-(4-trifluoromethyl-phenyl)-benzo[d]isothiazol-6-yl]-prop-2-ynyl ester and 2-Methylaminoethanol were converted to yield 2-(Methyl-{3-[3-(4-trifluoromethyl-phenyl)-benzo[d]isothiazol-6-yl]-prop-2-ynyl}-amino)-ethanol as light brown oil, MS: 391 (MH+).

17.10

In analogy to example 17.1, Methanesulfonic acid 3-[3-(4-trifluoromethyl-phenyl)-benzo[d]isothiazol-6-yl]-prop-2-ynyl ester and 2-ethylaminoethanol were converted to yield 2-(Ethyl-{3-[3-(4-trifluoromethyl-phenyl)-benzo[d]isothiazol-6-yl]-prop-2-ynyl}-amino)-ethanol as light brown oil, MS: 405 (MH+).

17.11

In analogy to example 17.1, Methanesulfonic acid 3-[3-(4-trifluoromethyl-phenyl)-benzo[d]isothiazol-6-yl]-prop-2-ynyl ester and N-allylmethylamine were converted to yield Allyl-methyl-{3-[3-(4-trifluoromethyl-phenyl)-benzo[d]isothiazol-6-yl]-prop-2-ynyl}-amine as orange oil, MS: 387 (MH+).

17.12

In analogy to example 17.1, Methanesulfonic acid 3-[3-(4-trifluoromethyl-phenyl)-benzo[d]isothiazol-6-yl]-prop-2-ynyl ester and azetidine were converted to yield 6-(3-Azetidin-1-yl-prop-1-ynyl)-3-(4-trifluoromethyl-phenyl)-benzo[d]isothiazole as light brown oil, MS: 373 (MH+).

17.13

In analogy to example 17.1, Methanesulfonic acid 3-[3-(4-trifluoromethyl-phenyl)-benzo[d]isothiazol-6-yl]-prop-2-ynyl ester and 2-Methoxyethylmethylamine were converted to yield (2-Methoxy-ethyl)-methyl-{3-[3-(4-trifluoromethyl-phenyl)-benzo[d]isothiazol-6-yl]-prop-2-ynyl}-amine as light brown oil, MS: 405 (MH+).

17.14

In analogy to example 17.1, Methanesulfonic acid 3-[3-(4-trifluoromethyl-phenyl)-benzo[d]isothiazol-6-yl]-prop-2-ynyl ester and Dimethylamine were converted to yield Dimethyl-{3-[3-(4-trifluoromethyl-phenyl)-benzo[d]isothiazol-6-yl]-prop-2-ynyl}-amine as light brown oil, MS: 361 (MH+).

Example 18

A solution of 0.25 mmol (1 equivalent) of the corresponding methanesulfonic acid in 0.7 ml dry DMA was treated with a solution of 0.5 mmol (2 equivalents) of the corresponding secondary amine in 0.15 ml dry DMA at room temperature. After 16 h, 2 equivalents of secondary amine were added again to the solution. The reaction mixture was allowed to stand over night at room temperature, treated with 0.2 ml formic acid and purified by preparative HPLC [RP-18, acetonitrile (0.1% HCOOH)/water (0.1% HCOOH), 10% to 95% acetonitrile]. After evaporation, the product was obtained as a mixture of amino formate and methanesulfonate.

18.1

According to the method in example 18, Methanesulfonic acid 5-[3-(4-chloro-phenyl)-benzo[d]isothiazol-6-yl]-pent-4-ynyl ester and N-Dimethylamine were converted to yield {5-[3-(4-Chloro-phenyl)-benzo[d]isothiazol-6-yl]-pent-4-ynyl}-dimethyl-amine, MS: 355 (MH+).

18.2

According to the method in example 18, Methanesulfonic acid 5-[3-(4-chloro-phenyl)-benzo[d]isothiazol-6-yl]-pent-4-ynyl ester and Piperidine were converted to yield 3-(4-Chloro-phenyl)-6-(5-piperidin-1-yl-pent-1-ynyl)-benzo[d]isothiazole, MS: 395 (MH+).

18.3

According to the method in example 18, Methanesulfonic acid 5-[3-(4-chloro-phenyl)-benzo[d]isothiazol-6-yl]-pent-4-ynyl ester and Azetidine were converted to yield 6-(5-Azetidin-1-yl-pent-1-ynyl)-3-(4-chloro-phenyl)-benzo[d]isothiazole, MS: 367 (MH+).

18.4

According to the method in example 18, Methanesulfonic acid 5-[3-(4-chloro-phenyl)-benzo[d]isothiazol-6-yl]-pent-4-ynyl ester and N-Methylallylamine were converted to yield Allyl-{5-[3-(4-chloro-phenyl)-benzo[d]isothiazol-6-yl]-pent-4-ynyl}-methyl-amine, MS: 381 (MH+).

18.5

According to the method in example 18, Methanesulfonic acid 5-[3-(4-chloro-phenyl)-benzo[d]isothiazol-6-yl]-pent-4-ynyl ester and Diethylamine were converted to yield {5-[3-(4-Chloro-phenyl)-benzo[d]isothiazol-6-yl]-pent-4-ynyl}-diethyl-amine, MS: 383 (MH+).

18.6

According to the method in example 18, Methanesulfonic acid 5-[3-(4-chloro-phenyl)-benzo[d]isothiazol-6-yl]-pent-4-ynyl ester and Diethanolamine were converted to yield 2-[{5-[3-(4-Chloro-phenyl)-benzo[d]isothiazol-6-yl]-pent-4-ynyl}-(2-hydroxy-ethyl)-amino]-ethanol, MS: 415 (MH+).

18.7

According to the method in example 18, Methanesulfonic acid 5-[3-(4-chloro-phenyl)-benzo[d]isothiazol-6-yl]-pent-4-ynyl ester and 2-(Ethylamino)ethanol were converted to yield 2-({5-[3-(4-Chloro-phenyl)-benzo[d]isothiazol-6-yl]-pent-4-ynyl}-ethyl-amino)-ethanol, MS: 399 (MH+).

Example 19

19.1

100 mg (0.28 mmol) ) 4-[3-(4-Bromo-phenyl)-benzo[d]isothiazol-6-yl]-but-3-yn-1-ol in 2 ml CH$_2$Cl$_2$ were treated with 53 µl (0.31 mmol) Huenig's base at 51 µl (0.31 mmol)

trifluoromethane sulfonic acid anhydride at −15° C. The solution was stirred at that temperature for 1 h, additional 10 μl trifluoromethane sulfonic acid anhydride were added and stirring continued for 1 h. 48 μl (0.28 mmol) Huenig's base and 75 μl (0.84 mmol) N-(2-Methoxyethyl)methylamine were added at −15° C. The solution was warmed to RT and stirred for 1.5 h. The solution was diluted with CH$_2$Cl$_2$ and washed with Na$_2$CO$_3$ solution, brine and dried with Na$_2$SO$_4$. Column chromatography gave 66.1 mg (56%) {4-[3-(4-Bromo-phenyl)-benzo[d]isothiazol-6-yl]-but-3-ynyl}-(2-methoxy-ethyl)-methyl-amine as brown oil, MS: 429 (MH$^+$, 1Br).

19.2

In analogy to example 19.1, 4-[3-(4-Bromo-phenyl)-benzo[d]isothiazol-6-yl]-but-3-yn-1-ol and Dimethylamine were converted to yield {4-[3-(4-Bromo-phenyl)-benzo[d]isothiazol-6-yl]-but-3-ynyl}-dimethyl-amine as light brown semisolid, MS: 385 (MH$^+$, 1Br).

19.3

In analogy to example 19.1, 4-[3-(4-Bromo-phenyl)-benzo[d]isothiazol-6-yl]-but-3-yn-1-ol and N-Allylmethylamine were converted to yield Allyl-{4-[3-(4-bromo-phenyl)-benzo[d]isothiazol-6-yl]-but-3-ynyl}-methyl-amine as brown oil, MS: 411 (MH$^+$, 1Br).

19.4

In analogy to example 19.1, 4-[3-(4-Bromo-phenyl)-benzo[d]isothiazol-6-yl]-but-3-yn-1-ol and 2-(Ethylamino) ethanol were converted to yield 2-({4-[3-(4-Bromo-phenyl)-benzo[d]isothiazol-6-yl]-but-3-ynyl}-ethyl-amino)-ethanol as brown oil, MS: 429 (MH$^+$, 1Br).

19.5

In analogy to example 19.1, 4-[3-(4-Trifluoromethyl-phenyl)-benzo[d]isothiazol-6-yl]-but-3-yn-1-ol and Dimethylamine were converted to yield Dimethyl-{4-[3-(4-trifluoromethyl-phenyl)-benzo[d]isothiazol-6-yl]-but-3-ynyl}-amine as brown oil, MS: 375 (MH$^+$).

19.6

In analogy to example 19.1, 4-[3-(4-Trifluoromethyl-phenyl)-benzo[d]isothiazol-6-yl]-but-3-yn-1-ol and N-allylmethylamine were converted to yield Allyl-methyl-{4-[3-(4-trifluoromethyl-phenyl)-benzo[d]isothiazol-6-yl]-but-3-ynyl}-amine as yellow oil, MS: 401 (MH$^+$).

19.7

In analogy to example 19.1, 4-[3-(4-Trifluoromethyl-phenyl)-benzo[d]isothiazol-6-yl]-but-3-yn-1-ol and 2-Ethylaminoethanol were converted to yield 2-(Ethyl-{4-[3-(4-trifluoromethyl-phenyl)-benzo[d]isothiazol-6-yl]-but-3-ynyl}-amino)-ethanol as light yellow oil, MS: 419 (MH$^+$).

19.8

In analogy to example 19.1, 4-[3-(4-Trifluoromethyl-phenyl)-benzo[d]isothiazol-6-yl]-but-3-yn-1-ol and 2-Methylaminoethanol were converted to yield 2-(Methyl-{4-[3-(4-trifluoromethyl-phenyl)-benzo[d]isothiazol-6-yl]-but-3-ynyl}-amino)-ethanol as yellow oil, MS: 405 (MH$^+$).

19.9

In analogy to example 19.1, 4-[3-(4-Trifluoromethyl-phenyl)-benzo[d]isothiazol-6-yl]-but-3-yn-1-ol and 2-Methoxyethylmethylamine were converted to yield (2-Methoxy-ethyl)-methyl-{4-[3-(4-trifluoromethyl-phenyl)-benzo[d]isothiazol-6-yl]-but-3-ynyl}-amine as light brown oil, MS: 419 (MH$^+$).

19.10

In analogy to example 19.1, 4-[3-(4-Chloro-phenyl)-benzo[d]isothiazol-6-yl]-but-3-yn-1-ol and 2-Ethylaminoethanol were converted to yield 2-({4-[3-(4-Chloro-phenyl)-benzo[d]isothiazol-6-yl]-but-3-ynyl}-ethyl-amino)-ethanol as light yellow oil, MS: 358 (MH$^+$, 1Cl).

Example 20

20.1

500 mg (1.5 mmol) 3-[3-(4-Trifluoromethyl-phenyl)-benzo[d]isothiazol-6-yl]-prop-2-yn-1-ol in 25 ml MeOH were hydrogenated in the presence of 120 mg PtO$_2$. H$_2$O, filtration over silica gel and evaporation yielded 360 mg (71%) 3-[3-(4-Trifluoromethyl-phenyl)-benzo[d]isothiazol-6-yl]-propan-1-ol, which was directly subjected to the following reaction.

20.2

In analogy to example 20.1, 4-[3-(4-Trifluoromethyl-phenyl)-benzo[d]isothiazol-6-yl]-but-3-yn-1-ol was converted to yield 4-[3-(4-Trifluoromethyl-phenyl)-benzo[d]isothiazol-6-yl]-butan-1-ol, MS: 351 (M).

20.3

In analogy to example 20.1, Methanesulfonic acid 4-[3-(4-chloro-phenyl)-benzo[d]isothiazol-6-yl]-but-3-ynyl ester in EtOH/dioxane was converted to yield Methanesulfonic acid 4-[3-(4-chloro-phenyl)-benzo[d]isothiazol-6-yl]-butyl ester as a dark brown oil, MS: 396 (MH$^+$, 1Cl).

20.4

In analogy to example 20.1, 3-[3-(4-Chloro-phenyl)-benzo[d]isothiazol-6-yl]-prop-2-yn-1-ol in EtOH/dioxane was converted to yield 3-[3-(4-Chloro-phenyl)-benzo[d]isothiazol-6-yl]-propan-1-ol as a brown oil, MS: 303 (M, 1Cl).

20.5

In analogy to example 20.1, 4-[3-(4-Bromo-phenyl)-benzo[d]isothiazol-6-yl]-but-3-yn-1-ol was converted to yield 4-[3-(4-Bromo-phenyl)-benzo[d]isothiazol-6-yl]-butan-1-ol as yellow oil, MS: 361 (M, 1Br).

Example 21

21.1

360 mg (1.07 mmol) 3-[3-(4-Trifluoromethyl-phenyl)-benzo[d]isothiazol-6-yl]-propan-1-ol in 3 ml CH$_2$Cl$_2$ were treated with 100 μl (1.29 mmol) methanesulfonic acid chloride and 450 μl (3.23 mmol) triethylamine at 0° C. The solution was stirred at RT for 2 h, diluted with CH$_2$Cl$_2$ and washed with 1N HCl and dried over Na$_2$SO$_4$. Evaporation gave 350 mg (79%) crude Methanesulfonic acid 3-[3-(4-trifluoromethyl-phenyl)-benzo[d]isothiazol-6-yl]-propyl ester, which was directly subjected to the following reaction.

21.2

In analogy to example 21.1, 4-[3-(4-Trifluoromethyl-phenyl)-benzo[d]isothiazol-6-yl]-butan-1-ol and methanesulfonic acid chloride were converted to yield Methanesulfonic acid 4-[3-(4-trifluoromethyl-phenyl)-benzo[d]isothiazol-6-yl]-butyl ester, MS: 430 (MH$^+$).

21.3

In analogy to example 21.1, 3-[3-(4-Chloro-phenyl)-benzo[d]isothiazol-6-yl]-propan-1-ol and methanesulfonic acid chloride were converted to Methanesulfonic acid 3-[3-(4-chloro-phenyl)-benzo[d]isothiazol-6-yl]-propyl ester as a orange oil, MS: 381 (M, 1Cl)

Example 22

22.1

In analogy to example 17.1; Methanesulfonic acid 3-[3-(4-trifluoromethyl-phenyl)-benzo[d]isothiazol-6-yl]-propyl ester and 2-ethylaminoethanol were converted to yield 2-(Ethyl-{3-[3-(4-trifluoromethyl-phenyl)-benzo[d]isothiazol-6-yl]-propyl}-amino)-ethanol as light brown oil, MS: 409 (MH$^+$).

22.2

In analogy to example 17.1; Methanesulfonic acid 3-[3-(4-trifluoromethyl-phenyl)-benzo[d]isothiazol-6-yl]-propyl ester and Dimethylamine were converted to yield Dimethyl-{3-[3-(4-trifluoromethyl-phenyl)-benzo[d]isothiazol-6-yl]-propyl}-amine as light brown oil, MS: 365 (MH$^+$).

22.3

In analogy to example 17.1; Methanesulfonic acid 3-[3-(4-trifluoromethyl-phenyl)-benzo[d]isothiazol-6-yl]-propyl ester and 2-Methylaminoethanol were converted to yield 2-(Methyl-{3-[3-(4-trifluoromethyl-phenyl)-benzo[d]isothiazol-6-yl]-propyl}-amino)-ethanol as light brown oil, MS: 395 (MH$^+$).

22.4

In analogy to example 17.1; Methanesulfonic acid 4-[3-(4-trifluoromethyl-phenyl)-benzo[d]isothiazol-6-yl]-butyl ester and 2-Ethylaminoethanol were converted to yield 2-(Ethyl-{4-[3-(4-trifluoromethyl-phenyl)-benzo[d]isothiazol-6-yl]-butyl}-amino)-ethanol as light yellow oil, MS: 423 (MH$^+$).

22.5

In analogy to example 17.1; Methanesulfonic acid 4-[3-(4-trifluoromethyl-phenyl)-benzo[d]isothiazol-6-yl]-butyl ester and Dimethylamine were converted to yield Dimethyl-{4-[3-(4-trifluoromethyl-phenyl)-benzo[d]isothiazol-6-yl]-butyl}-amine as yellow oil, MS: 379 (MH$^+$).

22.6

In analogy to example 17.1; Methanesulfonic acid 4-[3-(4-trifluoromethyl-phenyl)-benzo[d]isothiazol-6-yl]-butyl ester and 2-Methylaminoethanol were converted to yield 2-(Methyl-{4-[3-(4-trifluoromethyl-phenyl)-benzo[d]isothiazol-6-yl]-butyl}-amino)-ethanol as light yellow oil, MS: 409 (MH$^+$).

22.7

In analogy to example 17.1; Methanesulfonic acid 3-[3-(4-chloro-phenyl)-benzo[d]isothiazol-6-yl]-propyl ester and 2-Ethylaminoethanol were converted to yield 2-({3-[3-(4-Chloro-phenyl)-benzo[d]isothiazol-6-yl]-propyl-ethyl-amino)-ethanol as yellow oil, MS: 375 (MH$^+$, 1Cl).

Example 23

A solution of 0.25 mmol (1 equivalent) of the corresponding methanesulfonic acid in 0.7 ml dry DMA was treated with a solution of 0.5 mmol (2 equivalents) of the corresponding secondary amine in 0.15 ml dry DMA at room temperature. After 16 h, 2 equivalents of secondary amine were added again to the solution. The reaction mixture was allowed to stand over night at room temperature, treated with 0.2 ml formic acid and purified by preparative HPLC [RP-18, acetonitrile (0.1% HCOOH)/water (0.1% HCOOH), 10% to 95% acetonitrile]. After evaporation, the product was obtained as a mixture of amino formate and methanesulfonate.

23.1

According to the method in example 23, Methanesulfonic acid 4-[3-(4-chloro-phenyl)-benzo[d]isothiazol-6-yl]-butyl ester and N-Methylallylamine were converted to yield Allyl-{4-[3-(4-chloro-phenyl)-benzo[d]isothiazol-6-yl]-butyl}-methyl-amine, MS: 371 (MH$^+$, 1Cl).

23.2

According to the method in example 23, Methanesulfonic acid 4-[3-(4-chloro-phenyl)-benzo[d]isothiazol-6-yl]-butyl ester and Diethylamine were converted to yield {4-[3-(4-Chloro-phenyl)-benzo[d]isothiazol-6-yl]-butyl}-diethyl-amine, MS: 373 (MH$^+$, 1Cl).

23.3

According to the method in example 23, Methanesulfonic acid 4-[3-(4-chloro-phenyl)-benzo[d]isothiazol-6-yl]-butyl ester and N-Methylpropylamine were converted to yield {4-[3-(4-Chloro-phenyl)-benzo[d]isothiazol-6-yl]-butyl}-methyl-propyl-amine, MS: 373 (MH$^+$, 1Cl).

23.4

According to the method in example 23, Methanesulfonic acid 4-[3-(4-chloro-phenyl)-benzo[d]isothiazol-6-yl]-butyl ester and Diethanolamin were converted to yield 2-[{4-[3-(4-Chloro-phenyl)-benzo[d]isothiazol-6-yl]-butyl}-(2-hydroxy-ethyl)-amino]-ethanol, MS: 405 (MH$^+$, 1Cl).

23.5

According to the method in example 23, Methanesulfonic acid 4-[3-(4-chloro-phenyl)-benzo[d]isothiazol-6-yl]-butyl ester and 2-Ethylaminoethanol were converted to yield 2-({4-[3-(4-Chloro-phenyl)-benzo[d]isothiazol-6-yl]-butyl}-ethyl-amino)-ethanol, MS: 389 (MH$^+$, 1Cl).

23.6

According to the method in example 23, Methanesulfonic acid 4-[3-(4-chloro-phenyl)-benzo[d]isothiazol-6-yl]-butyl ester and N-(2-Methoxyethyl)ethylamine were converted to yield {4-[3-(4-Chloro-phenyl)-benzo[d]isothiazol-6-yl]-butyl}-ethyl-(2-methoxy-ethyl)-amine, MS: 403 (MH$^+$, 1Cl).

23.7

According to the method in example 23, Methanesulfonic acid 4-[3-(4-chloro-phenyl)-benzo[d]isothiazol-6-yl]-butyl ester and Trimethyleneamine were converted to yield 6-(4-Azetidin-1-yl-butyl)-3-(4-chloro-phenyl)-benzo[d]isothiazole, MS: 357 (MH$^+$, 1Cl).

Example 24

24.1

Method A: 75 mg (0.2 mmol) 2-({3-[3-(4-Chloro-phenyl)-benzo[d]isothiazol-6-yl]-prop-2-ynyl}-ethyl-amino)-ethanol in 2 ml MeOH with 0.012 ml (0.2 mmol) AcOH were hydrogenated in the presence of 7 mg Pd/C$_{10}$% (16 h), filtration over decalite and evaporation yielded 58 mg (66%) Z-2-({3-[3-(4-Chloro-phenyl)-benzo[d]isothiazol-6-yl]-allyl}-ethyl-amino)-ethanol acetate as light brown oil, MS: 373 (MH$^+$, 1Cl).

24.2

Method B: 80 mg (0.25 mmol) {3-[3-(4-Chloro-phenyl)-benzo[d]isothiazol-6-yl]-prop-2-ynyl}-dimethyl-amine in 2 ml EtOH were hydrogenated in the presence of 20 mg PtO$_2$. H$_2$O , purification by flash silica gel column (CH$_2$Cl$_2$/MeOH 9:1) yielded 43 mg (53%) {3-[3-(4-Chloro-phenyl)-benzo[d]isothiazol-6-yl]-propyl}-dimethyl-amine as a colorless oil, MS: 331 (MH$^+$, 1Cl).

Example 25

25.1

10.09 g (70.5 mmol) 3-mercaptoanisole were added to a freshly prepared solution of 4.6 g (70.5 mmol) KOH in 75 ml ethanol and 30 ml water. Over a period of 30 min, 20.0 g (70.5 mmol) 2,4-dibromoacetophenone in 150 EtOAc were added at 0° C. and the solution was stirred at RT over night. The suspension was concentrated and dissolved in EtOAc and water. The inorganic phase was extracted with EtOAC, the combined organic phases were washed with water and brine and dried over $Na_2SO_4$. Evaporation yielded 25.1 g (quant) 1-(4-Bromo-phenyl)-2-(3-methoxy-phenylsulfanyl)-ethanone as white crystalline, MS: 336(M, 1Br). (In analogy to Jones, Charles D.; Jevnikar, Mary G.; Pike, Andrew J.; Peters, Mary K.; Black, Larry J.; Thompson, Allen R.; Falcone, Julie F.; Clemens, James A. Antiestrogens. 2. Structure-activity studies in a series of 3-aroyl-2-arylbenzo[b]thiophene derivatives leading to [6-hydroxy-2-(4-hydroxyphenyl)benzo[b]thien-3-yl]-[4-[2-(1-piperidinyl)ethoxy]phenyl]methanone hydrochloride (LY 156758), a remarkably effective estrogen antagonist with only minimal intrinsic estrogenicity. J. Med. Chem. (1984), 27(8), 1057–66.)

25.2

60 g polyphosphoric acid were heated to 80° C. 11.85 g (35.14 mmol) 1-(4-Bromo-phenyl)-2-(3-methoxy-phenylsulfanyl)-ethanone were added in small portions, keeping the temperature below 100° C. The reaction mixture was stirred at 85° C. for 2 h, cooled to 70° C. and added to ice water. The aqueous phase was extracted with EtOAc three times, the organic phase was washed with brine and dried over $Na_2SO_4$. The solid was crysallized from EtOAc-:MeOH to give 6.3 g (56%) 3-(4-Bromo-phenyl)-6-methoxy-benzo[b]thiophene as light yellow solid. MS: 318 (M, 1Br).

25.3

7.4 g (23.17 mmol) 3-(4-Bromo-phenyl)-6-methoxy-benzo[b]thiophene in 47 ml acetic acid were treated with 27 ml (62% aq) HBr at 125° C. for 4 h. The solution was concentrated in vacuo and the residue was dissolved in $NaHCO_3$ and EtOAc. Prior to extraction with EtOAc the pH was adjusted with 2M NaOH (pH 8). The combined organic phases were washed with brine and dried with $Na_2SO_4$. Trituration with hexane gave 6.96 g (98%) 3-(4-Bromo-phenyl)-benzo[b]thiophen-6-ol as light green solid, MS: 304 (M, 1Br).

Example 26

26.1

14.27 ml (115.0 mmol) 3-mercaptoanisole were added to a solution of 7.3 g (115.0 mmol) KOH in 120 ml ethanol and 50 ml water. 25.0 g (115.2 mmol) 4-fluorophenacyl bromide in 120 ml EtOAc were added slowly at 0° C. and the solution was stirred at RT over night. The suspension was concentrated and dissolved in EtOAc and water. The inorganic phase was extracted with EtOAc, the combined organic phases were washed with water and brine and dried over $Na_2SO_4$. Evaporation yielded 33.2 g crude 1-(4-Fluoro-phenyl)-2-(3-methoxy-phenylsulfanyl)-ethanone as light yellow liquid.

26.2

The crude product of experiment 26.1 was dissolved in toluene and evaporated three times prior to the reaction. To the resulting solid 305 ml (1.2 mol) $BF_3.Et_2O$ were added slowly and the solution was stirred at RT over night. This solution was added slowly to NaOH, and the pH was adjusted to pH 7. The solution was extracted with $CH_2Cl_2$, the organic phase was washed with brine and dried over $Na_2SO_4$, yielding 29.96 g crude 3-(4-Fluoro-phenyl)-6-methoxy-benzo[b]thiophene.

26.3

29.96 g 3-(4-Fluoro-phenyl)-6-methoxy-benzo[b]thiophene in 230 ml acetic acid were treated with 130 ml (62% aq) HBr at 125° C. for 4 h. The solution was added slowly to a cooled solution of 210 g NaOH in 600 ml water, the pH was adjusted to 8–9, and the inorganic phase was extracted with EtOAc. The combined organic phases were washed with brine and dried with $Na_2SO_4$. Column chromatography on silica gel with hexane:

EtOAc 4.1 yielded 20.0 g (73%) 3-(4-Fluoro-phenyl)-benzo[b]thiophen-6-ol as light brown solid, MS: 244(M).

26.4

In analogy to examples 26.1–26.3, 3-mercaptoanisole and 2,4'-dibromopropiophenone were converted to yield 3-(4-bromo-phenyl)-2-methyl-benzo[b]thiophen-6-ol as colorless amorphous solid, MS: 318 (M, 1Br).

26.5

In analogy to examples 26.1–26.3, 3-Mercaptoanisole and 2-Bromo-1-(4-trifluoromethyl-phenyl)-propan-1-one were converted to yield 2-Methyl-3-(4-trifluoromethyl-phenyl)-benzo[b]thiophen-6-ol as colorless amorphous solid, MS: 308 (M).

Example 27

27.1

2.0 g (6.55 mmol) 3-(4-Bromo-phenyl)-benzo[b]thiophen-6-ol in 25 ml acetone were treated with 5.89 g (42.6 mmol, 6.5 eq) $K_2CO_3$ and 2.0 ml (16.38 mmol, 2.5 eq) 1,4-dibromobutane. The reaction mixture was stirred at 45° C. for 10 h, filtered and evaporated. The excess of dibromide was removed in vacuo to yield 2.7 g crude 6-(4-Bromo-butoxy)-3-(4-bromo-phenyl)-benzo[b]thiophene, MS: 439 (M).

27.2

In analogy to example 27.1, 3-(4-Bromo-phenyl)-benzo[b]thiophen-6-ol and 1,3-dibromopropane were converted to yield 3-(4-Bromo-phenyl)-6-(3-bromo-propoxy)-benzo[b]thiophene, MS: 424 (M, 2Br).

27.3

In analogy to example 27.1, 3-(4-Fluoro-phenyl)-benzo[b]thiophen-6-ol and 1,3-dibromopropane were converted to yield 6-(3-Bromo-propoxy)-3-(4-fluoro-phenyl)-benzo[b]thiophene, MS: 364 (M, 1Br).

27.4

In analogy to example 27.1, 3-(4-Fluoro-phenyl)-benzo[b]thiophen-6-ol and 1,4-dibromobutane were converted to yield 6-(4-Bromo-butoxy)-3-(4-fluoro-phenyl)-benzo[b]thiophene, MS: 378 (M, 1Br).

27.5

In analogy to example 27.1, 3-(4-bromo-phenyl)-2-methyl-benzo[b]thiophen-6-ol and 1,4-dibromobutane were converted to yield 6-(4-bromo-butoxy)-3-(4-bromo-phenyl)-2-methyl-benzo[b]thiophene as colorless oil, MS: 452 (M, 2Br).

27.6

In analogy to example 27.1, 2-Methyl-3-(4-trifluoromethyl-phenyl)-benzo[b]thiophen-6-ol and 1,4-dibromobutane were converted to yield 6-(4-Bromo-butoxy)-2-methyl-3-(4-trifluoromethyl-phenyl)-benzo[b]thiophene as colorless oil, MS: 443 (MH$^+$, 1Br).

Example 28

28.1

In analogy to example 3.1, 2-(4-Bromo-butoxy)-3-(4-bromo-phenyl)-benzo[b]thiophene and N,N-dimethylamine in ethanol were converted to yield [4-[3-(4-Bromo-phenyl)-benzo[b]thiophen-6-yloxy]-butyl]-dimethyl-amine as light yellow semisolid, MS: 404 (MH$^+$, 1Br).

28.2

In analogy to example 3.1, 2-(4-Bromo-butoxy)-3-(4-bromo-phenyl)-benzo[b]thiophene and N-Allylmethylamine were converted to yield Allyl-[4-[3-(4-bromo-phenyl)-benzo[b]thiophen-6-yloxy]-butyl]-methyl-amine as light yellow oil, MS:
430(MH$^+$, 1Br).

28.3

In analogy to example 3.1, 3-(4-Bromo-phenyl)-6-(3-bromo-propoxy)-benzo[b]thiophene and diethanolamine were converted to yield 2-[{3-[3-(4-Bromo-phenyl)-benzo[b]thiophen-6-yloxy]-propyl}-(2-hydroxy-ethyl)-amino]-ethanol as light yellow oil, MS: 450 (MH$^+$, 1Br).

28.4

In analogy to example 3.1, 3-(4-Bromo-phenyl)-6-(3-bromo-propoxy)-benzo[b]thiophene and bis(2-methoxyethyl)amine were converted to yield {3-[3-(4-Bromo-phenyl)-benzo[b]thiophen-6-yloxy]-propyl}-bis-(2-methoxy-ethyl)-amine as light brown oil, MS: 478 (MH$^+$, 1Br).

Example 29

1 eq of the corresponding bromide was treated with 3 eq of the corresponding amine in DMA (4–10 ml/mmol bromide) at RT until no starting material could be detected with TLC. The solution was concentrated and the residue was redissolved in CH$_2$Cl$_2$/5% aqueous NaHCO$_3$. The phases were separated, and the inorganic phase was extracted with CH$_2$Cl$_2$, the combined organic phases were washed with brine, and were dried over Na$_2$SO$_4$. The crude material was purified by flash chromatography. To yield the corresponding hydrochlorides, the free amines were treated with HCl in MeOH.

29.1

According to the method in example 29, 6-(4-Bromo-butoxy)-3-(4-bromo-phenyl)-benzo[b]thiophene and 2-(methylamino)ethanol were converted to yield 2-({4-[3-(4-Bromo-phenyl)-benzo[b]thiophen-6-yloxy]-butyl}-methyl-amino)-ethanol-hydrochloride as light brown oil, MS: 434 (MH$^+$, 1Br).

29.2

According to the method in example 29, 6-(4-Bromo-butoxy)-3-(4-bromo-phenyl)-benzo[b]thiophene and N-(2-methoxyethyl)methylamine were converted to yield {4-[3-(4-Bromo-phenyl)-benzo[b]thiophen-6-yloxy]-butyl}-(2-methoxy-ethyl)-methyl-amine-hydrochloride as light brown semisolid, MS: 448 (MH$^+$, 1Br).

29.3

According to the method in example 29, 6-(4-Bromo-butoxy)-3-(4-bromo-phenyl)-benzo[b]thiophene and morpholine were converted to yield 4-{4-[3-(4-Bromo-phenyl)-benzo[b]thiophen-6-yloxy]-butyl}-morpholine-hydrochloride as light brown semisolid, MS: 446 (MH$^+$, 1Br).

29.4

According to the method in example 29, 6-(4-Bromo-butoxy)-3-(4-bromo-phenyl)-benzo[b]thiophene and 2-(ethylamino)ethanol were converted to yield 2-({4-[3-(4-Bromo-phenyl)-benzo[b]thiophen-6-yloxy]-butyl}-ethyl-amino)-ethanol-hydrochloride as orange oil, MS: 448 (MH$^+$, 1Br).

29.5

According to the method in example 29, 6-(4-Bromo-butoxy)-3-(4-bromo-phenyl)-benzo[b]thiophene and pyrrolidine were converted to yield 1-{4-[3-(4-Bromo-phenyl)-benzo[b]thiophen-6-yloxy]-butyl}-pyrrolidine-hydrochloride as grey semisolid, MS: 430 (MH$^+$, 1Br).

29.6

According to the method in example 29, 6-(4-Bromo-butoxy)-3-(4-bromo-phenyl)-benzo[b]thiophene and azetidine were converted to yield 1-{4-[3-(4-Bromo-phenyl)-benzo[b]thiophen-6-yloxy]-butyl}-azetidine-hydrochloride as light yellow oil, MS: 416 (MH$^+$, 1Br).

29.7

According to the method in example 29, 6-(4-Bromo-butoxy)-3-(4-bromo-phenyl)-benzo[b]thiophene and methylisopropylamine were converted to yield {4-[3-(4-Bromo-phenyl)-benzo[b]thiophen-6-yloxy]-butyl}-isopropyl-methyl-amine-hydrochloride as white foam, MS: 432 (MH$^+$, 1Br).

29.8

According to the method in example 29, 6-(4-Bromo-butoxy)-3-(4-bromo-phenyl)-benzo[b]thiophene and diethylamine were converted to yield 1{4-[3-(4-Bromo-phenyl)-benzo[b]thiophen-6-yloxy]-butyl}-diethyl-amine-hydrochloride as orange oil, MS: 432 (MH$^+$, 1Br).

29.9

According to the method in example 29, 6-(4-Bromo-butoxy)-3-(4-bromo-phenyl)-benzo[b]thiophene and diethanolamine were converted to yield 2-[{4-[3-(4-Bromo-phenyl)-benzo[b]thiophen-6-yloxy]-butyl}-(2-hydroxy-ethyl)-amino]-ethanol as light yellow oil, MS: 464 (MH$^+$,1Br).

29.10

According to the method in example 29,6-(4-Bromo-butoxy)-3-(4-bromo-phenyl)-benzo[b]thiophene and bis(2-methoxyethyl)amine were converted to yield {4-[3-(4-Bromo-phenyl)-benzo[b]thiophen-6-yloxy]-butyl}-bis-(2-methoxy-ethyl)-amine as light brown oil, MS: 492 (MH$^+$, 1Br).

Example 30

30.1

In analogy to example 3.1, 6-(3-Bromo-propoxy)-3-(4-fluoro-phenyl)-benzo[b]thiophene and N-allylmethylamine were converted to yield Allyl-{3-[3-(4-fluoro-phenyl)-benzo[b]thiophen-6-yloxy]-propyl}-methyl-amine as colorless oil, MS: 356 (MH$^+$).

30.2

In analogy to example 3.1, 6-(3-Bromo-propoxy)-3-(4-fluoro-phenyl)-benzo[b]thiophene and dimethylamine were converted to yield {3-[3-(4-Fluoro-phenyl)-benzo[b] thiophen-6-yloxy]-propyl}-dimethyl-amine as colorless oil, MS: 330 (MH⁺).

30.3

In analogy to example 3.1, 6-(3-Bromo-propoxy)-3-(4-fluoro-phenyl)-benzo[b]thiophene and 2-(methylamino) ethanol were converted to yield 2-({3-[3-(4-Fluoro-phenyl)-benzo[b]thiophen-6-yloxy]-propyl}-methyl-amino)-ethanol as colorless oil, MS: 360 (MH⁺).

30.4

In analogy to example 3.1, 6-(3-Bromo-propoxy)-3-(4-fluoro-phenyl)-benzo[b]thiophene and N-(2-methoxyethyl) methylamine were converted to yield {3-[3-(4-Fluoro-phenyl)-benzo[b]thiophen-6-yloxy]-propyl}-(2-methoxy-ethyl)-methyl-amine as colorless oil, MS: 374 (MH⁺).

30.5

In analogy to example 3.1, 6-(3-Bromo-propoxy)-3-(4-fluoro-phenyl)-benzo[b]thiophene and 2-(ethylamino) ethanol were converted to yield 2-(Ethyl-{3-[3-(4-fluoro-phenyl)-benzo[b]thiophen-6-yloxy]-propyl}-amino)-ethanol as colorless oil, MS: 374 (MH⁺).

30.6

In analogy to example 3.1, 6-(3-Bromo-propoxy)-3-(4-fluoro-phenyl)-benzo[b]thiophene and N-(2-methoxyethyl) ethylamine were converted to yield Ethyl-{3-[3-(4-fluoro-phenyl)-benzo[b]thiophen-6-yloxy]-propyl}-(2-methoxy-ethyl)-amine as colorless oil, MS: 388 (MH⁺).

30.7

In analogy to example 3.1, 6-(3-Bromo-propoxy)-3-(4-fluoro-phenyl)-benzo[b]thiophene and diethanolamine were converted to yield 2-[{3-[3-(4-Fluoro-phenyl)-benzo[b] thiophen-6-yloxy]-propyl}-(2-hydroxy-ethyl)-amino]-ethanol as colorless oil, MS: 390 (MH⁺).

30.8

In analogy to example 3.1, 6-(3-Bromo-propoxy)-3-(4-fluoro-phenyl)-benzo[b]thiophene and bis(2-methoxyethyl) amine were converted to yield {3-[3-(4-Fluoro-phenyl)-benzo[b]thiophen-6-yloxy]-propyl}-bis-(2-methoxy-ethyl)-amine as colorless oil, MS: 418 (MH⁺).

30.9

In analogy to example 3.1, 6-(3-Bromo-propoxy)-3-(4-fluoro-phenyl)-benzo[b]thiophene and pyrrolidine were converted to yield 1-{3-[3-(4-Fluoro-phenyl)-benzo[b] thiophen-6-yloxy]-propyl-pyrrolidine as colorless oil, MS: 356 (MH⁺).

30.10

In analogy to example 3.1, 6-(3-Bromo-propoxy)-3-(4-fluoro-phenyl)-benzo[b]thiophene and azetidine were converted to yield 1-{3-[3-(4-Fluoro-phenyl)-benzo[b] thiophen-6-yloxy]-propyl}-azetidine as colorless oil, MS: 342 (MH⁺).

30.11

In analogy to example 3.1, 6-(4-Bromo-butoxy)-3-(4-fluoro-phenyl)-benzo[b]thiophene and N-allylmethylamine were converted to yield Allyl-{4-[3-(4-fluoro-phenyl)-benzo [b]thiophen-6-yloxy]-butyl}-methyl-amine as colorless oil, MS: 370 (MH⁺).

30.12

In analogy to example 3.1, 6-(4-Bromo-butoxy)-3-(4-fluoro-phenyl)-benzo[b]thiophene and dimethylamine were converted to yield 1{4-[3-(4-Fluoro-phenyl)-benzo[b] thiophen-6-yloxy]-butyl}-dimethyl-amine as white semisolid, MS: 344 (MH⁺).

30.13

In analogy to example 3.1, 6-(4-Bromo-butoxy)-3-(4-fluoro-phenyl)-benzo[b]thiophene and 2-(methylamino) ethanol were converted to yield 2-({4-[3-(4-Fluoro-phenyl)-benzo[b]thiophen-6-yloxy]-butyl}-methyl-amino)-ethanol as colorless oil, MS: 374 (MH⁺).

30.14

In analogy to example 3.1, 6-(4-Bromo-butoxy)-3-(4-fluoro-phenyl)-benzo[b]thiophene and N-(2-methoxyethyl) methylamine were converted to yield {4-[3-(4-Fluoro-phenyl)-benzo[b]thiophen-6-yloxy]-butyl}-(2-methoxy-ethyl)-methyl-amine as colorless oil, MS: 388 (MH⁺).

30.15

In analogy to example 3.1, 6-(4-Bromo-butoxy)-3-(4-fluoro-phenyl)-benzo[b]thiophene and 2-(ethylamino) ethanol were converted to yield 2-(Ethyl-{4-[3-(4-fluoro-phenyl)-benzo[b]thiophen-6-yloxy]-butyl}-amino)-ethanol as colorless oil, MS: 388 (MH⁺).

30.16

In analogy to example 3.1, 6-(4-Bromo-butoxy)-3-(4-fluoro-phenyl)-benzo[b]thiophene and N-(2-methoxyethyl) ethylamine were converted to yield Ethyl-{4-[3-(4-fluoro-phenyl)-benzo[b]thiophen-6-yloxy]-butyl}-(2-methoxy-ethyl)-amine as colorless oil, MS: 402 (MH⁺).

30.17

In analogy to example 3.1, 6-(4-Bromo-butoxy)-3-(4-fluoro-phenyl)-benzo[b]thiophene and diethanolamine were converted to yield 2-[{4-[3-(4-Fluoro-phenyl)-benzo[b] thiophen-6-yloxy]-butyl}-(2-hydroxy-ethyl)-amino]-ethanol as white semisolid, MS: 404 (MH⁺).

30.18

In analogy to example 3.1, 6-(4-Bromo-butoxy)-3-(4-fluoro-phenyl)-benzo[b]thiophene and bis(2-methoxyethyl) amine were converted to yield {4-[3-(4-Fluoro-phenyl)-benzo[b]thiophen-6-yloxy]-butyl}-bis-(2-methoxy-ethyl)-amine as colorless oil, MS: 432 (MH⁺).

30.19

In analogy to example 3.1, 6-(4-Bromo-butoxy)-3-(4-fluoro-phenyl)-benzo[b]thiophene and pyrrolidine were converted to yield 1-{4-[3-(4-Fluoro-phenyl)-benzo[b] thiophen-6-yloxy]-butyl}-pyrrolidine as white semisolid, MS: 370 (MH⁺).

30.20

In analogy to example 3.1, 6-(4-Bromo-butoxy)-3-(4-fluoro-phenyl)-benzo[b]thiophene and azetidine were converted to yield 1-{4-[3-(4-Fluoro-phenyl)-benzo[b] thiophen-6-yloxy]-butyl}-azetidine as colorless oil, MS: 356 (MH⁺).

Example 31

A solution of 0.25 mmol (1 equivalent) of the corresponding bromide in 0.7 ml dry DMA was treated with a solution of 0.5 mmol (2 equivalents) of the corresponding secondary amine in 0.15 ml dry DMA at room temperature. After 16 h, additional 2 equivalents of secondary amine were added to the solution. The reaction mixture was allowed to stand over night at room temperature, treated with 0.2 ml formic acid and purified by preparative HPLC [RP-18, acetonitrile (0.1% HCOOH)/water (0.1% HCOOH), 10% to 95% acetonitrile]. After evaporation, the product was obtained as a mixture of amino hydrobromide and formate.

31.1

According to the method in example 31, 6-(4-Bromo-butoxy)-3-(4-bromo-phenyl)-2-methyl-benzo[b]thiophene and Allyl-methyl-amine were converted to yield Allyl-{4-[3-(4-bromo-phenyl)-2-methyl-benzo[b]thiophen-6-yloxy]-butyl}-methyl-amine, MS: 444 (MH$^+$, 1Br).

31.2

According to the method in example 31, 6-(4-Bromo-butoxy)-3-(4-bromo-phenyl)-2-methyl-benzo[b]thiophene and Dimethylamine were converted to yield {4-[3-(4-Bromo-phenyl)-2-methyl-benzo[b]thiophen-6-yloxy]-butyl}-dimethyl-amine, MS: 418 (MH$^+$, 1Br).

31.3

According to the method in example 31, 6-(4-Bromo-butoxy)-3-(4-bromo-phenyl)-2-methyl-benzo[b]thiophene and Ethyl-(2-hydroxy-ethyl)-amine were converted to yield 2-({4-[3-(4-Bromo-phenyl)-2-methyl-benzo[b]thiophen-6-yloxy]-butyl}-ethyl-amino)-ethanol, MS: 462 (MH$^+$, 1Br).

31.4

According to the method in example 31, 6-(4-Bromo-butoxy)-3-(4-bromo-phenyl)-2-methyl-benzo[b]thiophene and Diethylamine were converted to yield {4-[3-(4-Bromo-phenyl)-2-methyl-benzo[b]thiophen-6-yloxy]-butyl}-diethyl-amine, MS: 446 (MH$^+$, 1Br).

31.5

According to the method in example 31, 6-(4-Bromo-butoxy)-3-(4-bromo-phenyl)-2-methyl-benzo[b]thiophene and piperidine were converted to yield 1-{4-[3-(4-Bromo-phenyl)-2-methyl-benzo[b]thiophen-6-yloxy]-butyl}-piperidine, MS: 458 (MH$^+$, 1Br).

31.6

According to the method in example 31, 6-(4-Bromo-butoxy)-3-(4-bromo-phenyl)-2-methyl-benzo[b]thiophene and Azetidine were converted to yield 1-{4-[3-(4-Bromo-phenyl)-2-methyl-benzo[b]thiophen-6-yloxy]-butyl}-azetidine, MS: 430 (MH$^+$, 1Br).

31.7

According to the method in example 31, 6-(4-Bromo-butoxy)-3-(4-bromo-phenyl)-2-methyl-benzo[b]thiophene and 2-(hydroxy-ethyl)-amino-ethanol were converted to yield 2-[{4-[3-(4-Bromo-phenyl)-2-methyl-benzo[b]thiophen-6-yloxy]-butyl}-(2-hydroxy-ethyl)-amino]-ethanol, MS: 478 (MH$^+$, 1Br).

31.8

According to the method in example 31, 6-(4-Bromo-butoxy)-2-methyl-3-(4-trifluoromethyl-phenyl)-benzo[b]thiophene and 4-hydroxy-piperidine were converted to yield 1-{4-[2-Methyl-3-(4-trifluoromethyl-phenyl)-benzo[b]thiophen-6-yloxy]-butyl}-piperidin-4-ol as yellowish oil, MS: 464 (MH$^+$).

31.9

According to the method in example 31, 6-(4-Bromo-butoxy)-2-methyl-3-(4-trifluoromethyl-phenyl)-benzo[b]thiophene and N-propyl amine were converted to yield {4-[2-Methyl-3-(4-trifluoromethyl-phenyl)-benzo[b]thiophen-6-yloxy]-butyl}-propyl-amine as yellowish oil, MS: 422 (MH$^+$).

31.10

According to the method in example 31, 6-(4-Bromo-butoxy)-2-methyl-3-(4-trifluoromethyl-phenyl)-benzo[b]thiophene and ethanolamine were converted to yield 2-{4-[2-Methyl-3-(4-trifluoromethyl-phenyl)-benzo[b]thiophen-6-yloxy]-butylamino}-ethanol as colorless amorphous solid, MS: 424 (MH$^+$).

31.11

According to the method in example 31, 6-(4-Bromo-butoxy)-2-methyl-3-(4-trifluoromethyl-phenyl)-benzo[b]thiophene and 2-ethylamino-ethanol were converted to yield 2-(Ethyl-{4-[2-methyl-3-(4-trifluoromethyl-phenyl)-benzo[b]thiophen-6-yloxy]-butyl}-amino)-ethanol as yellowish oil, MS: 452 (MH$^+$).

31.12

According to the method in example 31, 6-(4-Bromo-butoxy)-2-methyl-3-(4-trifluoromethyl-phenyl)-benzo[b]thiophene and N-allyl-methylamine were converted to yield Allyl-methyl-{4-[2-methyl-3-(4-trifluoromethyl-phenyl)-benzo[b]thiophen-6-yloxy]-butyl}-amine as yellowish oil, MS: 434 (MH$^+$).

31.13

According to the method in example 31, 6-(4-Bromo-butoxy)-2-methyl-3-(4-trifluoromethyl-phenyl)-benzo[b]thiophene and piperidine were converted to yield 1-{4-[2-Methyl-3-(4-trifluoromethyl-phenyl)-benzo[b]thiophen-6-yloxy]-butyl}-piperidine as yellowish oil, MS: 448 (MH$^+$).

31.14

According to the method in example 31, 6-(4-Bromo-butoxy)-3-(4-bromo-phenyl)-2-methyl-benzo[b]thiophene and N-(2-methoxy-ethyl)-ethylamine were converted to yield {4-[3-(4-Bromo-phenyl)-2-methyl-benzo[b]thiophen-6-yloxy]-butyl}-ethyl-(2-methoxy-ethyl)-amine as yellowish oil, MS: 476 (MH$^+$, 1Br).

31.15

According to the method in example 31, 6-(4-Bromo-butoxy)-3-(4-bromo-phenyl)-2-methyl-benzo[b]thiophene and dimethylamine were converted to yield {4-[3-(4-Bromo-phenyl)-2-methyl-benzo[b]thiophen-6-yloxy]-butyl}-dimethyl-amine as yellowish oil, MS: 418 (MH$^+$, 1Br).

Example 32

32.1

1.3 g (2.95 mmol) 6-(4-Bromo-butoxy)-3-(4-bromo-phenyl)-benzo[b]thiophene in 140 ml acetic acid were warmed to 50° C. and 1.36 g (8.9 mmol) sodium perborate were added in portions. The reaction mixture was stirred at that temperature for 18 h, concentrated and dissolved in water, and extracted with EtOAc and $CH_2Cl_2$. The combined organic phases were washed with brine and dried over $Na_2SO_4$. Column chromatography on silica gel with EtOAc:hexane 1:4 yielded 802 mg (67%) 6-(4-Bromo-butoxy)-3-(4-bromo-phenyl)-benzo[b]thiophene 1,1-dioxide as light yellow solid, MS: 472 (MH$^+$, 1Br).

32.2

In analogy to example 32.1, 3-(4-Bromo-phenyl)-6-(3-bromo-propoxy)-benzo[b]thiophene was converted to yield 3-(4-Bromo-phenyl)-6-(3-bromo-propoxy)-benzo[b]thiophene 1,1-dioxide as light yellow solid, MS: 458 (MH$^+$, 1Br).

32.3

In analogy to example 32.1, 6-(4-bromo-butoxy)-3-(4-bromo-phenyl)-2-methyl-benzo[b]thiophene was converted to yield 6-(4-bromo-butoxy)-3-(4-bromo-phenyl)-2-methyl-benzo[b]thiophene 1,1-dioxide as colorless solid, MS: 484 (M, 2Br).

32.4

In analogy to example 32.1, 6-(4-Bromo-butoxy)-2-methyl-3-(4-trifluoromethyl-phenyl)-benzo[b]thiophene was converted to yield 6-(4-Bromo-butoxy)-2-methyl-3-(4-trifluoromethyl-phenyl)-benzo[b]thiophene 1,1-dioxide as colorless solid, MS: 475 (MH$^+$, 1Br).

Example 33

1 eq of the corresponding bromide was treated with 3 eq of the corresponding amine in DMA (4–10 ml/mmol bromide) at RT until no starting material could be detected with TLC. The solution was concentrated and the residue was redissolved in CH$_2$Cl$_2$/5% aqueous NaHCO$_3$. The phases were separated, and the inorganic phase was extracted with CH$_2$Cl$_2$, the combined organic phases were washed with brine, and were dried over Na$_2$SO$_4$. The crude material was purified by flash chromatography. To yield the corresponding hydrochlorides, the free amines were treated with HCl in MeOH.

33.1

According to the method in example 33, 3-(4-Bromo-phenyl)-6-(3-bromo-propoxy)-benzo[b]thiophene 1,1-dioxide and N-Allylmethylamine were converted to yield Allyl-{3-[3-(4-bromo-phenyl)-1,1-dioxo-1H-11 6-benzo[b]thiophen-6-yloxy]-propyl}-methyl-amine as light yellow solid, MS: 448(MH$^+$, 1Br).

33.2

According to the method in example 33, 3-(4-Bromo-phenyl)-6-(3-bromo-propoxy)-benzo[b]thiophene 1,1-dioxide and Dimethylamine were converted to yield {3-[3-(4-Bromo-phenyl)-1,1-dioxo-1H-11 6-benzo[b]thiophen-6-yloxy]-propyl}-dimethyl-amine as off-white solid, MS: 422 (MH$^+$, 1Br).

33.3

According to the method in example 33, 3-(4-Bromo-phenyl)-6-(3-bromo-propoxy)-benzo[b]thiophene 1,1-dioxide and N-Methylaminoethanol were converted to yield 2-({3-[3-(4-Bromo-phenyl)-1,1-dioxo-1H-11 6-benzo[b]thiophen-6-yloxy]-propyl}-methyl-amino)-ethanol as off-white semisolid, MS: 452 (MH$^+$, 1Br).

33.4

According to the method in example 33, 3-(4-Bromo-phenyl)-6-(3-bromo-propoxy)-benzo[b]thiophene 1,1-dioxide and N-Ethylaminoethanol were converted to yield 2-({3-[3-(4-Bromo-phenyl)-1,1-dioxo-1H-11 6-benzo[b]thiophen-6-yloxy]-propyl}-ethyl-amino)-ethanol as light yellow semisolid, MS: 466(MH$^+$, 1Br).

33.5

According to the method in example 33, 3-(4-Bromo-phenyl)-6-(3-bromo-propoxy)-benzo[b]thiophene 1,1-dioxide and N-(2-Methoxyethyl)methylamine were converted to yield {3-[3-(4-Bromo-phenyl)-1,1-dioxo-1H-11 6-benzo[b]thiophen-6-yloxy]-propyl}-(2-methoxy-ethyl)-methyl-amine as off-white solid, MS: 466 (MH$^+$, 1Br).

33.6

According to the method in example 33, 3-(4-Bromo-phenyl)-6-(3-bromo-propoxy)-benzo[b]thiophene 1,1-dioxide and azetidine were converted to yield 1-{3-[3-(4-Bromo-phenyl)-1,1-dioxo-1H-11 6-benzo[b]thiophen-6-yloxy]-propyl}-azetidine as off-white solid, MS: 434 (MH$^+$, 1Br).

33.7

According to the method in example 33, 6-(4-Bromo-butoxy)-3-(4-bromo-phenyl)-benzo[b]thiophene 1,1-dioxide and N-Allylmethylamine were converted to yield Allyl-{4-[3-(4-bromo-phenyl)-1,1-dioxo-1H-11 6-benzo[b]thiophen-6-yloxy]-butyl}-methyl-amine as off-white semisolid, MS: 462 (MH$^+$, 1Br).

33.8

According to the method in example 33, 6-(4-Bromo-butoxy)-3-(4-bromo-phenyl)-benzo[b]thiophene 1,1-dioxide and Dimethylamine were converted to yield {4-[3-(4-Bromo-phenyl)-1,1-dioxo-1H-11 6-benzo[b]thiophen-6-yloxy]-butyl}-dimethyl-amine as light yellow semisolid, MS: 436 (MH$^+$, 1Br).

33.9

According to the method in example 33, 6-(4-Bromo-butoxy)-3-(4-bromo-phenyl)-benzo[b]thiophene 1,1-dioxide and N-Methylaminoethanol were converted to yield 2-({4-[3-(4-Bromo-phenyl)-1,1-dioxo-1H-11 6-benzo[b]thiophen-6-yloxy]-butyl}-methyl-amino)-ethanol as off-white solid, MS: 466 (MH$^+$, 1Br).

33.10

According to the method in example 33, 6-(4-Bromo-butoxy)-3-(4-bromo-phenyl)-benzo[b]thiophene 1,1-dioxide and N-Ethylaminoethanol were converted to yield 2-({4-[3-(4-Bromo-phenyl)-1,1-dioxo-1H-11 6-benzo[b]thiophen-6-yloxy]-butyl}-ethyl-amino)-ethanol as off-white solid, MS: 480 (MH$^+$, 1Br).

33.11

According to the method in example 33, 6-(4-Bromo-butoxy)-3-(4-bromo-phenyl)-benzo[b]thiophene 1,1-dioxide and N-(2-Methoxyethyl)methylamine were converted to yield {4-[3-(4-Bromo-phenyl)-1,1-dioxo-1H-11 6-benzo[b]thiophen-6-yloxy]-butyl}-(2-methoxy-ethyl)-methyl-amine as light yellow semisolid, MS: 480 (MH$^+$, 1Br).

33.12

According to the method in example 33, 6-(4-Bromo-butoxy)-3-(4-bromo-phenyl)-benzo[b]thiophene 1,1-dioxide and azetidine were converted to yield 1-{4-[3-(4-Bromo-phenyl)-1,1-dioxo-1H-11 6-benzo[b]thiophen-6-yloxy]-butyl}-azetidine as off-white solid, MS: 434 (MH$^+$, 1Br).

Example 34

A solution of 0.25 mmol (1 equivalent) of the corresponding bromide in 0.7 ml dry DMA was treated with a solution of 0.5 mmol (2 equivalents) of the corresponding secondary amine in 0.15 ml dry DMA at room temperature. After 16 h, additional 2 equivalents of secondary amine were added to the solution. The reaction mixture was allowed to stand over night at room temperature, treated with 0.2 ml formic acid and purified by preparative HPLC [RP-18, acetonitrile (0.1% HCOOH)/water (0.1% HCOOH), 10% to 95% acetonitrile]. After evaporation, the product was obtained as a mixture of amino hydrobromide and formate.

34.1

According to the method in example 34, 6-(4-Bromo-butoxy)-3-(4-bromo-phenyl)-2-methyl-benzo[b]thiophene 1,1-dioxide and N-Methylallylamine were converted to yield Allyl-{4-[3-(4-bromo-phenyl)-2-methyl-1,1-dioxo-1H-11 6-benzo[b]thiophen-6-yloxy]-butyl}-methyl-amine, MS: 476 (MH$^+$, 1Br).

34.2

According to the method in example 34, 6-(4-Bromo-butoxy)-3-(4-bromo-phenyl)-2-methyl-benzo[b]thiophene 1,1-dioxide and Diethylamine were converted to yield {4-[3-(4-Bromo-phenyl)-2-methyl-1,1-dioxo-1H-11 6-benzo[b]thiophen-6-yloxy]-butyl}-diethyl-amine, MS: 478 (MH$^+$, 1Br).

34.3

According to the method in example 34, 6-(4-Bromo-butoxy)-3-(4-bromo-phenyl)-2-methyl-benzo[b]thiophene 1,1-dioxide and N-Methylpropylamine were converted to yield {4-[3-(4-Bromo-phenyl)-2-methyl-1,1-dioxo-1H-11 6-benzo[b]thiophen-6-yloxy]-butyl}-methyl-propyl-amine, MS: 478 (MH$^+$, 1Br).

34.4

According to the method in example 34, 6-(4-Bromo-butoxy)-3-(4-bromo-phenyl)-2-methyl-benzo[b]thiophene 1,1-dioxide and Diethanolamine were converted to yield 2-[{4-[3-(4-Bromo-phenyl)-2-methyl-1,1-dioxo-1H-11 6-benzo[b]thiophen-6-yloxy]-butyl}-(2-hydroxy-ethyl)-amino]-ethanol, MS: 510 (MH$^+$, 1Br).

34.5

According to the method in example 34, 6-(4-Bromo-butoxy)-3-(4-bromo-phenyl)-2-methyl-benzo[b]thiophene 1,1-dioxide and 2-Ethylaminoethanol were converted to yield 2-({4-[3-(4-Bromo-phenyl)-2-methyl-1,1-dioxo-1H-11 6-benzo[b]thiophen-6-yloxy]-butyl}-ethyl-amino)-ethanol, MS: 494 (MH$^+$, 1Br).

34.6

According to the method in example 34, 6-(4-Bromo-butoxy)-3-(4-bromo-phenyl)-2-methyl-benzo[b]thiophene 1,1-dioxide and N-(2-Methoxyethyl)ethylamine were converted to yield {4-[3-(4-Bromo-phenyl)-2-methyl-1,1-dioxo-1H-11 6-benzo[b]thiophen-6-yloxy]-butyl}-ethyl-(2-methoxy-ethyl)-amine, MS: 508 (MH$^+$, 1Br).

34.7

According to the method in example 34, 6-(4-Bromo-butoxy)-3-(4-bromo-phenyl)-2-methyl-benzo[b]thiophene 1,1-dioxide and Trimethyleneamine were converted to yield 1-{4-[3-(4-Bromo-phenyl)-2-methyl-1,1-dioxo-1H-11 6-benzo[b]thiophen-6-yloxy]-butyl}-azetidine, MS: 462 (MH$^+$, 1Br).

34.8

According to the method in example 34, 6-(4-Bromo-butoxy)-2-methyl-3-(4-trifluoromethyl-phenyl)-benzo[b]thiophene 1,1-dioxide and 2-ethylamino-ethanol were converted to yield 2-(Ethyl-{4-[2-methyl-1,1-dioxo-3-(4-trifluoromethyl-phenyl)-1H-11 6-benzo[b]thiophen-6-yloxy]-butyl}-amino)-ethanol as colorless oil, MS: 484 (MH$^+$).

34.9

According to the method in example 34, 6-(4-Bromo-butoxy)-2-methyl-3-(4-trifluoromethyl-phenyl)-benzo[b]thiophene 1,1-dioxide and diethylamine were converted to yield Diethyl-{4-[2-methyl-1,1-dioxo-3-(4-trifluoromethyl-phenyl)-1H-11 6-benzo[b]thiophen-6-yloxy]-butyl}-amine as yellowish solid, MS: 468 (MH$^+$).

34.10

According to the method in example 34, 6-(4-Bromo-butoxy)-2-methyl-3-(4-trifluoromethyl-phenyl)-benzo[b]thiophene 1,1-dioxide and N-methyl propyl-amine were converted to yield Methyl-{4-[2-methyl-1,1-dioxo-3-(4-trifluoromethyl-phenyl)-1H-11 6-benzo[b]thiophen-6-yloxy]-butyl}-propyl-amine as yellowish oil, MS: 468 (MH$^+$).

34.11

According to the method in example 34, 6-(4-Bromo-butoxy)-2-methyl-3-(4-trifluoromethyl-phenyl)-benzo[b]thiophene 1,1-dioxide and N-(2-methoxy-ethyl) ethyl-amine were converted to yield Ethyl-(2-methoxy-ethyl)-{4-[2-methyl-1,1-dioxo-3-(4-trifluoromethyl-phenyl)-1H-11 6-benzo[b]thiophen-6-yloxy]-butyl}-amine as yellowish oil, MS: 498 (MH$^+$).

34.12

According to the method in example 34, 6-(4-Bromo-butoxy)-2-methyl-3-(4-trifluoromethyl-phenyl)-benzo[b]thiophene 1,1-dioxide and diethanol-amine were converted to yield 2-((2-Hydroxy-ethyl)-{4-[2-methyl-1,1-dioxo-3-(4-trifluoromethyl-phenyl)-1H-11 6-benzo[b]thiophen-6-yloxy]-butyl}-amino)-ethanol as colorless oil, MS: 500 (MH$^+$).

Example 35

35.1

To 7.0 g (15.6 mmol) 2-({4-[3-(4-Bromo-phenyl)-benzo[d]isothiazol-6-yloxy]-butyl}-ethyl-amino)-ethanol in 20 ml DMF were added 1.9 g (28.0 mmol, 1.8 eq) imidazole, followed by 3.3 g (21.8 mmol, 1.4 eq) tert-butyldimethylchlorosilane in 20 ml DMF at 0° C.

The solution was stirred at 50° C. for 6 h, and at RT for 48 h. Additional 235 mg (1.5 mmol, 0.1 eq) tert-butyldimethylchlorosilane were added and the solution was stirred at 50° C. for 2 h. The solution was poured on an aqueous solution of NaHCO$_3$. The inorganic layer was extracted with ether, and the combined organic phases were washed with brine and dried over Na$_2$SO$_4$. Column chromatography on silica gel with CH$_2$Cl$_2$:MeOH 95:5 gave 6.5 g (74%) {4-[3-(4-Bromo-phenyl)-benzo[d]isothiazol-6-yloxy]-butyl}-[2-(tert-butyl-dimethyl-silanyloxy)-ethyl]-ethyl-amine as brown oil, MS: 563 (MH$^+$, 1Br).

35.2

Under argon a flask was charged with 26.0 mg (0.03 mmol, 0.05 eq) tris(Dibenzylideneacetone) dipalladium, 16.9 mg (0.06 mmol, 0.1 eq) 2(di-tertbutylphosphino) biphenyl and 92.8 mg (0.97 mmol, 1.7 eq) sodium tert-butylate, evacuated and backfilled with argon. 320 mg (0.57 mmol) 4-[3-(4-Bromo-phenyl)-benzo[d]isothiazol-6-yloxy]-butyl}-[2-(tert-butyl-dimethyl-silanyloxy)-ethyl]-ethyl-amine in 3 ml toluene were added, followed by a solution of 0.14 ml (1.4 mmol, 2.5 eq) piperidine in 3 ml toluene. The solution was heated to 80° C. for 2d. The mixture was diluted with EtOAc and a saturated solution of Na$_2$CO$_3$ was added. The inorganic layer was extracted with EtOAc. The combined organic phases were washed with brine and dried over Na$_2$SO$_4$. Column chromatography yielded 248 mg (77%) [2-(tert-Butyl-dimethyl-silanyloxy)-ethyl]-ethyl-{4-[3-(4-piperidin-1-yl-phenyl)-benzo[d]isothiazol-6-yloxy]-butyl}-amine as yellow oil, MS: 568 (MH$^+$).

35.3

In analogy to example 35.2, 4-[3-(4-Bromo-phenyl)-benzo[d]isothiazol-6-yloxy]-butyl}-[2-(tert-butyl-dimethyl-silanyloxy)-ethyl]-ethyl-amine and Morpholine were converted to yield [2-(tert-Butyl-dimethyl-silanyloxy)-ethyl]- ethyl-{4-[3-(4-morpholin-4-yl-phenyl)-benzo[d]isothiazol-6-yloxy]-butyl}-amine as yellow oil, MS: 570 (MH+).

35.4

In analogy to example 35.2, 4-[3-(4-Bromo-phenyl)-benzo[d]isothiazol-6-yloxy]-butyl}-[2-(tert-butyl-dimethyl-silanyloxy)-ethyl]-ethyl-amine and N-Methylaniline were converted to yield {4-[6-(4-{[2-(tert-Butyl-dimethyl-silanyloxy)-ethyl]-ethyl-amino}-butoxy)-benzo[d]isothiazol-3-yl]-phenyl}-methyl-phenyl-amine as yellow oil, MS: 590 (MH+).

35.5

In analogy to example 35.2, 4-[3-(4-Bromo-phenyl)-benzo[d]isothiazol-6-yloxy]-butyl}-[2-(tert-butyl-dimethyl-silanyloxy)-ethyl]-ethyl-amine and piperazine were converted to yield [2-(tert-Butyl-dimethyl-silanyloxy)-ethyl]-ethyl-{4-[3-(4-piperazin-1-yl-phenyl)-benzo[d]isothiazol-6-yloxy]-butyl}-amine as orange oil, MS: 569 (MH+).

35.6

In analogy to example 35.2, 4-[3-(4-Bromo-phenyl)-benzo[d]isothiazol-6-yloxy]-butyl}-[2-(tert-butyl-dimethyl-silanyloxy)-ethyl]-ethyl-amine and 1-acetylpiperazine were converted to yield 1-(4-{4-[6-(4-{[2-(tert-Butyl-dimethyl-silanyloxy)-ethyl]-ethyl-amino}-butoxy)-benzo[d]isothiazol-3-yl]-phenyl}-piperazin-1-yl)-ethanone as orange oil, MS: 611 (MH+).

35.7

In analogy to example 35.2, 4-[3-(4-Bromo-phenyl)-benzo[d]isothiazol-6-yloxy]-butyl}-[2-(tert-butyl-dimethyl-silanyloxy)-ethyl]-ethyl-amine and benzylamine were converted to yield Benzyl-{4-[6-(4-{[2-(tert-Butyl-dimethyl-silanyloxy)-ethyl]-ethyl-amino}-butoxy)-benzo[d]isothiazol-3-yl]-phenyl}-amine as orange oil, MS: 590 (MH+).

35.8

220 mg (0.39 mmol) [2-(tert-Butyl-dimethyl-silanyloxy)-ethyl]-ethyl-{4-[3-(4-piperidin-1-yl-phenyl)-benzo[d]isothiazol-6-yloxy]-butyl}-amine in 5 ml THF were treated with 0.6 ml 1M TBAF in THF for 1 h at RT. The solution was concentrated and the crude product subjected to column chromatography on silica gel with CH$_2$Cl$_2$:MeOH 9:1 to give 146 mg (83%) 2-(Ethyl-{4-[3-(4-piperidin-1-yl-phenyl)-benzo[d]isothiazol-6-yloxy]-butyl}-amino)-ethanol as yellow oil, MS: 454 (MH+).

35.9

In analogy to example 35.8, [2-(tert-Butyl-dimethyl-silanyloxy)-ethyl]-ethyl-{4-[3-(4-morpholin-4-yl-phenyl)-benzo[d]isothiazol-6-yloxy]-butyl}-amine were converted to yield 2-(Ethyl-{4-[3-(4-morpholin-4-yl-phenyl)-benzo[d]isothiazol-6-yloxy]-butyl}-amino)-ethanol as yellow oil, MS: 456 (MH+).

35.10

In analogy to example 35.8, {4-[6-(4-{[2-(tert-Butyl-dimethyl-silanyloxy)-ethyl]-ethyl-amino}-butoxy)-benzo[d]isothiazol-3-yl]-phenyl}-methyl-phenyl-amine were converted to yield 2-[Ethyl-(4-{3-[4-(methyl-phenyl-amino)-phenyl]-benzo[d]isothiazol-6-yloxy}-butyl)-amino]-ethanol as yellow oil, MS: 476 (MH+).

35.11

In analogy to example 35.8, [2-(tert-Butyl-dimethyl-silanyloxy)-ethyl]-ethyl-{4-[3-(4-piperazin-1-yl-phenyl)-benzo[d]isothiazol-6-yloxy]-butyl}-amine were converted to yield 2-(Ethyl-{4-[3-(4-piperazin-1-yl-phenyl)-benzo[d]isothiazol-6-yloxy]-butyl}-amino)-ethanol as colorless oil, MS: 455 (MH+).

35.12

In analogy to example 35.8, 1-(4-{4-[6-(4-{[2-(tert-Butyl-dimethyl-silanyloxy)-ethyl]-ethyl-amino}-butoxy)-benzo[d]isothiazol-3-yl]-phenyl-piperazin-1-yl)-ethanone were converted to yield 1-{4-[4-(6-{4-[Ethyl-(2-hydroxy-ethyl)-amino]-butoxy}-benzo[d]isothiazol-3-yl)-phenyl]-piperazin-1-yl}-ethanone as colorless oil, MS: 497 (MH+).

35.13

In analogy to example 35.8, Benzyl-{4-[6-(4-{[2-(tert-butyl-dimethyl-silanyloxy)-ethyl-amino}-butoxy)-benzo[d]isothiazol-3-yl]-phenyl]-amine were converted to yield 2-({4-[3-(4-Benzylamino-phenyl)-benzo[d]isothiazol-6-yloxy]-butyl}-ethyl-amino)-ethanol as yellow oil, MS: 476 (MH+).

35.14

Under argon a flask was charged with 20.3 mg (0.02 mmol, 0.05 eq) tris(dibenzylideneacetone) dipalladium, 13.2 mg (0.04 mmol, 0.1 eq) 2(di-tertbutylphosphino)biphenyl and 38.7 mg (0.89 mmol, 2 eq) sodium hydride (55% in mineral oil), evacuated and backfilled with argon. 250 mg (0.44 mmol) 4-[3-(4-Bromo-phenyl)-benzo[d]isothiazol-6-yloxy]-butyl}-[2-(tert-butyl-dimethyl-silanyloxy)-ethyl]-ethyl-amine in 4 ml toluene were added, followed by a solution of 0.031 ml (0.75 mmol, 1.7 eq) methanol in 2 ml toluene. The solution was heated to 80° C. for 2d. The mixture was diluted with EtOAc and a saturated solution of Na$_2$CO$_3$. The inorganic layer was extracted with EtOAc. The combined organic phases were washed with brine and dried over Na$_2$SO$_4$. Column chromatography on silica gel with CH$_2$Cl$_2$:MeOH 95:5 yielded 174 mg light yellow oil which was dissolved in 5 ml THF and was treated with with 0.53 ml 1M Bu$_4$NF in THF at RT for 1 h. The solution was concentrated and the residue purified by column chromatography to yield 2-{Ethyl-[4-(3-phenyl-benzo[d]isothiazol-6-yloxy)-butyl]-amino}-ethanol as light yellow oil, MS: 371 (MH+).

35.15

Under argon a flask was charged with 10.0 mg (0.01 mmol, 0.03 eq) tris(dibenzylideneacetone) dipalladium, 10 mg (0.02 mmol, 0.05 eq) R(+) 2,2'-Bis(diphenylphosphino)-1,1'-Binaphtyl and 47.7 mg (0.5 mmol, 1.4 eq) sodium tert-butylate, evacuated and backfilled with argon. 200 mg (0.35 mmol) 4-[3-(4-Bromo-phenyl)-benzo[d]isothiazol-6-yloxy]-butyl}-[2-(tert-butyl-dimethyl-silanyloxy)-ethyl]-ethyl-amine in 4 ml toluene were added, followed by a solution of 0.071 ml (0.4 mmol, 1.2 eq) benzophenone imine in 2 ml toluene. The solution was heated to 80° C. over night. The mixture was diluted with EtOAc and water. The inorganic layer was extracted with EtOAc. The combined organic phases were washed with brine and dried over Na$_2$SO$_4$.

The residue was dissolved in 2 ml MeOH, 10 mg 10% Pd/C and 336 mg (5.3 mmol) ammonium formate were added and the reaction mixture was stirred at 60° C. for 3 h. Additional ammonium formate was added in portions until no starting material could be detected. The solution was filtered over decalite and evaporated.

The crude product was dissolved in 1.5 ml THF and was treated with 0.24 ml 1M Bu$_4$NF in THF at RT for 1 h. The solution was concentrated and the residue purified by ion exchange chromatography to yield 40 mg (29%, 3 steps) 2-({4-[3-(4-Amino-phenyl)-benzo[d]isothiazol-6-yloxy]-butyl}-ethyl-amino)-ethanol as orange oil, MS: 386(MH$^+$).

Examples 36

36.1

A flask was charged with 31.1 mg (0.04 mmol, 0.05 eq) bis(triphenylphosphine) palladium(II) chloride, evacuated and backfilled with argon. 500 mg (0.89 mmol) 4-[3-(4-Bromo-phenyl)-benzo[d]isothiazol-6-yloxy]-butyl}-[2-(tert-butyl-dimethyl-silanyloxy)-
-ethyl-amine and 7.0 mg (0.03 mmol, 0.03 eq) triphenylphosphine in 5 ml piperidine were added, and the solution stirred for 20 min. 1.7 mg (0.01 mmol, 0.01 eq) CuI were added, followed by 113 µl (1.06 mmol, 1.2 eq) 1-Dimethylamino-2-propyne. The solution was stirred at 50° C. over night and at 70° C. for 1 h. The mixture was poured on water and EtOAc, the layers were separated and the inorganic layer was extracted with EtOAc. The combined organic phases were washed with brine and dried over Na$_2$SO$_4$. Column chromatography on silica gel with CH$_2$Cl$_2$:MeOH 95:5 yielded 350 mg (70%) (3-{4-[6-(4-{[2-(tert-Butyl-dimethyl-silanyloxy)-ethyl]-ethyl-amino}-butoxy)-benzo[d]isothiazol-3-yl]-phenyl}-prop-2-ynyl)-dimethyl-amine as brown oil.

350 mg (0.62 mmol) (3-{4-[6-(4-{[2-(tert-Butyl-dimethyl-silanyloxy)-ethyl]-ethyl-amino}-butoxy)-benzo[d]isothiazol-3-yl]-phenyl}-prop-2-ynyl)-dimethyl-amine in 5 ml THF were treated with 0.92 ml 1M Bu$_4$NF in THF at RT for 1 h. The solution was concentrated and the residue was purified by column chromatography on silica gel to give 185 mg (66%) 2-[(4-{3-[4-(3-Dimethylamino-prop-1-ynyl)-phenyl]-benzo[d]isothiazol-6-yloxy}-butyl)-ethyl-amino]-ethanol as light brown oil, MS: 452 (MH$^+$).

36.2

In analogy to example 36.1, {4-[3-(4-Bromo-phenyl)-benzo[d]isothiazol-6-yloxy]-butyl}-[2-(tert-butyl-dimethyl-silanyloxy)-ethyl]-ethyl-amine and 2-Propyn-1-ol were converted to yield 3-[4-(6-{4-[Ethyl-(2-hydroxy-ethyl)-amino]-butoxy}-benzo[d]isothiazol-3-yl)-phenyl]-prop-2-yn-1-ol as yellow oil, MS: 425 (MH$^+$).

36.3

In analogy to example 36.1, {4-[3-(4-Bromo-phenyl)-benzo[d]isothiazol-6-yloxy]-butyl}-[2-(tert-butyl-dimethyl-silanyloxy)-ethyl]-ethyl-amine and N-Methylpropargylamine were converted to yield 2-[Ethyl-(4-{3-[4-(3-methylamino-prop-1-ynyl)-phenyl]-benzo[d]isothiazol-6-yloxy}-butyl)-amino]-ethanol as brown oil, MS: 438 (MH$^+$).

Example 37

37.1

To 14.3 ml (146.3 mmol) 2-Ethylaminoethanol in 60 ml THF were added 362 mg (3.7 mmol) CuCl, followed by 7.5 g (73.1 mmol) 3-Chloro-3-methyl-1-butyne. The solution was stirred at RT for 2 h, the solvent was removed and the residue dissolved in ether/2M HCl. The phases were separated and after addition of Na$_2$CO$_3$ to the aqueous phase (pH 9), it was extracted with ether. The ether phase was dried over Na$_2$SO$_4$ and concentrated. Distillation by Kugelrohr yielded 2-[(1,1-Dimethyl-prop-2-ynyl)-ethyl-amino]-ethanol as colorless oil, MS: 155 (M).

37.2

In analogy to example 37.1, 3-Chloro-3-methyl-1-butyne and Allylmethylamine were converted to yield Allyl-(1,1-dimethyl-prop-2-ynyl)-methyl-amine as white solid, MS: 137(M).

37.3

In analogy to example 37.1, 3-Chloro-3-methyl-1-butyne and N-(2-Methoxyethyl) methylamine were converted to yield (1,1-Dimethyl-prop-2-ynyl)-(2-methoxy-ethyl)-methyl-amine as colorless oil, MS: 155 (M).

37.4

In analogy to example 37.1, 3-Chloro-3-methyl-1-butyne and N-(2-Methoxyethyl)methylamine were converted to yield (1,1-Dimethyl-prop-2-ynyl)-ethyl-(2-methoxy-ethyl)-amine as colorless oil, MS: 170 (MH$^+$).

37.5

According to Ishihara, Kazuaki; Kubota, Manabu; Kurihara, Hideki; Yamamoto, Hisashi. Scandium Trifluoromethanesulfonate as an Extremely Active Lewis Acid Catalyst in Acylation of Alcohols with Acid Anhydrides and Mixed Anhydrides. J. Org. Chem. (1996), 61(14), 4560–4567.

To 3.1 g (25 mmol) 1-ethynyl-1-cyclohexanol in 25 ml acetonitrile were added 7.1 ml (75 mmol, 3 eq) acetic anhydride at −20° C. 12.3 mg (0.03 mmol) scandiumtriflate in 300 µl THF were added and the solution was stirred for 2 h. Additional 12.3 mg (0.03 mmol) scandiumtriflate in 300 µl THF were added and stirring was continued for 30 min. A saturated aqueous solution of NaHCO$_3$ and ether were added. The layers were separated and the inorganic one was extracted with ether. The combined organic phases were washed with brine and dried over Na$_2$SO$_4$. Evaporation yielded 4.6 g crude 1-ethynylcyclohexyl acetate as colorless oil, MS: 166 (M).

37.6

Analogously to Imada, Yasushi; Yuasa, Mari; Nakamura, Ishin; Murahashi, Shun-Ichi. Copper(I)-Catalyzed Amination of Propargyl Esters. Selective Synthesis of Propargylamines, 1-Alken-3-ylamines, and (Z)-Allylamines. J. Org. Chem. (1994), 59(9), 2282–4.

To 1.17 ml (12 mmol) ethylaminoethanol in 8 ml THF were added 29.8 mg (0.3 mmol) CuCl, followed by 1 g (6.02 mmol) 1-ethynylcyclohexyl acetate. The solution was stirred at RT for 3 h, the solvent was removed and the residue dissolved in ether/2M HCl. The phases were separated, and after addition of NaOH (pH 11) to the aqueous phase, it was extracted with ether. The ether phase was dried over Na$_2$SO$_4$ and concentrated. Distillation by Kugelrohr yielded 2-[Ethyl-(1-ethynyl-cydohexyl)-amino]-ethanol as colorless oil, MS: 196 (MH$^+$).

37.7

In analogy to example 37.5 and 37.6, 3-Butyn-2-ol and 2-Ethylaminoethanol were converted to yield 2-[Ethyl-(1-methyl-prop-2-ynyl)-amino]-ethanol as colorless oil, MS: 141 (M).

37.8

In analogy to example 37.5 and 37.6, 3-Butyn-2-ol and N-(Methoxyethyl)methylamine were converted to yield (2-Methoxy-ethyl)-methyl-(1-methyl-prop-2-ynyl)-amine as colorless oil, MS: 141 (M).

37.9

In analogy to example 37.5 and 37.6,3-Butyn-2-ol and N-(Methoxyethyl)ethylamine were converted to yield Ethyl- (2-methoxy-ethyl)-(1-methyl-prop-2-ynyl)-amine as colorless oil, MS: 155 (M).

37.10

In analogy to example 37.5 and 37.6, 1-Ethinylcyclopentanol and N-Methyl-allylamine were converted to yield Allyl-(1-ethynyl-cyclopentyl)-methyl-amine as colorless oil, MS: 163 (M).

Example 38

38.1

In analogy to example 14.1, Trifluoro-methanesulfonic acid 3-(4-trifluoromethyl-phenyl)-benzo[d]isothiazol-6-yl ester and Allyl-(1,1-dimethyl-prop-2-ynyl)-methyl-amine were converted to yield Allyl-{1,1-dimethyl-3-[3-(4-trifluoromethyl-phenyl)-benzo[d]isothiazol-6-yl]-prop-2-ynyl}-methyl-amine as brown oil, MS: 415 (MH$^+$).

38.2

In analogy to example 14.1, Trifluoro-methanesulfonic acid 3-(4-trifluoromethyl-phenyl)-benzo[d]isothiazol-6-yl ester and 2-[(1,1-Dimethyl-prop-2-ynyl)-ethyl-amino]-ethanol were converted to yield 2-((1,1-Dimethyl-3-[3-(4-trifluoromethyl-phenyl)-benzo[d]isothiazol-6-yl]-prop-2-ynyl)-ethyl-amino)-ethanol as off-white foam, MS: 433 (MH$^+$).

38.3

In analogy to example 14.1, Trifluoro-methanesulfonic acid 3-(4-trifluoromethyl-phenyl)-benzo[d]isothiazol-6-yl ester and (1,1-Dimethyl-prop-2-ynyl)-(2-methoxy-ethyl)-methyl-amine were converted to yield {1,1-Dimethyl-3-[3-(4-trifluoromethyl-phenyl)-benzo[d]isothiazol-6-yl]-prop-2-ynyl-(2-methoxy-ethyl)-methyl-amine as brown oil, MS: 433 (MH$^+$).

38.4

In analogy to example 14.1, Trifluoro-methanesulfonic acid 3-(4-trifluoromethyl-phenyl)-benzo[d]isothiazol-6-yl ester and (1,1-Dimethyl-prop-2-ynyl)-ethyl-(2-methoxy-ethyl)-amine were converted to yield 11, 1-Dimethyl-3-[3-(4-trifluoromethyl-phenyl)-benzo[d]isothiazol-6-yl]-prop-2-ynyl}-ethyl-(2-methoxy-ethyl)-amine as brown oil, MS: 447 (MH$^+$).

38.5

In analogy to example 14.1, Trifluoro-methanesulfonic acid 3-(4-trifluoromethyl-phenyl)-benzo[d]isothiazol-6-yl ester and 2-[Ethyl-(1-ethynyl-cyclohexyl)-amino]-ethanol were converted to yield 2-(Ethyl-{1-[3-(4-trifluoromethyl-phenyl)-benzo[d]isothiazol-6-ylethynyl]-cydohexyl}-amino)-ethanol as brown oil, MS: 473.3 (MH$^+$).

38.6

In analogy to example 14.1, Trifluoro-methanesulfonic acid 3-(4-trifluoromethyl-phenyl)-benzo[d]isothiazol-6-yl ester and 2-[Ethyl-(1-methyl-prop-2-ynyl)-amino]-ethanol were converted to yield 2-(Ethyl-{1-methyl-3-[3-(4-trifluoromethyl-phenyl)-benzo[d]isothiazol-6-yl]-prop-2-ynyl}-amino)-ethanol as brown oil, MS: 419 (MH$^+$).

38.7

In analogy to example 14.1, Trifluoro-methanesulfonic acid 3-(4-trifluoromethyl-phenyl)-benzo[d]isothiazol-6-yl ester and (2-Methoxy-ethyl)-methyl-(1-methyl-prop-2-ynyl)-amine were converted to yield (2-Methoxy-ethyl)-methyl-{1-methyl-3-[3-(4-trifluoromethyl-phenyl)-benzo[d]isothiazol-6-yl]-prop-2-ynyl}-amine as brown oil, MS: 419 (MH$^+$).

38.8

In analogy to example 14.1, Trifluoro-methanesulfonic acid 3-(4-trifluoromethyl-phenyl)-benzo[d]isothiazol-6-yl ester and Ethyl-(2-methoxy-ethyl)-(1-methyl-prop-2-ynyl)-amine were converted to yield Ethyl-(2-methoxy-ethyl)-{1-methyl-3-[3-(4-trifluoromethyl-phenyl)-benzo[d]isothiazol-6-yl]-prop-2-ynyl}-amine as brown oil, MS: 433 (MH$^+$).

38.9

In analogy to example 14.1, Trifluoro-methanesulfonic acid 3-(4-trifluoromethyl-phenyl)-benzo[d]isothiazol-6-yl ester and Allyl-(1-ethynyl-cyclopentyl)-methyl-amine were converted to yield Allyl-methyl-{1-[3-(4-trifluoromethyl-phenyl)-benzo[d]isothiazol-6-ylethynyl]-cyclopentyl}-amine as light yellow oil, MS: 441 (MH$^+$).

Example 39

39.1

To 540 mg (11.37 mmol) 2-(Ethyl-{4-[3-(4-trifluoromethyl-phenyl)-benzo[d]isothiazol-6-yloxy]-butyl}-amino)-ethanol in 6 ml CH$_2$Cl$_2$ were added 0.22 ml (1.7 mmol) DAST at −78° C. After stirring at that temperature for 3.5 h, additional 0.2 ml (1.6 mmol) DAST were added and the mixture was slowly warmed to RT over night. The solution was added to a cooled aqueous solution of Na$_2$CO$_3$ and extracted with EtOAc.

The organic phase was washed with brine and dried over Na$_2$SO$_4$. Column chromatography CH$_2$Cl$_2$:MeOH 95:5 yielded 79.3 mg (16%) Ethyl-(2-fluoro-ethyl)-{4-[3-(4-trifluoromethyl-phenyl)-benzo[d]isothiazol-6-yloxy]-butyl}-amine as brown oil, MS: 441 (MH$^+$).

39.2

In analogy to example 39.1, 2-({4-[3-(4-Bromo-phenyl)-benzo[d]isothiazol-6-yloxy]-butyl}-ethyl-amino)-ethanol was converted to yield {4-[3-(4-Bromo-phenyl)-benzo[d]isothiazol-6-yloxy]-butyl}-ethyl-(2-fluoro-ethyl)-amine as light yellow oil, MS: 451 (MH$^+$, 1Br).

Example 40

40.1

200 mg (0.54 mmol) 4-[3-(4-Bromo-phenyl)-benzo[d]isothiazol-6-yl]-2-methyl-but-3-yn-2-ol in 2 ml THF were treated with 36 μl (5.6 mmol) 1.6 M N-Butyllithium in hexane at −78° C. for 30 min. 112 μl (0.81 mmol, 1.5 eq) Triethylamine in 0.5 ml THF and 117 μl (0.8 mmol, 1.5 eq) Diethylchlorophosphate in 0.5 ml THF were added and the solution was stirred at −78° C. over night and at 0° C. for 4 h. Water was added, and the inorganic phase was extracted with EtOAc, the combined organic phases were washed with brine and dried over Na$_2$SO$_4$. Column chromatography on silica gel with hexane:EtOAc 3:1 gave 90 mg (33%) Phosphoric acid 3-[3-(4-bromo-phenyl)-benzo[d]isothiazol-6-yl]-1,1-dimethyl-prop-2-ynyl ester diethyl ester as yellow semisolid, MS: 508 (MH$^+$, 1Br).

40.2

To 45 mg (0.09 mmol) Phosphoric acid 3-[3-(4-bromo-phenyl)-benzo[d]isothiazol-6-yl]-1,1-dimethyl-prop-2-ynyl ester diethyl ester and 16 μl (0.18 mmol) 2-Ethylaminoethanol in 0.5 ml THF 10.2 mg (0.01 mmol) tetrakis(triphenylphosphine)palladium was added and the suspension stirred at 50° C. over night. The mixture was added to a saturated aqueous solution of NaHCO$_3$ and EtOAc, the phases were separated and the inorganic one was extracted with EtOAc. The combined organic phases were washed with brine and dried over Na$_2$SO$_4$. Column chromatography on silica gel with CH$_2$Cl$_2$:MeOH 95:5 gave 2-((3-[3-(4-Bromo-phenyl)-benzo[d]isothiazol-6 yl]-1,1-dimethyl-prop-2-ynyl)-ethyl-amino)-ethanol as yellow semisolid, MS: 443 (MH$^+$, 1Br).

Example 41

41.1

Under argon a flask was charged with 1.3 g (2.9 mmol) 2-({4-[3-(4-Bromo-phenyl)-benzo[d]isothiazol-6-yloxy]-butyl}-ethyl-amino)-ethanol in 10 ml piperidine and 170 mg (0.14 mmol, 0.05 eq) Pd(PPh$_3$)$_4$ and 28 mg (0.14 mmol, 0.05 eq) CuI. After stirring for 10 min, 1 ml (4.44 mmol, 1.5 eq) (triisopropylsilyl)acetylene was added over a period of 1 h to this solution. The solution was stirred at 80° C. for 1.5 h. The solution was poured on ice water, acidified and the inorganic layer was extracted with EtOAc. The combined organic phases were washed with brine and dried over Na$_2$SO$_4$.

The crude product was dissolved in 20 ml THF and treated with 3.75 ml 1M Bu$_4$NF in THF at RT for 1 h. The solution was diluted with EtOAc and a solution of Na$_2$CO$_3$. The inorganic layer was extracted with EtOAc, the combined organic phases were washed with brine and dried over Na$_2$SO$_4$. Column chromatography on silica with CH$_2$Cl$_2$:MeOH 9:1 yielded 160 mg (19%) 2-(Ethyl-{4-[3-(4-ethynyl-phenyl)-benzo[d]isothiazol-6-yloxy]-butyl}-amino)-ethanol as brown oil, MS: 395 (MH$^+$).

41.2

150 mg (0.4 mmol) 2-(Ethyl-{4-[3-(4-ethynyl-phenyl)-benzo[d]isothiazol-6-yloxy]-butyl}-amino)-ethanol in 6 ml EtOAc were hydrogenated in the presence of 50 mg 10% Pd/C, filtration over decalite, followed by purification by preparative HPLC yielded 2-(Ethyl-{4-[3-(4-ethyl-phenyl)-benzo[d]isothiazol-6-yloxy]-butyl}-amino)-ethanol as light yellow oil, MS: 399 (MH$^+$).

Example 42

42.1

To a suspension of 0.74 g (16.9 mmol) NaH (55% in mineral oil) in 40 ml THF was added a solution of 4 g (13.1 mmol) 3-(4-Bromo-phenyl)-benzo[d]isothiazol-6-ol in 20 ml THF at RT. The solution was stirred at RT for 1 h, 2.1 ml (14.3 mmol) tbutyl bromoacetate was added. The solution was stirred at RT over night, 1M KHSO$_4$ was added carefully and the layers separated. The inorganic one was extracted with EtOAc, the combined organic phases were washed with water and brine and dried over Na$_2$SO$_4$. Column chromatography on silica gel with EtOAc: hexane 1:4 yielded 4.95 g (90%) [3-(4-Bromo-phenyl)-benzo[d]isothiazol-6-yloxy]-acetic acid tert-butyl ester as colorless oil, MS: 420 (MH$^+$, 1Br).

42.2

3.89 g (9.3 mmol) [3-(4-Bromo-phenyl)-benzo[d]isothiazol-6-yloxy]-acetic acid tert-butyl ester in 35 ml CH$_2$Cl$_2$ were added 17 ml TFA at 0° C. The solution was stirred at RT for 2 h, concentrated and titurated with ether to yield 3 g (89%) [3-(4-Bromo-phenyl)-benzo[d]isothiazol-6-yloxy]-acetic acid as white solid, MS: 362(M–H, 1Br).

42.3

To 400 mg (1.1 mmol) trans-5-[4-(tert-Butoxycarbonyl-methyl-amino)-cyclohexyl]-pentanoic acid in 10 ml CH$_2$Cl$_2$ were added 0.82 ml (1.6 mmol, 1.5 eq) 1M dimethylamine in THF and 0.18 ml (1.6 mmol, 1.5 eq) NMM. The solution was cooled to 0° C. and 274 mg (1.43 mmol, 1.3 eq) EDCI and 30 mg (0.2 mmol) HOBT were added. The mixture was stirred at RT over night, partitioned between CH$_2$Cl$_2$ and a saturated aqueous solution of NaHCO$_3$. The organic phase was washed with KHSO$_4$ and brine, dried over Na$_2$SO$_4$ and evaporated. Column chromatography with EtOAc/hexane 2:1 gave 370 mg (86%) 2-[3-(4-Bromo-phenyl)-benzo[d]isothiazol-6-yloxy]-N,N-dimethyl-acetamide as white solid, mp 168° C., MS: 391 (MH$^+$, 1Br).

42.4

Analogously to example 42.3, from [3-(4-Bromo-phenyl)-benzo[d]isothiazol-6-yloxy]-acetic acid and N,O-Dimethylhydroxylamine hydrochloride was prepared 2-[3-(4-Bromo-phenyl)-benzo[d]isothiazol-6-yloxy]-N-methoxy-N-methyl-acetamide as white solid, mp 159° C., MS: 407 (MH$^+$, 1Br).

42.5

To a solution of 160 mg (0.41 mmol) 2-[3-(4-Bromo-phenyl)-benzo[d]isothiazol-6-yloxy]-N,N-dimethyl-acetamide in 4 ml THF was added 95 mg (4.1 mmol, 1 eq) zirconium(IV) chloride at –10° C. and the reaction mixture was stirred for additional 30 min. 0.82 ml 3M (24.5 mmol, 6 eq) methylmagnesium bromide in THF were added at –10° C. and the mixture was warmed to RT. After stirring for 1 h, the mixture was added to a mixture of 30% NaOH and CH$_2$Cl$_2$. The inorganic phase was extracted with CH$_2$Cl$_2$ and the combined organic phases were washed with brine and dried over Na$_2$SO$_4$ and evaporated. The residue was purified by column chromatography on silica gel with CH$_2$Cl$_2$ to CH$_2$Cl$_2$:MeOH 9:1 to yield 63 mg (38%) {2-[3-(4-Bromo-phenyl)-benzo[d]isothiazol-6-yloxy]-1,1-dimethyl-ethyl}-dimethyl-amine as colorless oil, MS: 405 (MH$^+$, 1Br).

42.6

To 208 mg (0.51 mmol) 2-[3-(4-Bromo-phenyl)-benzo[d]isothiazol-6-yloxy]-N-methoxy-N-methyl-acetamide in 8 ml THF were added 0.51 ml 3M (1.53 mmol, 3 eq) methylmagnesiumbromide in THF at –75° C. The solution was slowly warmed to RT over night, a saturated aqueous solution of NH$_4$Cl was added and the mixture stirred for 30 min. The phases were separated and the inorganic phase was extracted with EtOAc. The combined organic phases were dried over Na$_2$SO$_4$ and evaporated. Column chromatography on silica gel with EtOAc:hexane 1:4 yielded 109 mg (53%) 1-[3-(4-Bromo-phenyl)-benzo[d]isothiazol-6-yloxy]-propan-2-one as white solid, MS: 361 (M, 1Br).

42.7

74 mg (0.20 mmol) 1-[3-(4-Bromo-phenyl)-benzo[d]isothiazol-6-yloxy]-propan-2-one were treated with 133 µM 2M(0.17 mmol) dimethylamine in THF and 60 µM (0.20 mmol) tetraisopropyl orthotitanate. The solution was stirred at RT for 3.5 h. The mixture was diluted with 2 ml ethanol and 15 mg (0.2 mmol) NaCNBH$_3$ were added, and stirring was continued over night. NaHCO$_3$ and EtOAc were added, the inorganic phase extracted with EtOAc. The organic phases were washed with water and brine, dried over Na$_2$SO$_4$ and evaporated. Column chromatography with CH$_2$Cl$_2$:MeOH 9:1 gave {2-[3-(4-Bromo-phenyl)-benzo[d]isothiazol-6-yloxy]-1-methyl-ethyl}-dimethyl-amine as colorless oil, MS: 391 (MH$^+$, 1Br).

Example 43

43.1

In analogy to example 12.1, 2-Methyl-3-(4-trifluoromethyl-phenyl)-benzo[b]thiophen-6-ol (example 26.5) was treated with trifluoromethane sulfonic anhydride in pyridine to yield the Trifluoro-methanesulfonic acid 2-methyl-3-(4-trifluoromethyl-phenyl)-benzo[b]thiophen-6-yl ester as light brown oil, MS: 440 ($M^+$).

43.2

In analogy to example 12.1, 3-(4-Fluoro-phenyl)-benzo[b]thiophen-6-ol and trifluoromethane sulfonic anhydride were converted to yield Trifluoro-methanesulfonic acid 3-(4-fluoro-phenyl)-benzo[b]thiophene-6-yl ester as brown oil, MS: 376 (M).

Example 44

44.1

In analogy to example 13.1, the Trifluoro-methanesulfonic acid 2-methyl-3-(4-trifluoromethyl-phenyl)-benzo[b]thiophen-6-yl ester was reacted with 2-propyn-1-ol to yield the 3-[2-Methyl-3-(4-trifluoromethyl-phenyl)-benzo[b]thiophen-6-yl]-prop-2-yn-1-ol as yellow oil, MS: 346 ($M^+$).

44.2

In analogy to example 13.1, the Trifluoro-methanesulfonic acid 2-methyl-3-(4-trifluoromethyl-phenyl)-benzo[b]thiophen-6-yl ester was reacted with 3-butyn-1-ol to yield the 4-[2-Methyl-3-(4-trifluoromethyl-phenyl)-benzo[b]thiophen-6-yl]-but-3-yn-1-ol as brown oil, MS: 360 ($M^+$).

44.3

In analogy to example 13.1, the Trifluoro-methanesulfonic acid 2-methyl-3-(4-trifluoromethyl-phenyl)-benzo[b]thiophen-6-yl ester was reacted with 4-pentyn-1-ol to yield the 5-[2-Methyl-3-(4-trifluoromethyl-phenyl)-benzo[b]thiophen-6-yl]-pent-4-yn-1-ol as brown oil, MS: 374 ($M^+$).

44.4

In analogy to example 14.1, Trifluoro-methanesulfonic acid 3-(4-fluoro-phenyl)-benzo[b]thiophene-6-yl ester and 4-pentyn-1-ol were converted to yield 5-[3-(4-Fluoro-phenyl)-benzo[b]thiophen-6-yl]-pent-4-yn-1-ol as light green solid, MS: 310 (M).

Example 45

45.1

In analogy to example 20.1, the 3-[2-Methyl-3-(4-trifluoromethyl-phenyl)-benzo[b]thiophen-6-yl]-prop-2-yn-1-ol was hydrogenated to yield the 3-[2-Methyl-3-(4-trifluoromethyl-phenyl)-benzo[b]thiophen-6-yl]-propan-1-ol as colorless oil, MS: 350 ($M^+$).

45.2

In analogy to example 20.1, the 4-[2-Methyl-3-(4-trifluoromethyl-phenyl)-benzo[b]thiophen-6-yl]-but-3-yn-1-ol was hydrogenated to yield the 4-[2-Methyl-3-(4-trifluoromethyl-phenyl)-benzo[b]thiophen-6-yl]-butan-1-ol as yellowish oil, MS: 364 ($M^+$).

Example 46

46.1

In analogy to example 21.1, the 3-[2-Methyl-3-(4-trifluoromethyl-phenyl)-benzo[b]thiophen-6-yl]-propan-1-ol was treated with methanesulfonic acid chloride to yield the Methanesulfonic acid 3-[2-methyl-3-(4-trifluoromethyl-phenyl)-benzo[b]thiophen-6-yl]-propyl ester as yellow oil, MS: 428 ($M^+$).

46.2

In analogy to example 21.1, the 4-[2-Methyl-3-(4-trifluoromethyl-phenyl)-benzo[b]thiophen-6-yl]-butan-1-ol was treated with methanesulfonic acid chloride to yield the Methanesulfonic acid 4-[2-methyl-3-(4-trifluoromethyl-phenyl)-benzo[b]thiophen-6-yl]-butyl ester as yellowish oil, MS: 442 ($M^+$).

46.3

In analogy to example 21.1, the 5-[2-Methyl-3-(4-trifluoromethyl-phenyl)-benzo[b]thiophen-6-yl]-pent-4-yn-1-ol was treated with methanesulfonic acid chloride to yield the Methanesulfonic acid 5-[2-methyl-3-(4-trifluoromethyl-phenyl)-benzo[b]thiophen-6-yl]-pent-4-ynyl ester as yellow oil, MS: 452 ($M^+$).

46.4

In analogy to example 21.1, the 3-[2-Methyl-3-(4-trifluoromethyl-phenyl)-benzo[b]thiophen-6-yl]-prop-2-yn-1-ol was treated with methanesulfonic acid chloride to yield a mixture of the Methanesulfonic acid 3-[2-methyl-3-(4-trifluoromethyl-phenyl)-benzo[b]thiophen-6-yl]-prop-2-ynyl ester and the 6-(3-Chloro-prop-1-ynyl)-2-methyl-3-(4-trifluoromethyl-phenyl)-benzo[b]thiophene as yellow oil, used without further charcterization.

Example 47

47.1

In analogy to example 32.1, the Methanesulfonic acid 3-[2-methyl-3-(4-trifluoromethyl-phenyl)-benzo[b]thiophen-6-yl]-propyl ester was converted to yield the Methanesulfonic acid 3-[2-methyl-1,1-dioxo-3-(4-trifluoromethyl-phenyl)-1H-11 6-benzo[b]thiophen-6-yl]-propyl ester as yellow oil, MS: 478 ($MH^+$).

47.2

In analogy to example 32.1, the Methanesulfonic acid 4-[2-methyl-3-(4-trifluoromethyl-phenyl)-benzo[b]thiophen-6-yl]-butyl ester was converted to yield the Methanesulfonic acid 4-[2-methyl-1,1-dioxo-3-(4-trifluoromethyl-phenyl)-1H -11 6-benzo[b]thiophen-6-yl]-butyl ester as yellowish oil, MS: 474 ($M^+$).

47.3

In analogy to example 32.1, the Methanesulfonic acid 5-[2-methyl-3-(4-trifluoromethyl-phenyl)-benzo[b]thiophen-6-yl]-pent-4-ynyl ester was converted to yield the Methanesulfonic acid 5-[2-methyl-1,1-dioxo-3-(4-trifluoromethyl-phenyl)-1H-11 6-benzo[b]thiophen-6-yl]-pent-4-ynyl ester as colorless foam, MS: 484 ($M^+$).

Example 48

In analogy to the method described in example 33, Methanesulfonic acid esters or Chlorides were treated with secondary or primary amines in N,N-dimethylacetamide between room temperature and 60° C. to yield tertiary or secondary amine products as listed in the following table. The compounds were obtained as colorless, yellowish or brown oils.

| Example | Compound | MS MH+ | Methanesulfonate/ Chloride | Amine |
|---|---|---|---|---|
| 48.1 | Methyl-{3[2-methyl-3-(4-trifluoromethyl-phenyl)-benzo[b]thiophen-6-yl]-prop-2-ynyl}-propyl-amine | 402 | mixture of the Methanesulfonic acid 3-[2-methyl-3-(4-trifluoromethyl-phenyl)-benzo[b]thiophen-6-yl]-prop-2-ynyl ester and the 6-(3-Chloro-prop-1-ynyl)-2-methyl-3-(4-trifluoromethyl-phenyl)-benzo[b]thiophene | N-methyl-propylamine |
| 48.2 | 2-(Ethyl-{3-[2-methyl-3-(4-trifluoromethyl-phenyl)-benzo[b]thiophen-6-yl]-prop-2-ynyl}-amino)-ethanol | 418 | mixture of the Methanesulfonic acid 3-[2-methyl-3-(4-trifluoromethyl-phenyl)-benzo[b]thiophen-6-yl]-prop-2-ynyl ester and the 6-(3-Chloro-prop-1-ynyl)-2-methyl-3-(4-trifluoromethyl-phenyl)-benzo[b]thiophene | 2-ethylamino-ethanol |
| 48.3 | Diethyl-{3-[2-methyl-3-(4-trifluoromethyl-phenyl)-benzo[b]thiophen-6-yl]-prop-2-ynyl}-amine | 402 | mixture of the Methanesulfonic acid 3-[2-methyl-3-(4-trifluoromethyl-phenyl)-benzo[b]thiophen-6-yl]-prop-2-ynyl ester and the 6-(3-Chloro-prop-1-ynyl)-2-methyl-3-(4-trifluoromethyl-phenyl)-benzo[b]thiophene | diethyl-amine |
| 48.4 | Allyl-methyl-{3-[2-methyl-3-(4-trifluoromethyl-phenyl)-benzo[b]thiophen-6-yl]-prop-2-ynyl}-amine | 400 | mixture of the Methanesulfonic acid 3-[2-methyl-3-(4-trifluoromethyl-phenyl)-benzo[b]thiophen-6-yl]-prop-2-ynyl ester and the 6-(3-Chloro-prop-1-ynyl)-2-methyl-3-(4-trifluoromethyl-phenyl)-benzo[b]thiophene | N-allyl-methyl-amine |
| 48.5 | Allyl-methyl-{5-[2-methyl-3-(4-trifluoromethyl-phenyl)-benzo[b]thiophen-6-yl]-pent-4-ynyl}-amine | 428 | Methanesulfonic acid 5-[2-methyl-3-(4-trifluoromethyl-phenyl)-benzo[b]thiophen-6-yl]-pent-4-ynyl ester | N-allyl-methyl-amine |
| 48.6 | Methyl-{5-[2-methyl-3-(4-trifluoromethyl-phenyl)-benzo[b]thiophen-6-yl]-pent-4-ynyl}-propyl-amine | 430 | Methanesulfonic acid 5-[2-methyl-3-(4-trifluoromethyl-phenyl)-benzo[b]thiophen-6-yl]-pent-4-ynyl ester | N-methyl-propyl-amine |
| 48.7 | 2-(Ethyl-{5-[2-methyl-3-(4-trifluoromethyl-phenyl)-benzo[b]thiophen-6-yl]-pent-4-ynyl}-amino)-ethanol | 446 | Methanesulfonic acid 5-[2-methyl-3-(4-trifluoromethyl-phenyl)-benzo[b]thiophen-6-yl]-pent-4-ynyl ester | 2-ethylamino-ethanol |
| 48.8 | Diethyl-{5-[2-methyl-3-(4-trifluoromethyl-phenyl)-benzo[b]thiophen-6-yl]-pent-4-ynyl}-amine | 430 | Methanesulfonic acid 5-[2-methyl-3-(4-trifluoromethyl-phenyl)-benzo[b]thiophen-6-yl]-pent-4-ynyl ester | diethyl-amine |
| 48.9 | 1-{3-[2-Methyl-3-(4-trifluoromethyl-phenyl)-benzo[b]thiophen-6-yl]-propyl}-azetidine | 390 | Methanesulfonic acid 3-[2-methyl-3-(4-trifluoromethyl-phenyl)-benzo[b]thiophen-6-yl]-propyl ester | azetidine |
| 48.10 | 1-{3-[2-Methyl-3-(4-trifluoromethyl-phenyl)-benzo[b]thiophen-6-yl]-propyl}-piperidin-4-ol | 434 | Methanesulfonic acid 3-[2-methyl-3-(4-trifluoromethyl-phenyl)-benzo[b]thiophen-6-yl]-propyl ester | 4-hydroxy-piperidine |
| 48.11 | 1-{3-[2-Methyl-3-(4-trifluoromethyl-phenyl)-benzo[b]thiophen-6-yl]-propyl}-piperidine | 418 | Methanesulfonic acid 3-[2-methyl-3-(4-trifluoromethyl-phenyl)-benzo[b]thiophen-6-yl]-propyl ester | piperidine |
| 48.12 | 1-{3-[2-Methyl-3-(4-trifluoromethyl-phenyl)-benzo[b]thiophen-6-yl]-propyl}-pyrrolidine | 404 | Methanesulfonic acid 3-[2-methyl-3-(4-trifluoromethyl-phenyl)-benzo[b]thiophen-6-yl]-propyl ester | pyrrolidine |
| 48.13 | 2-(Ethyl-{3-[2-methyl-3-(4-trifluoromethyl-phenyl)-benzo[b]thiophen-6-yl]-propyll-amino)-ethanol | 422 | Methanesulfonic acid 3-[2-methyl-3-(4-trifluoromethyl-phenyl)-benzo[b]thiophen-6-yl]-propyl ester | 2-ethylamino-ethanol |

-continued

| Example | Compound | MS MH+ | Methanesulfonate/ Chloride | Amine |
|---|---|---|---|---|
| 48.14 | Allyl-methyl-{3-[2-methyl-3-(4-trifluoromethyl-phenyl)-benzo[b]thiophen-6-yl]-propyl}-amine | 404 | Methanesulfonic acid 3-[2-methyl-3-(4-trifluoromethyl-phenyl)-benzo[b]thiophen-6-yl]-propyl ester | N-allyl-methylamine |
| 48.15 | Allyl-methyl-{4-[2-methyl-3-(4-trifluoromethyl-phenyl)-benzo[b]thiophen-6-yl]-butyl}-amine | 418 | Methanesulfonic acid 4-[2-methyl-3-(4-trifluoromethyl-phenyl)-benzo[b]thiophen-6-yl]-butyl ester | N-allyl-methylamine |
| 48.16 | 2-(Ethyl-{4-[2-methyl-3-(4-trifluoromethyl-phenyl)-benzo[b]thiophen-6-yl]-butyl}-amino)-ethanol | 436 | Methanesulfonic acid 4-[2-methyl-3-(4-trifluoromethyl-phenyl)-benzo[b]thiophen-6-yl]-butyl ester | 2-ethylamino-ethanol |
| 48.17 | 2-{4-[2-Methyl-3-(4-trifluoromethyl-phenyl)-benzo[b]thiophen-6-yl]-butylamino}-ethanol | 408 | Methanesulfonic acid 4-[2-methyl-3-(4-trifluoromethyl-phenyl)-benzo[b]thiophen-6-yl]-butyl ester | ethanolamine |
| 48.18 | 1-{4-[2-Methyl-3-(4-trifluoromethyl-phenyl)-benzo[b]thiophen-6-yl]-butyl}-piperidine | 432 | Methanesulfonic acid 4-[2-methyl-3-(4-trifluoromethyl-phenyl)-benzo[b]thiophen-6-yl]-butyl ester | piperidine |
| 48.19 | 1-{4-[2-Methyl-3-(4-trifluoromethyl-phenyl)-benzo[b]thiophen-6-yl]-butyl}-piperidin-4-ol | 448 | Methanesulfonic acid 4-[2-methyl-3-(4-trifluoromethyl-phenyl)-benzo[b]thiophen-6-yl]-butyl ester | 4-hydroxy-piperidine |
| 48.20 | {4-[2-Methyl-3-(4-trifluoromethyl-phenyl)-benzo[b]thiophen-6-yl]-butyl}-propyl-amine | 406 | Methanesulfonic acid 4-[2-methyl-3-(4-trifluoromethyl-phenyl)-benzo[b]thiophen-6-yl]-butyl ester | propylamine |
| 48.21 | 2-(Ethyl-{3-[2-methyl-1,1-dioxo-3-(4-trifluoromethyl-phenyl)-1H-1l6-benzo[b]thiophen-6-yl]-propyl}-amino)-ethanol | 454 | Methanesulfonic acid 3-[2-methyl-1,1-dioxo-3-(4-trifluoromethyl-phenyl)-1H-1l6-benzo[b]thiophen-6-yl]-propyl ester | 2-ethylamino-ethanol |
| 48.22 | 2-{3-[2-Methyl-1,1-dioxo-3-(4-trifluoro-methyl-phenyl)-1H-1l6-benzo[b]thiophen-6-yl]-propylamino}-ethanol | 426 | Methanesulfonic acid 3-[2-methyl-1,1-dioxo-3-(4-trifluoromethyl-phenyl)-1H-1l6-benzol[b]thiophen-6-yl]-propyl ester | ethanolamine |
| 48.23 | {3-[2-Methyl-1,1-dioxo-3-(4-trifluoromethyl-phenyl)-1H-1l6-benzo[b]thiophen-6-yl]-propyl}-propyl-amine | 424 | Methanesulfonic acid 3-[2-methyl-1,1-dioxo-3-(4-trifluoromethyl-phenyl)-1H-1l6-benzo[b]thiophen-6-yl]-propyl ester | N-propyl-amine |
| 48.24 | 1-{3-[2-Methyl-1,1-dioxo-3-(4-trifluoro-methyl-phenyl)-1H-1l6-benzo[b]thiophen-6-yl]-propyl}-piperidin-4-ol | 466 | Methanesulfonic acid 3-[2-methyl-1,1-dioxo-3-(4-trifluoromethyl-phenyl)-1H-1l6-benzo[b]thiophen-6-yl]-propyl ester | 4-hydroxy-piperidine |
| 48.25 | 1-{3-[2-Methyl-1,1-dioxo-3-(4-trifluoro-methyl-phenyl)-1H-1l6-benzo[b]thiophen-6-yl]-propyl}-piperidine | 450 | Methanesulfonic acid 3-[2-methyl-1,1-dioxo-3-(4-trifluoromethyl-phenyl)-1H-1l6-benzo[b]thiophen-6-yl]-propyl ester | piperidine |
| 48.26 | Allyl-methyl-{3-[2-methyl-1,1-dioxo-3-(4-trifluoromethyl-phenyl)-1H-1l6-benzo[b]thiophen-6-yl]-propyl}-amine | 436 | Methanesulfonic acid 3-[2-methyl-1,1-dioxo-3-(4-trifluoromethyl-phenyl)-1H-1l6-benzo[b]thiophen-6-yl]-propyl ester | N-allyl-methylamine |
| 48.27 | 2-(Ethyl-{4-[2-methyl-1,1-dioxo-3-(4-trifluoro-methyl-phenyl)-1H-1l6-benzo[b]thiophen-6-yl]-butyl}-amino)-ethanol | 468 | Methanesulfonic acid 4-[2-methyl-1,1-dioxo-3-(4-trifluoromethyl-phenyl)-1H-1l6-benzo[b]thiophen-6-yl]-butyl ester | 2-ethylamino-ethanol |
| 48.28 | Allyl-methyl-{4-[2-methyl-1,1-dioxo-3-(4-trifluoromethyl-phenyl)-1H-1l6-benzo[b]thiophen-6-yl]-butyl}-amine | 450 | Methanesulfonic acid 4-[2-methyl-1,1-dioxo-3-(4-trifluoromethyl-phenyl)-1H-1l6-benzo[b]thiophen-6-yl]-butyl ester | N-allyl-methylamine |
| 48.29 | 1-{4-[2-Methyl-1,1-dioxo-3-(4-trifluoro-methyl-phenyl)-1H-1l6- | 464 | Methanesulfonic acid 4-[2-methyl-1,1-dioxo-3-(4-trifluoromethyl-phenyl)-1H-1l | piperidine |

| Example | Compound | MS MH+ | Methanesulfonate/ Chloride | Amine |
|---|---|---|---|---|
| | benzo[b]thiophen-6-yl]-butyl}-piperidine | | 6-benzo[b]thiophen-6-yl]-butyl ester | |
| 48.30 | 1-{4-[2-Methyl-1,1-dioxo-3-(4-trifluoro-methyl-phenyl)-1H-1λ6-benzo[b]thiophen-6-yl]-butyl}-piperidin-4-ol | 480 | Methanesulfonic acid 4-[2-methyl-1,1-dioxo-3-(4-trifluoromethyl-phenyl)-1H-1λ6-benzo[b]thiophen-6-yl]-butyl ester | 4-hydroxy-piperidine |
| 48.31 | {4-[2-Methyl-1,1-dioxo-3-(4-trifluoromethyl-phenyl)-1H-1λ6-benzo[b]thiophen-6-yl]-butyl}-propyl-amine | 438 | Methanesulfonic acid 4-[2-methyl-1,1-dioxo-3-(4-trifluoromethyl-phenyl)-1H-1λ6-benzo[b]thiophen-6-yl]-butyl ester | N-propyl-amine |
| 48.32 | 2-{4-[2-Methyl-1,1-dioxo-3-(4-trifluoro-methyl-phenyl)-1H-1λ6-benzo[b]thiophen-6-yl]-butylaminol-ethanol | 440 | Methanesulfonic acid 4-[2-methyl-1,1-dioxo-3-(4-trifluoromethyl-phenyl)-1H-1λ6-benzo[b]thiophen-6-yl]-butyl ester | ethanolamine |
| 48.33 | 2-(Ethyl-{5-[2-methyl-1,1-dioxo-3-(4-trifluoro-methyl-phenyl)-1H-1λ6-benzo[b]thiophen-6-yl]-pent-4-ynyl}-amino)-ethanol | 478 | Methanesulfonic acid 5-[2-methyl-1,1-dioxo-3-(4-trifluoromethyl-phenyl)-1H-1λ6-benzo[b]thiophen-6-yl]-pent-4-ynyl ester | 2-ethylamino-ethanol |
| 48.34 | Methyl-{5-[2-methyl-1,1-dioxo-3-(4-trifluoro-methyl-phenyl)-1H-1λ6-benzo[b]thiophen-6-yl]-pent-4-ynyl}-propyl-amine | 462 | Methanesulfonic acid 5-[2-methyl-1,1-dioxo-3-(4-trifluoromethyl-phenyl)-1H-1λ6-benzo[b]thiophen-6-yl]-pent-4-ynyl ester | N-methyl-propylamine |
| 48.35 | Allyl-methyl-{5-[2-methyl-1,1-dioxo-3-(4-trifluoromethyl-phenyl)-1H-1λ6-benzo[b]thiophen-6-yl]-pent-4-ynyl}-amine | 460 | Methanesulfonic acid 5-[2-methyl-1,1-dioxo-3-(4-trifluoromethyl-phenyl)-1H-1λ6-benzo[b]thiophen-6-yl]-pent-4-ynyl ester | N-allyl-methylamine |
| 48.36 | Diethyl-{5-[2-methyl-1,1-dioxo-3-(4-trifluoro-methyl-phenyl)-1H-1λ6-benzo[b]thiophen-6-yl]-pent-4-ynyl}-amine | 462 | Methanesulfonic acid 5-[2-methyl-1,1-dioxo-3-(4-trifluoromethyl-phenyl)-1H-1λ6-benzo[b]thiophen-6-yl]-pent-4-ynyl ester | diethyl-amine |

Example 49

49.1

In analogy to example 19.1, 5-[3-(4-Fluoro-phenyl)-benzo[b]thiophen-6-yl]-pent-4-yn-1-ol and 2-(Methylamino)ethanol were converted to yield 2-({5-[3-(4-Fluoro-phenyl)-benzo[b]thiophen-6-yl]-pent-4-ynyl}-methyl-amino)-ethanol as light brown oil, MS: 368 (MH+).

49.2

In analogy to example 19.1, 5-[3-(4-Fluoro-phenyl)-benzo[b]thiophen-6-yl]-pent-4-yn-1-ol and 2-(Ethylamino)ethanol were converted to yield 2-(Ethyl-{5-[3-(4-fluoro-phenyl)-benzo[b]thiophen-6-yl]-pent-4-ynyl}-amino)-ethanol as light brown oil, MS: 382 (MH+).

49.3

RO0721678-000: In analogy to example 19.1, 5-[3-(4-Fluoro-phenyl)-benzo[b]thiophen-6-yl]-pent-4-yn-1-ol and Dimethylamine were converted to yield {5-[3-(4-Fluoro-phenyl)-benzo[b]thiophen-6-yl]-pent-4-ynyl}-dimethyl-amine as light brown semisolid, MS: 338 (MH+).

49.4

In analogy to example 19.1, 5-[3-(4-Fluoro-phenyl)-benzo[b]thiophen-6-yl]-pent-4-yn-1-ol and N-Allylmethylamine were converted to yield Allyl-{5-[3-(4-fluoro-phenyl)-benzo[b]thiophen-6-yl]-pent-4-ynyl}-methyl-amine as brown oil, MS: 364 (MH+).

49.5

In analogy to example 19.1, 5-[3-(4-Fluoro-phenyl)-benzo[b]thiophen-6-yl]-pent-4-yn-1-ol and N-(Methoxyethyl)ethylamine were converted to yield Ethyl-{5-[3-(4-fluoro-phenyl)-benzo[b]thiophen-6-yl]-pent-4-ynyl}-(2-methoxy-ethyl)-amine as light brown oil, MS: 396 (MH+).

49.6

In analogy to example 19.1, 5-[3-(4-Fluoro-phenyl)-benzo[b]thiophen-6-yl]-pent-4-yn-1-ol and N-(Methoxyethyl)methylamine $CH_2Cl_2$. were converted to yield {5-[3-(4-Fluoro-phenyl)-benzo[b]thiophen-6-yl]-pent-4-ynyl}-(2-methoxy-ethyl)-methyl-amine as brown oil, MS: 382 (MH+).

49.7

In analogy to example 19.1, 4-[3-(4-Bromo-phenyl)-benzo[d]isothiazol-6-yl]-butan-1-ol and N-Methylallylamine were converted to yield Allyl-{4-[3-(4-bromo-phenyl)-benzo[d]isothiazol-6-yl]-butyl}-methyl-amine as colorless oil, MS: 415 (MH+, 1Br).

49.8

In analogy to example 19.1, 4-[3-(4-Bromo-phenyl)-benzo[d]isothiazol-6-yl]-butan-1-ol and Dimethylamine were converted to yield {4-[3-(4-Bromo-phenyl)-benzo[d]isothiazol-6-yl]-butyl}-dimethyl-amine as brown oil, MS: 389 (MH+, 1Br).

49.9

In analogy to example 19.1, 4-[3-(4-Bromo-phenyl)-benzo[d]isothiazol-6-yl]-butan-1-ol and 2-(Methylamino) ethanol were converted to yield 2-({4-[3-(4-Bromo-phenyl)-benzo[d]isothiazol-6-yl]-butyl}-methyl-amino)-ethanol as brown oil, MS: 419 (MH$^+$, 1Br).

49.10

In analogy to example 19.1, 4-[3-(4-Bromo-phenyl)-benzo[d]isothiazol-6-yl]-butan-1-ol and 2-(Ethylamino) ethanol were converted to yield 2-({4-[3-(4-Bromo-phenyl)-benzo[d]isothiazol-6-yl]-butyl}-ethyl-amino)-ethanol as yellow oil, MS: 433 (MH$^+$, 1Br).

49.11

In analogy to example 19.1, 4-[3-(4-Bromo-phenyl)-benzo[d]isothiazol-6-yl]-butan-1-ol and N-(Methoxyethyl) ethylamine were converted to yield {4-[3-(4-Bromo-phenyl)-benzo[d]isothiazol-6-yl]-butyl}-ethyl-(2-methoxy-ethyl)-amine as yellow oil, MS: 447 (MH$^+$, 1Br).

49.12

In analogy to example 19.1, 4-[3-(4-Bromo-phenyl)-benzo[d]isothiazol-6-yl]-butan-1-ol and N-(Methoxyethyl) methylamine were converted to yield {4-[3-(4-Bromo-phenyl)-benzo[d]isothiazol-6-yl]-butyl}-(2-methoxy-ethyl)-methyl-amine as yellow oil, MS: 433 (MH$^+$, 1Br).

Example 50

50.1

4.0 g (13.0 mmol) 2-Methyl-3-(4-trifluoromethyl-phenyl)-benzo[b]thiophen-6-ol (example 26.5) dissolved in 30 ml N,N-dimethylformamide were treated with 2.69 g (19.5 mmol, 1.5 eq) K$_2$CO$_3$ and 3.06 ml (19.5 mmol, 1.5 eq) 2-(2-Bromo-ethoxy)-tetrahydro-pyran. The reaction mixture was stirred at 120° C. for 3 hours, cooled to room temperature, poured into 100 ml of ice-water and extracted 3 times with 50 ml of ether. The combined ether phases were washed with brine, dried over magnesium sulfate and evaporated under reduced pressure. The residue formed was filtered over silica gel with dichloromethane as the eluent giving 5.76 g crude 2-{2-[2-Methyl-3-(4-trifluoromethyl-phenyl)-benzo[b]thiophen-6-yloxy]-ethoxy}-tetrahydro-pyran. This crude product was subsequently dissolved in 70 ml of 2N HCl in methanol and the reaction mixture stirred for 1 hour at room temperature. Subsequently, it was poored into a diluted sodium hydroxide/ice solution and extracted 3 times with 150 ml of dichloromethane. The combined dichloromethane phases were washed with brine, dried over magnesium sulfate and evaporated under reduced pressure. The residue formed was chromatographed on silica gel with dichloromethane as the eluent giving 4.3 g (93%) 2-[2-Methyl-3-(4-trifluoromethyl-phenyl)-benzo[b]thiophen-6-yloxy]-ethanol as colorless solid, MS: 352 (M+).

50.2

In analogy to example 21.1, 2-[2-Methyl-3-(4-trifluoromethyl-phenyl)-benzo[b]thiophen-6-yloxy]-ethanol and methanesulfonic acid chloride were converted to yield Methanesulfonic acid 2-[2-methyl-3-(4-trifluoromethyl-phenyl)-benzo[b]thiophen-6-yloxy]-ethyl ester as colorless solid, MS: 430 (MH$^+$).

50.3

0.300 g (0.697 mmol) Methanesulfonic acid 2-[2-methyl-3-(4-trifluoromethyl-phenyl)-benzo[b]thiophen-6-yloxy]-ethyl ester dissolved in 2.0 ml of N,N-dimethylformamide were treated with 0.137 g (2.09 mmol) sodium azide and the reaction mixture heated to 80° C. for 1 hour. It was then cooled to room temperature, poured into 30 ml of ice-water and extracted 3 times with 10 ml of ether. The combined ether phases were washed with brine, dried over magnesium sulfate and evaporated under reduced pressure giving 0.262 g (99.6%) 6-(2-Azido-ethoxy)-2-methyl-3-(4-trifluoromethyl-phenyl)-benzo[b]thiophene as colorless oil, MS: 377 (M$^+$).

50.4

0.230 g (0.610 mmol) 6-(2-Azido-ethoxy)-2-methyl-3-(4-trifluoromethyl-phenyl)-benzo[b]thiophene and 0.484 g (1.83 mmol) of triphenylphosphin were dissolved in 1.6 ml of tetrahydrofuran. After stirring of the reaction mixture for 15 minutes at room temperature, 0.1 ml of water were added and the reaction mixture heated to 60° C. for 16 hours. It was then evaporated under reduced pressure, poured into 50 ml of water and extracted 3 times with 10 ml of dichloromethane. The combined dichloromethane phases were washed with brine, dried over magnesium sulfate and evaporated under reduced pressure. The residue formed was chromatographed on silica gel with a 9:1 v/v mixture of dichloromethane and methanol as the eluent giving 0.200 g (93.4%) 2-[2-Methyl-3-(4-trifluoromethyl-phenyl)-benzo[b]thiophen-6-yloxy]-ethylamine as colorless oil, MS: 352 (MH$^+$).

50.5

In analogy to the procedures described in examples 49.3 and 49.4, 6-(4-Bromo-butoxy)-3-(4-bromo-phenyl)-2-methyl-benzo[b]thiophene (example 27.5) was reacted with sodium azide to yield 6-(4-Azido-butoxy)-3-(4-bromo-phenyl)-2-methyl-benzo[b]thiophene, which was further reduced with triphenylphosphin and water to yield 4-[3-(4-Bromo-phenyl)-2-methyl-benzo[b]thiophen-6-yloxy]-butylamine as colorless oil, MS: 390 (MH$^+$, 1Br).

Example 51

51.1

In analogy to the method described in example 17.1, Methanesulfonic acid 2-[2-methyl-3-(4-trifluoromethyl-phenyl)-benzo[b]thiophen-6-yloxy]-ethyl ester (example 50.2) was treated with methylamine in ethanol and N,N-dimethylacetamide to yield Methyl-{2-[2-methyl-3-(4-trifluoromethyl-phenyl)-benzo[b]thiophen-6-yloxy]-ethyl}-amine as colorless oil, MS: 366 (MH$^+$).

51.2

In analogy to the method described in example 17.1, 6-(4-Bromo-butoxy)-3-(4-bromo-phenyl)-2-methyl-benzo[b]thiophene (example 27.5) was treated with methylamine in ethanol and N,N-dimethylacetamide to yield {4-[3-(4-Bromo-phenyl)-2-methyl-benzo[b]thiophen-6-yloxy]-butyl}-methyl-amine as colorless oil, MS: 405 (MH$^+$).

Example 52

52.1

A solution of 40 mg (0.109 mmol) Methyl-{2-[2-methyl-3-(4-trifluoromethyl-phenyl)-benzo[b]thiophen-6-yloxy]-ethyl}-amine (example 51.1), 0.0211 g (0.164 mmol) of 4-chloro-2-methyl-pyrimidine [Ger. Offen. (1990), DE3905364 A1] and 0.038 ml (0.22 mmol) N-ethyl-diisopropylamine in 1 ml of N,N-dimethylformamide was stirred for 2 hours at 80° C. The reaction mixture was then cooled to room temperature, poured into 30 ml of ice-water and extracted 3 times with 10 ml of ether. The combined ether phases were washed with brine, dried over magnesium sulfate and evaporated under reduced pressure. The residue formed was chromatographed on silica gel with a 95:5:1 v/v/v mixture of dichloromethane, methanol and saturated aqueous ammonia as the eluent giving 37.3 mg (74.5%) Methyl-(2-methyl-pyrimidin-4-yl)-{2-[2-methyl-3-(4-trifluoromethyl-phenyl)-benzo[b]thiophen-6-yloxy]-ethyl}-amine as light brown solid, MS: 458 (MH$^+$).

In analogy to the method described in example 52.1, primary or secondary amines were reacted with halo-heterocyclic compounds in N,N-dimethylformamide to yield products as listed in the following table. The compounds were obtained as colorless or light brown oils or solids.

| Example | Product | MS MH$^+$ | Primary or Secondary Amine | Halo-Heterocycle |
|---|---|---|---|---|
| 52.2 | Methyl-{2-[2-methyl-3-(4-trifluoromethyl-phenyl)-benzo[b]thiophen-6-yloxy]-ethyl}-pyrimidin-4-yl-amine | 444 | Methyl-{2-[2-methyl-3-(4-trifluoromethyl-phenyl)-benzo[b]thiophen-6-yloxy]-ethyl}-amine | 4-Chloro-pyrimidine [PCT Int. Appl. (1998), WO9821188A1] |
| 52.3 | (2-Methyl-pyrimidin-4-yl)-{2-[2-methyl-3-(4-trifluoromethyl-phenyl)-benzo[b]thiophen-6-yloxy]-ethyl}-amine | 444 | 2-[2-Methyl-3-(4-trifluoromethyl-phenyl)-benzo[b]thiophen-6-yloxy]-ethylamine | 4-Chloro-2-methyl-pyrimidine |
| 52.4 | {2-[2-Methyl-3-(4-trifluoromethyl-phenyl)-benzo[b]thiophen-6-yloxy]-ethyl}-pyrimidin-4-yl-amine | 430 | 2-[2-Methyl-3-(4-trifluoromethyl-phenyl)-benzo[b]thiophen-6-yloxy]-ethylamine | 4-Chloro-pyrimidine |
| 52.5 | {4-[3-(4-Bromo-phenyl)-2-methyl-benzo[b]thiophen-6-yloxy]-butyl}-methyl-(2-methyl-pyrimidin-4-yl)-amine | 496, 1 Br | {4-[3-(4-Bromo-phenyl)-2-methyl-benzo[b]thiophen-6-yloxy]-butyl}-methyl-amine | 4-Chloro-2-methyl-pyrimidine |
| 52.6 | {4-[3-(4-Bromo-phenyl)-2-methyl-benzo[b]thiophen-6-yloxy]-butyl}-methyl-pyrimidin-4-yl-amine | 482, 1 Br | {4-[3-(4-Bromo-phenyl)-2-methyl-benzo[b]thiophen-6-yloxy]-butyl}-methyl-amine | 4-Chloro-pyrimidine |
| 52.7 | {4-[3-(4-Bromo-phenyl)-2-methyl-benzo[b]thiophen-6-yloxyl-butyl}-(2-methyl-pyrimidin-4-yl)-amine | 482, 1 Br | 4-[3-(4-Bromo-phenyl)-2-methyl-benzo[b]thiophen-6-yloxyl-butylamine | 4-Chloro-2-methyl-pyrimidine |
| 52.8 | {4-[3-(4-Bromo-phenyl)-2-methyl-benzo[b]thiophen-6-yloxyl]-butyl}-pyrimidin-4-yl-amine | 468, 1 Br | 4-[3-(4-Bromo-phenyl)-2-methyl-benzo[b]thiophen-6-yloxy]-butylamine | 4-Chloro-pyrimidine |
| 52.9 | {4-[3-(4-Bromo-phenyl)-2-methyl-benzo[b]thiophen-6-yloxy]-butyl}-methyl-pyridin-4-yl-amine | 481, 1 Br | {4-[3-(4-Bromo-phenyl)-2-methyl-benzo[b]thiophen-6-yloxyl-butyl}-methyl-amine | 4-Chloro-pyridine |

Example 53

53.1

A solution of 100 mg (0.220 mmol) 6-(4-Bromo-butoxy)-3-(4-bromo-phenyl)-2-methyl-benzo[b]thiophene (example 27.5), 0.024 g (0.35 mmol) of imidazole and 0.0144 g (0.330 mmol) sodium hydride (55% suspension in oil) in 0.5 ml of N,N-dimethylformamide was stirred for 1 hour at room temperature. The reaction mixture was then poured into 30 ml of ice-water and extracted 3 times with 10 ml of ether. The combined ether phases were washed with brine, dried over magnesium sulfate and evaporated under reduced pressure. The residue formed was chromatographed on silica gel with a 9:1 v/v mixture of dichloromethane and methanol as the eluent yielding 84.2 mg (86.7%) 1-{4-[3-(4-Bromo-phenyl)-2-methyl-benzo[b]thiophen-6-yloxyl]-butyl}-1H-imidazole as colorless oil, MS: 441 (MH$^+$, 1Br).

53.2

In analogy to the procedure described in example 53.1, Methanesulfonic acid 2-[2-methyl-3-(4-trifluoromethyl-phenyl)-benzo[b]thiophen-6-yloxy]-ethyl ester (example 49.2) was reacted with imidazole and sodium hydride in N,N-dimethylformamide at room temperature to yield 1-{2-[2-Methyl-3-(4-trifluoromethyl-phenyl)-benzo[b]thiophen-6-yloxy]-ethyl}-1H-imidazole as colorless oil, MS: 403 (MH$^+$).

Example A

Tablets containing the following ingredients can be manufactured in a conventional manner:

| Ingredients | Per tablet |
| --- | --- |
| Compound of formula I | 10.0–100.0 mg |
| Lactose | 125.0 mg |
| Maize starch | 75.0 mg |
| Talc | 4.0 mg |
| Magnesium stearate | 1.0 mg |

Example B

Capsules containing the following ingredients can be manufactured in a conventional manner:

| Ingredients | Per capsule |
| --- | --- |
| Compound of formula I | 25.0 mg |
| Lactose | 150.0 mg |
| Maize starch | 20.0 mg |
| Talc | 5.0 mg |

Example C

Injection solutions can have the following composition:

| | |
| --- | --- |
| Compound of formula I | 3.0 mg |
| Gelatine | 150.0 mg |
| Phenol | 4.7 mg |
| Water for injection solutions | ad 1.0 ml |

We claim:

1. A compound selected from the group consisting of compounds of formula (I)

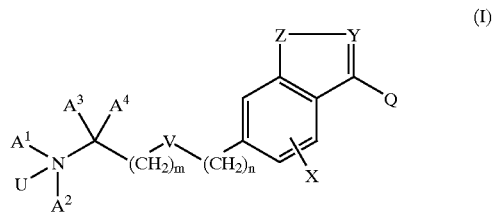

wherein
U is O or a lone pair,
Y N,
Z is S or S(O$_2$),
V is O
  m is 1 to 3
  n is 0
Q is phenyl substituted by 1–3 R$^3$ substituents,
A$^1$ is hydrogen or lower-alkyl
A$^2$ is lower-alkyl substituted with hydroxy,
A$^3$ and A$^4$ independently from each other are hydrogen or lower-alkyl,
X is hydrogen or one or more optional halogen and/or lower-alkyl substituents,
R$^3$ is halogen,
pharmaceutically acceptable salts of compounds of formula (I); and
pharmaceutically acceptable esters of compounds of formula (I).

2. The compound according to claim 1, wherein U is a lone pair.

3. The compound according to claim 2, wherein A$^1$ is hydrogen, methyl, or ethyl.

4. The compound according to claim 3, wherein A$^2$ is methyl, n-propyl, i-propyl or ethyl substituted with hydroxy.

5. The compound according to claim 2, wherein A$^3$ is hydrogen.

6. The compound according to claim 5, wherein A$^4$ is hydrogen.

7. The compound according to claim 2, wherein A$^3$ is methyl.

8. The compound according to claim 5, wherein A$^4$ is methyl.

9. The compound according to claim 2, wherein Y is N.

10. The compound according to claim 2, wherein Z is S.

11. The compound according to claim 2, wherein Z is SO$_2$.

12. The compound according to claim 2, wherein Q is phenyl substituted by 1 to 3 substituents independently selected from the group as defined for R$^3$, wherein R$^3$ is fluorine, chlorine or bromine.

13. The compound according to claim 12, wherein Q is 4-chloro-phenyl, 4-bromo-phenyl, or 4-trifluoromethyl-phenyl.

14. The compound according to claim 2, wherein X is hydrogen.

15. The compound according to claim 2, wherein Z is S(O$_2$).

16. The compound according to claim 2, wherein Z is S.

17. The compound according to claim 16, wherein $A^1$ is lower alkyl.

18. The compound according to claim 17, wherein the compound is 2-[[4-[3-(4-Bromo-phenyl)-benzo[d]isothiazol-6-yloxy]-butyl]-ethyl-amino]ethanol.

19. The compound according to claim 17, wherein the compound is 2-[[3-[3-(4-Bromo-phenyl)-benzo[d]isothiazol-6-yloxy]-propyl]ethyl-amino]-ethanol.

20. The compound according to claim 17, wherein the compound is 2-({4-[3-(4-Chloro-phenyl)-benzo[d]isothiazol-6-yloxy]butyl}methyl-amino)-ethanol.

21. A process for the manufacture of compounds according to claim 1, which process comprises reacting a compound of formula (II)

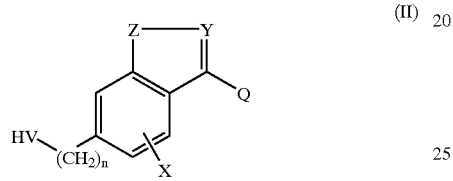

with a compound $(A^1,A^2,U)N$—$C(A^3,A^4)(CH_2)_m$—M, wherein V is O, S or $NR^2$, M is mesylate, tosylate, triflate, Cl, Br or I, and X, Y, Z, Q, U, $A^1$, $A^2$, $A^3$, $A^4$, m, n and $R^2$ have the significances given in claim 1, or wherein HV is mesylate, tosylate, triflate, Cl, Br or I, and M is OH, SH or $NHR^2$, and $R^2$ has the significance given in claim 1, or b) reacting a compound of formula (III)

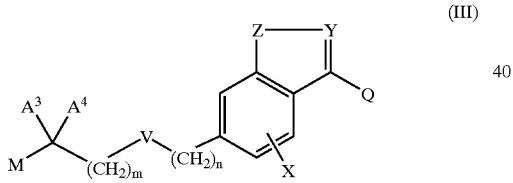

with a compound $NHA^1,A^2$, wherein M is mesylate, tosylate, triflate, Cl, Br or I, and $A^1$, $A^2$, $A^3$, $A^4$, V, X, Y, Z, Q, m and n are as defined in claim 1, or c) reacting a compound of formula (IV)

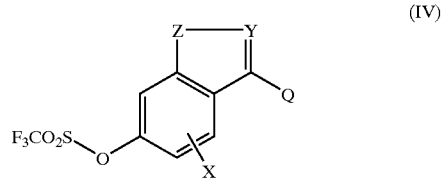

with a compound $(A^1,A^2,U)N$—$C(A^3,A^4)$—$(CH_2)_m$—$C\equiv CH$, wherein X, Y, Z, Q, U, $A^1$, $A^2$, $A^3$, $A^4$ and m are as defined in claim 1, or d) reacting a compound of formula (V)

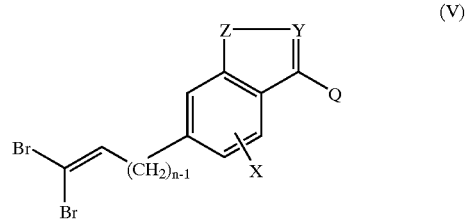

with a compound $(A^1,A^2,U)N$—$C(A^3,A^4)$—$(CH_2)_m$—M, wherein M is mesylate, tosylate, Cl, Br or I, and $A^1$, $A^2$, $A^3$, $A^4$, U, X, Y, Z, Q, m and n are as defined in claim 1, or e) hydrogenating a compound of formula (VI)

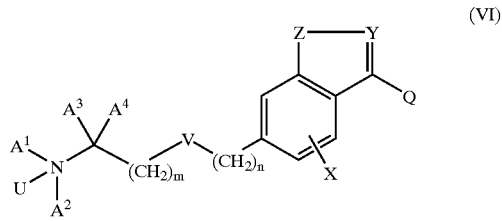

wherein V is —C≡C—, and $A^1$, $A^2$, $A^3$, $A^4$, U, X, Y, Z, Q, m and n are as defined in claim 1.

22. A pharmaceutical composition comprising a compound according to claim 1, and at least one of a pharmaceutically acceptable carrier and adjuvant.

* * * * *